(12) United States Patent
Karras

(10) Patent No.: US 8,183,363 B2
(45) Date of Patent: May 22, 2012

(54) ANTISENSE OLIGONUCLEOTIDE MODULATION OF STAT3 EXPRESSION

(75) Inventor: James G. Karras, San Marcos, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 205 days.

(21) Appl. No.: 12/429,156

(22) Filed: Apr. 23, 2009

(65) Prior Publication Data

US 2011/0054003 A1     Mar. 3, 2011

Related U.S. Application Data

(60) Continuation of application No. 11/829,279, filed on Jul. 27, 2007, now abandoned, which is a division of application No. 11/376,033, filed on Mar. 15, 2006, now Pat. No. 7,307,069, which is a division of application No. 10/773,678, filed on Feb. 6, 2004, now Pat. No. 7,098,192.

(51) Int. Cl.
     *C07H 21/04*     (2006.01)
     *C07H 21/02*     (2006.01)

(52) U.S. Cl. .......... 536/24.5; 536/23.1; 536/24.31; 536/24.33

(58) Field of Classification Search .......... None
See application file for complete search history.

(56) References Cited

U.S. PATENT DOCUMENTS

| | | | |
|---|---|---|---|
| 5,686,242 A | 11/1997 | Bruice et al. | |
| 5,719,042 A | 2/1998 | Kishimoto et al. | |
| 5,801,154 A | 9/1998 | Baracchini et al. | |
| 5,844,082 A | 12/1998 | Kishimoto et al. | |
| 6,110,667 A | 8/2000 | Lopez-Nieto et al. | |
| 6,159,694 A | 12/2000 | Karras | |
| 6,194,150 B1 * | 2/2001 | Stinchcomb et al. | 435/6 |
| 6,248,586 B1 | 6/2001 | Monia et al. | |
| 6,514,725 B1 | 2/2003 | Kishimoto et al. | |
| 6,582,908 B2 | 6/2003 | Fodor et al. | |
| 6,727,064 B2 | 4/2004 | Karras | |
| 6,727,084 B1 | 4/2004 | Hoyoux et al. | |
| 7,235,403 B2 | 6/2007 | Primiano et al. | |
| 7,307,069 B2 | 12/2007 | Karras | |
| 7,820,722 B2 * | 10/2010 | Raoof et al. | 514/784 |
| 7,834,170 B2 | 11/2010 | Khvorova et al. | |
| 2001/0053519 A1 | 12/2001 | Fodor et al. | |
| 2003/0228597 A1 | 12/2003 | Cowsert et al. | |

FOREIGN PATENT DOCUMENTS

| | | |
|---|---|---|
| EP | 0676469 | 10/1995 |
| WO | WO 96/16175 | 5/1996 |
| WO | WO 98/30688 | 7/1998 |
| WO | WO 00/61602 | 10/2000 |

OTHER PUBLICATIONS

Aberg et al., "Selective Introduction of Antisense Oligonucleotides into Single Adult CNS Progenitor Cells Using Electroporation Demonstrates the Requirement of STAT3 Activation for CNTF-Induced Gliogenesis" Molecular and Cellular Neuroscience (2001) 17:426-443.
Agrawal, "Antisense oligonucleotides: towards clinical trials" TIBTECH (1996) 14:376-387.
Akira et al., "Molecular Cloning of APRF, a Novel IFN-Stimulated Gene Factor 3 p91—Related Transcription Factor Involved in the gp 130-Mediated Signaling Pathway" Cell (1994) 77:63-71.
Barton et al., "Signal transducer and activator of transcription 3 (STAT3) activation in prostate cancer: Direct STAT3 inhibition induces apoptosis in prostate cancer lines" Molecular Cancer Therapeutics (2004) 3(1):11-20.
Braasch et al., "Novel Antisense and Peptide Nucleic Acid Strategies for Controlling Gene Expression" Biochemistry (2002) 41(14):4503-4510.
Branch, "A good antisense molecule is hard to find" TIBS (1998) 23:45-50.
Catlett-Falcone et al., "Constitutive Activation of Stat3 Signaling Confers Resistance to Apoptosis in Human U266 Myeloma Cells" Immunity (1999) 10:105-115.
Chin, "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.
Crooke, "Progress in Antisense Technology" Annual Review of Medicine: Selected Topics in the Clinical Sciences (2004) 55:61-95.
Crooke et al., "Basic Principles of Antisense Therapeutics" Antisense Research and Application (1998) Chapter 1:1-50.
Epling-Burnette et al., "Inhibition of STAT3 signaling leads to apoptosis of leukemic large granular lymphocytes and decreased Mcl-1 expression" J. of Clinical Investigation (2001) 107(3):351-361.
Ernst et al., "The Carboxyl-terminal Domains of gp130-related Cytokine Receptors are Necessary for Suppressing Embryonic Stem Cell Differentiation" J. of Biological Chemistry (1999) 274(14):9729-9737.
Gewitz et al., "Facilitating oligonucleotide delivery: Helping antisense deliver on its promise" PNAS (1996) 93:3161-3163.
Grandis et al., "Requirement of Stat3 but not Stat1 Activation for Epidermal Growth Factor Receptor—mediated Cell Growth in Vitro" J. Clin. Invest. (1998) 102(7):1385-1392.
Groothuis, "The blood-brain and blood-tumor barriers: A review of strategies for increasing drug delivery" Oncology (2000) 2(1):45-59.
James, "Towards gene-inhibition therapy: a review of progress and prospects in the field of antiviral antisense nucleic acids and ribozymes" Antiviral Chemistry & Chemotherapy (1991) 2(4):191-214.

(Continued)

*Primary Examiner* — Amy Bowman
(74) *Attorney, Agent, or Firm* — Isis Pharmaceuticals, Inc. Patent Dept.

(57) ABSTRACT

Compounds, compositions and methods are provided for inhibiting the expression of human STAT3. The compositions comprise antisense oligonucleotides targeted to nucleic acids encoding STAT3. Methods of using these oligonucleotides for inhibition of STAT3 expression and for promotion of apoptosis are provided. Methods for treatment of diseases, particularly inflammatory diseases and cancers, associated with overexpression or constitutive activation of STAT3 or insufficient apoptosis are also provided.

15 Claims, No Drawings

OTHER PUBLICATIONS

Jen et al., "Suppression of Gene Expression by Targeted Disruption of Messenger RNA: Available Options and Curren Strategies" Stem Cells (2000) 18:307-319.

Karras et al., "STAT3 Regulates the Growth and Immunoglobulin Production of BCL1 B Cell Lymphona through Control of Cell Cycle Progression" Cellular Immunology (2000) 202:124-135.

Konnikova et al., "Knockdown of STAT3 expression by RNAi induces apoptosis in astrocyoma cells" BMC Cancer (2003) 2(23):1-9.

Lamy, "Dysregulation of CD95/CD95 Ligand-Apoptotic Pathway in CD3+ Large Granular Lymphocyte Leukemia" Blood (1998) 92(12):4771-4777.

Liu et al., "Serine phosphorylation of STAT3 is essential for Mcl-1 expression and microphage survival" Blood (2003) 102(1):344-352.

Mahato et al., "Modulation of gene expression by antisense and antigene oligodeoxynucleotides and small interfering RNA" Expert Opinion on Drug Delivery (2005) 2(1):3-28.

Mahboubi et al., "Desensitization of Signaling by Oncostatin M in Human Vascular Cells Involves Cytoplasmic Tyr Residue 759 in gp130 but is Not Mediated by Either Src Homology 2 Domain-containing Tyrosine Phosphatase 2 or Suppressor of Cytokine Signaling 3" J. of Biological Chemistry (2003) 278(27):25014-25023.

Matzura et al., "RNA draw: an integrated program for RNA secondary structure calculation and analysis under 32-bit Microsoft Windows" Computer Applications in the Biosciences (1996) 12(3):247-249.

Milner et al., "Selecting effective antisense reagents on combinatorial oligonucleotide arrays" Nature Biotechnology (1997) 15:537-541.

Mora et al., "Constitutive Activation of Stat3 in Human Prostate Tumors and Cell Lines: Direct Inhibition of Stat3 Signaling Induces Apoptosis of Prostate Cancer Cells" Cancer Research (2002) 62:6659-6666.

New England Biolabs 1998/99 Catalog (cover page and pp. 121 and 284).

Niu et al., "Gene Therapy with Dominant-negative Stat3 Suppresses Growth of Murine Melanoma B16 Tumor in Vivo" Cancer Research (1999) 59:5059-5063.

Niu et al., "Constitutive Stat3 activity up-regulates VEGF expression and tumor angiogenesis" Oncogene (2002) 21:2000-2008.

Olie et al., "A Novel Antisense Oligonucleotide Targeting Survivin Expression Induces Apoptosis and Sensitizes Lung Cancer Cells to Chemotherapy" Cancer Research (2000) 60:2805-2809.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Scherer et al., "Approaches for the sequence-specific knockdown of mRNA" Nat. Biotechnol. (2003) 21(12):1457-1465.

Song et al., "Activation of Stat3 by receptor tyrosine kinases and cytokines regulates survival in human non-small cell carcinoma cells" Oncogene (2003) 22:4150-4165.

Tamm et al., "Antisense therapy in oncology: new hope for an old idea?" The Lancet (2001) 358:489-497.

Zhong et al., "Stat3: A STAT Family Member Activated by Tyrosine Phosphorylation in Response to Epidermal Growth Factor and Interleukin-6" Science (1994) 264:95-98.

STAT3 Antisense Oligonucleotide Sequence Search Results.

International Search Report for application No. PCT/US00/09054 dated Jun. 12, 2000.

International Search Report for application No. PCT/US04/32130 dated Apr. 25, 2005.

European Search Report for application No. EP 00921727 dated May 23, 2002.

* cited by examiner

SEQUENCE LISTING

<160> NUMBER OF SEQ ID NOS: 406

<210> SEQ ID NO 1
<211> LENGTH: 2787
<212> TYPE: DNA
<213> ORGANISM: Homo sapiens

<400> SEQUENCE: 1

| | | | | | |
|---|---|---|---|---|---|
| cagctggaat | tcggggcggc | ggcgcagact | gggaggggga | gccgggggtt | ccgacgtcgc | 60 |
| agccgaggga | acaagcccca | accggatcct | ggacaggcac | cccggcttgg | cgctgtctct | 120 |
| cccctcggc | tcggagaggc | ccttcggcct | gagggagcct | cgccgcccgt | ccccggcaca | 180 |
| cgcgcagccc | cggcctctcg | gcctctgccg | gagaaacagg | atgcccaat | ggaatcagct | 240 |
| acagcagctt | gacacacggt | acctggagca | gctccatcag | ctctacagtg | acagcttccc | 300 |
| aatggagctg | cggcagtttc | tggccccttg | gattgagagt | caagattggg | catatgcggc | 360 |
| cagcaaagaa | tcacatgcca | ctttggtgtt | tcataatctc | ctgggagaga | ttgaccagca | 420 |
| gtatagccgc | ttcctgcaag | agtcgaatgt | tctctatcag | cacaatctac | gaagaatcaa | 480 |
| gcagtttctt | cagagcaggt | atcttgagaa | gccaatggag | attgcccgga | ttgtggcccg | 540 |
| gtgcctgtgg | gaagaatcac | gccttctaca | gactgcagcc | actgcggccc | agcaaggggg | 600 |
| ccaggccaac | caccccacag | cagccgtggt | gacggagaag | cagcagatgc | tggagcagca | 660 |
| ccttcaggat | gtccggaaga | gagtgcagga | tctagaacag | aaaatgaaag | tggtagagaa | 720 |
| tctccaggat | gactttgatt | tcaactataa | aaccctcaag | agtcaaggag | acatgcaaga | 780 |
| tctgaatgga | aacaaccagt | cagtgaccag | gcagaagatg | cagcagctgg | aacagatgct | 840 |
| cactgcgctg | gaccagatgc | ggagaagcat | cgtgagtgag | ctggcggggc | ttttgtcagc | 900 |
| gatggagtac | gtgcagaaaa | ctctcacgga | cgaggagctg | gctgactgga | agaggcggca | 960 |
| acagattgcc | tgcattggag | gcccgcccaa | catctgccta | gatcggctag | aaaactggat | 1020 |
| aacgtcatta | gcagaatctc | aacttcagac | ccgtcaacaa | attaagaaac | tggaggagtt | 1080 |
| gcaccaaaaa | gtttcctaca | aagggggaccc | cattgtacag | caccggccga | tgctggagga | 1140 |
| gaggatcgtg | gagctgttca | gaaacttaat | gaaaagtgcc | tttgtggtgg | agcggcagcc | 1200 |
| ctgcatgccc | atgcatcctg | accggccccct | cgtcatcaag | accggcgtcc | agttcactac | 1260 |
| taaagtcagg | ttgctggtca | agttccctga | gttgaattat | cagcttaaaa | ttaaagtgtg | 1320 |
| cattgacaaa | gactctgggg | acgttgcagc | tctcagagga | tcccggaaat | ttaacattct | 1380 |
| gggcacaaac | acaaaagtga | tgaacatgga | agaatccaac | aacggcagcc | tctctgcaga | 1440 |
| attcaaacac | ttgaccctga | gggagcagag | atgtgggaat | gggggccgag | ccaattgtga | 1500 |
| tgcttccctg | attgtgactg | aggagctgca | cctgatcacc | tttgagaccg | aggtgtatca | 1560 |
| ccaaggtctc | aagattgacc | tagaccccca | ctccttgtca | gttgtggtga | tctccaacat | 1620 |
| ctgtcagatg | ccaaatgcct | gggcgtccat | cctgtggtac | aacatgctga | ccaacaatcc | 1680 |
| caagaatgtg | aacttcttca | ctaagccgcc | aattggaacc | tgggaccaag | tggccgaggt | 1740 |
| gctcagctgg | cagttctcgt | ccaccaccaa | gcggggggctg | agcatcgagc | agctgacaac | 1800 |
| gctggctgag | aagctcctag | gcctggtgt | gaactactca | gggtgtcaga | tcacatgggc | 1860 |
| taacttctgc | aaagaaaaca | tggctggcaa | gggcttctcc | tactgggtct | ggctagacaa | 1920 |
| tatcatcgac | cttgtgaaaa | agtatatctt | ggccctttgg | aatgaagggt | acatcatggg | 1980 |
| tttcatcagc | aaggagcggg | agcgggccat | cttgagcact | aagcccccag | gcaccttcct | 2040 |

-continued

```
gctgcgcttc agtgaaagca gcaaagaagg aggcgtcact ttcacttggg tggagaagga      2100
catcagcggt aagacccaga tccagtccgt ggaaccatac acaaagcagc agctgaacaa      2160
catgtcattt gctgaaatca tcatgggcta aagatcatg gatgctacca atatcctgtt       2220
gtctccactt gtctatctct atcctgacat tcccaaggag gaggcattcg ggaagtattg      2280
tcggccagag agccaggagc atcctgaagc tgacccaggt agcgctgccc catacctgaa      2340
gaccaagttt atctgtgtga caccaacgac ctgcagcaat accattgacc tgccgatgtc      2400
cccccgcgct ttagattcat tgatgcagtt tggaaataat ggtgaaggtg ctgaaccctc      2460
agcaggaggg cagtttgagt ccctcacctt tgacatggag ttgacctcgg agtgcgctac      2520
ctcccccatg tgaggagctg agaacggaag ctgcagaaag atacgactga ggcgcctacc      2580
tgcattctgc caccctcac acagccaaac cccagatcat ctgaaactac taactttgtg       2640
gttccagatt tttttaatc tcctacttct gctatctttg agcaatctgg gcacttttaa       2700
aaatagagaa atgagtgaat gtgggtgatc tgcttttatc taaatgcaaa taaggatgtg      2760
ttctctgaga cccatgatca ggggatg                                          2787
```

```
<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gtctgcgccg ccgccccgaa                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
ggccgaaggg cctctccgag                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
tcctgtttct ccggcagagg                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
catcctgttt ctccggcaga                                                    20

<210> SEQ ID NO 6
<211> LENGTH: 20
<212> TYPE: DNA
<213> ORGANISM: Artificial Sequence
<220> FEATURE:
```

```
<223> OTHER INFORMATION: Synthetic Oligonucleotide

<400> SEQUENCE: 6
gccatcctgt ttctccggca                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
gggccatcct gtttctccgg                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
ttgggccatc ctgtttctcc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
cattgggcca tcctgtttct                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
tccattgggc catcctgttt                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
attccattgg gccatcctgt                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tgattccatt gggccatcct                                               20

<210> SEQ ID NO 13
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
gctgattcca ttgggccatc                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tagctgattc cattgggcca                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
tgtagctgat tccattgggc                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ctgtagagct gatggagctg                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
cccaatcttg actctcaatc                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
cccaggagat tatgaaacac                                            20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
```
acattcgact cttgcaggaa                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
tctgaagaaa ctgcttgatt                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
ggccacaatc cgggcaatct                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
tggctgcagt ctgtagaagg                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
ctgctccagc atctgctgct                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tttctgttct agatcctgca                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
tagttgaaat caaagtcatc                                          20

<210> SEQ ID NO 26
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 26
ttccattcag atcttgcatg    20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
tctgttccag ctgctgcatc    20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tcactcacga tgcttctccg    20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
gagttttctg cacgtactcc    20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
atctgttgcc gcctcttcca    20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
ctagccgatc taggcagatg    20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
cgggtctgaa gttgagattc    20

<210> SEQ ID NO 33

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
cggccggtgc tgtacaatgg                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
tttcattaag tttctgaaca                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
aggatgcatg ggcatgcagg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
gaccagcaac ctgactttag                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
atgcacactt taattttaag                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ttccgggatc ctctgagagc                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
```

```
ttccatgttc atcacttttg                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
gtcaagtgtt tgaattctgc                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
caatcaggga agcatcacaa                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
tacacctcgg tctcaaaggt                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tgacaaggag tgggtctcta                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
cgcccaggca tttggcatct                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
cattcttggg attgttggtc                                              20

<210> SEQ ID NO 46
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 46
cacttggtcc caggttccaa                                                   20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
cccgcttggt ggtggacgag                                                   20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
agttcacacc aggccctagg                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
gttttctttg cagaagttag                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
atattgtcta gccagaccca                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
aacccatgat gtaccttca                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
gcttagtgct caagatggcc                                                   20

<210> SEQ ID NO 53

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
gctgctttca ctgaagcgca                                                     20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gtgaaagtga cgcctccttc                                                     20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
ctgatgtcct tctccaccca                                                     20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
actggatctg ggtcttaccg                                                     20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
aaatgacatg ttgttcagct                                                     20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
gcccatgatg atttcagcaa                                                     20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
```
tattggtagc atccatgatc                                           20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
atagacaagt ggagacaaca                                           20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ttgggaatgt caggatagag                                           20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
ctcctggctc tctggccgac                                           20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
acctgggtca gcttcaggat                                           20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
cacagataaa cttggtcttc                                           20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
atcggcaggt caatggtatt                                           20

<210> SEQ ID NO 66
<211> LENGTH: 20
<212> TYPE: DNA
<213> ORGANISM: Artificial Sequence
<220> FEATURE:

-continued

<223> OTHER INFORMATION: Synthetic Oligonucleotide

<400> SEQUENCE: 66
ccaaactgca tcaatgaatc                                           20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
ggttcagcac cttcaccatt                                           20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
gagggactca aactgccctc                                           20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
caactccatg tcaaaggtga                                           20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
ttctcagctc ctcacatggg                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
cgttctcagc tcctcacatg                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tccgttctca gctcctcaca                                           20

<210> SEQ ID NO 73

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
cttccgttct cagctcctca                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
agcttccgtt ctcagctcct                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
agaatgcagg taggcgcctc                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
accacaaagt tagtagtttc                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
tgctcaaaga tagcagaagt                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
attcactcat ttctctattt                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
```

```
catttagata aaagcagatc                                                  20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
acatccttat ttgcatttag                                                  20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
gatcatgggt ctcagagaac                                                  20

<210> SEQ ID NO 82
<211> LENGTH: 2869
<212> TYPE: DNA
<213> ORGANISM: Mus musculus

<400> SEQUENCE: 82
gccgcgacca gccaggccgg ccagtcgggc tcagcccgga gacagtcgag acccctgact      60
gcagcaggat ggctcagtgg aaccagctgc agcagctgga cacacgctac ctgaagcagc     120
tgcaccagct gtacagcgac acgttcccca tggagctgcg gcagttcctg gcaccttgga     180
ttgagagtca agactgggca tatgcagcca gcaaagagtc acatgccacg ttggtgtttc     240
ataatctctt gggtgaaatt gaccagcaat atagccgatt cctgcaagag tccaatgtcc     300
tctatcagca caaccttcga agaatcaagc agtttctgca gagcaggtat cttgagaagc     360
caatggaaat tgcccggatc gtggcccgat gcctgtggga agagtctcgc ctcctccaga     420
cggcagccac ggcagcccag caaggggggcc aggccaacca cccaacagcc gccgtagtga     480
cagagaagca gcagatgttg gagcagcatc ttcaggatgt ccggaagcga gtgcaggatc     540
tagaacagaa aatgaaggtg gtggagaacc tccaggacga ctttgatttc aactacaaaa     600
ccctcaagag ccaaggagac atgcaggatc tgaatggaaa caaccagtct gtgaccagac     660
agaagatgca gcagctggaa cagatgctca cagccctgga ccagatgcgg agaagcattg     720
tgagtgagct ggcgggggctc ttgtcagcaa tggagtacgt gcagaagaca ctgactgatg     780
aagagctggc tgactggaag aggcggcagc agatcgcgtg catcggaggc cctcccaaca     840
tctgcctgga ccgtctggaa aactggataa cttcattagc agaatctcaa cttcagaccc     900
gccaacaaat taagaaactg gaggagctgc agcagaaagt gtcctacaag gcgaccccta     960
tcgtgcagca ccggccccatg ctggaggaga ggatcgtgga gctgttcaga aacttaatga    1020
agagtgcctt cgtggtggag cggcagccct gcatgcccat gcacccggac cggcccttag    1080
tcatcaagac tggtgtccag tttaccacga aagtcaggtt gctggtcaaa tttcctgagt    1140
tgaattatca gcttaaaatt aaagtgtgca ttgataaaga ctctggggat gttgctgccc    1200
tcagagggtc tcggaaattt aacattctgg gcacgaacac aaaagtgatg aacatggagg    1260
agtctaacaa cggcagcctg tctgcagagt tcaagcacct gacccttagg gagcagagat    1320
gtgggaatgg aggccgtgcc aattgtgatg cctccttgat cgtgactgag gagctgcacc    1380
```

```
tgatcacctt cgagactgag gtgtaccacc aaggcctcaa gattgaccta gagacccact    1440
ccttgccagt tgtggtgatc tccaacatct gtcagatgcc aaatgcttgg gcatcaatcc    1500
tgtggtataa catgctgacc aataacccca agaacgtgaa cttcttcact aagccgccaa    1560
ttggaacctg ggaccaagtg gccgaggtgc tcagctggca gttctcgtcc accaccaagc    1620
gagggctgag catcgagcag ctgacaacgc tggctgagaa gctcctaggg cctggtgtga    1680
actactcagg gtgtcagatc acatgggcta aattctgcaa agaaaacatg gctggcaagg    1740
gcttctcctt ctgggtctgg ctagacaata tcatcgacct tgtgaaaaag tatatcttgg    1800 cccctttggaa tgaagggtac atcatggggtt tcatcagcaa ggagcgggag cgggccatcc   1860
taagcacaaa gccccccgggc accttcctac tgcgcttcag cgagagcagc aaagaaggag    1920
gggtcacttt cacttgggtg gaaaaggaca tcagtggcaa gacccagatc cagtctgtag    1980
agccatacac caagcagcag ctgaacaaca tgtcatttgc tgaaatcatc atgggctata    2040
agatcatgga tgcgaccaac atcctggtgt ctccacttgt ctacctctac cccgacattc    2100
ccaaggagga ggcatttgga aagtactgta ggcccgagag ccaggagcac cccgaagccg    2160
acccaggtag tgctgccccg tacctgaaga ccaagttcat ctgtgtgaca ccaacgacct    2220
gcagcaatac cattgacctg ccgatgtccc cccgcacttt agattcattg atgcagtttg    2280
gaaataacgg tgaaggtgct gagccctcag caggagggca gtttgagtcg ctcacgtttg    2340
acatggatct gacctcggag tgtgctacct cccccatgtg aggagctgaa accagaagct    2400
gcagagacgt gacttgagac acctgccccg tgctccaccc ctaagcagcc gaacccata    2460 tcgtctgaaa ctcctaactt tgtggttcca gatttttttt tttaatttcc tacttctgct    2520
atctttgggc aatctgggca cttttttaaaa gagagaaatg agtgagtgtg ggtgataaac    2580
tgttatgtaa agaggagaga cctctgagtc tggggatggg gctgagagca gaagggaggc    2640
aaaggggaac acctcctgtc ctgcccgcct gccctccttt ttcagcagct cgggggttgg    2700
ttgttagaca agtgcctcct ggtgcccatg gctacctgtt gccccactct gtgagctgat    2760 acccccattct gggaactcct ggctctgcac tttcaacctt gctaatatcc acatagaagc    2820
taggactaag cccaggaggt tcctctttaa attaaaaaaa aaaaaaaa                  2869
```

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gttccactga gccatcctgc                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
ttcaggtagc gtgtgtccag                                               20

<210> SEQ ID NO 85
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 85
atgtgactct ttgctggctg                                                     20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
ccaagagatt atgaaacacc                                                     20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
gctccaacat ctgctgcttc                                                     20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
gctcttcatc agtcagtgtc                                                     20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
atctgacacc ctgagtagtt                                                     20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
gccagaccca gaaggagaag                                                     20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
cgctccttgc tgatgaaacc                                                     20

<210> SEQ ID NO 92

<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
aacttggtct tcaggtacgg    20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
atcaatgaat ctaaagtgcg    20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
tcagcacctt caccgttatt    20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
actcaaactg ccctcctgct    20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
ggtttcagct cctcacatgg    20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
taaaaaaaaa aatctggaac    20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
aagatagcag aagtaggaaa                                                    20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
aaaaagtgcc cagattgccc                                                    20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
atcacccaca ctcactcatt                                                    20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
cctttgcctc ccttctgctc                                                    20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
tgaaaaagga gggcaggcgg                                                    20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
caccaggagg cacttgtcta                                                    20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
aacctcctgg gcttagtcct                                                    20

<210> SEQ ID NO 105
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 105
aaaaagtgcg cagattgccc        20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
aaaaagtccg ctgattgccc        20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
aaaaactccg ctgaatgccc        20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
atgtgattct ttgctggccg        20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
agctgattcc attgggccat        20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
ccaggagatt atgaaacacc        20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
accgtgtgtc aagctgctgt        20

<210> SEQ ID NO 112

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
ccattgggaa gctgtcactg                                        20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
tgtgattctt tgctggccgc                                        20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
gcggctatac tgctggtcaa                                        20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
gctccagcat ctgctgcttc                                        20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
gattcttccc acaggcaccg                                        20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
tgattcttcc cacaggcacc                                        20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
```

```
atcctgaagg tgctgctcca                                            20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
cggacatcct gaaggtgctg                                            20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
cccgccagct cactcacgat                                            20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
agtcagccag ctcctcgtcc                                            20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
ccagtcagcc agctcctcgt                                            20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
cgcctcttcc agtcagccag                                            20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
ggccggtgct gtacaatggg                                            20

<210> SEQ ID NO 125
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 125
atcctctcct ccagcatcgg                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
ccgctccacc acaaaggcac                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
cgtccccaga gtctttgtca                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
ttgtgtttgt gcccagaatg                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
gctcggcccc cattcccaca                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
aggcatttgg catctgacag                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
cttgggattg ttggtcagca                                              20

<210> SEQ ID NO 132

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
ctcggccact tggtcccagg                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
ccccgcttgg tggtggacga                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
cccccgcttg gtggtggacg                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
ggagaagccc ttgccagcca                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
ttcattccaa agggccaaga                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
cccgctcctt gctgatgaaa                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
```

```
gtgctcaaga tggcccgctc                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
cccaagtgaa agtgacgcct                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
acccaagtga agtgacgcc                                                20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
ccgaatgcct cctccttggg                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
gccgacaata cttcccgaat                                               20

<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
gatgctcctg gctctctggc                                               20

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
tcaatgaatc taaagcgcgg                                               20

<210> SEQ ID NO 145
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 145
gactcaaact gccctcctgc                                                  20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
atcacccaca ttcactcatt                                                  20

<210> SEQ ID NO 147
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 147
aaaagtgccc agattgc                                                     17

<210> SEQ ID NO 148
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 148
aaaagtgccc agattgctca                                                  20

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
taaaagtgcc cagattgctc                                                  20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 150
aagcagatca cccacattca                                                  20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 151
aaaaagaggc ctgattgccc                                                  20

<210> SEQ ID NO 152

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 152
tctggcaaag tgtcagtatg                                                  20

<210> SEQ ID NO 153
<211> LENGTH: 74424
<212> TYPE: DNA
<213> ORGANISM: H. sapiens

<400> SEQUENCE: 153
agagcgggca ggagggagct gtatcagggg catttaaagt gccttgacgt cacgcactgc      60
caggaactca gctgagtttt cagcaggaca ttccggtcat cttccctccc tcccccgggg     120
cttctgtgcc caagtcctcg gctcttccct cgctgtggcg gagggaggag caccgaactg     180
tcggaacagc cagcacaggg gcgtatcagt ctcctcttgg ctccgccctt tctcctagct     240
gctctcctca ttggtcagtg ggcggggctt cggctgtacc gcacacgcac tgggaccttct    300 gggtggccga acgagctggc ctttcatgaa ttatgcatga cggcgtgcct cggccaggct     360
ggggctgggc gaggattggc tgaagggct gtaattcagc ggtttccgga gctgcggcgg      420
cgcagactgg gaggggagc cgggggttcc gacgtcgcag ccgagggaac aagccccaac     480
cggatcctgg acaggcaccc cggcttggcg ctgtctctcc cctcggctc ggagaggccc     540 ttcggcctga gggagcctcg ccgcccgtcc ccggcacacg cgcagcccccg gcctctcggc    600 ctctgccgga gaaacaggtg aagggggtgc agggtggggc cgttggggag gcctggggac    660
ccgggggctc cgcagcggca ggggggcctct gggaccttgg ggatgttgtg atggacgctg    720
cagtggggcc gggagagatg aagagacgcg gagggtcgcc ctgagggaag actcttcggg    780
atgacaggag cgggcctcgg aagggactcg gggcgctgga gggaagtttc gttcttcgga    840
gaaacagaac gcgctcgagg gggcaccgtg gggcgagggc gcactcggtt gcggcggcag    900
gagtgaggga cagtccccccg atttcctgct ccctgggggcc ctggggacgt tccggccacc    960
ggagcgactg tcacgccgac ggggatcacc ggcgcgagtg gggggtcgga aagcgcctcc   1020
tccccgcccg gtcggcggct cccgctgagc cacttcctcc gcttgccctg ttcccgctcc    1080
ttcaggagac agctgtgccc ttttggaggc aggaataggt gtgtctgtcg cctgcagcct    1140
tacgggctgg ctggtcgtgg gtaggcttta ttgcataaga atcaagtttc ctgtagggaa   1200
attgacagac cggtactctt tctaaattcc ctcgcatctt tttctaggtt aaattatgct    1260
ccccccacgt ccccgccttg taaaaagag aaaaaaagac aaaataaaat ccccatcaac    1320
ccgtcaagcc agctctagag agagaaataa acctcttgac attgtccttt tccaaatacc   1380
tggtaaagtc ggccagaaga taaataattg agccattgca tttactggat tgtggtgttg    1440
cttaattgca taggacggaa tgaaccaatt gagagtggga gttttctgtc tcagagccaa    1500
gatcttgggt aaatgcagag gagagggaaa caaagacagg ctggccttga aaaaaccatg    1560
tgtgcaaact ttacatgcat ttgggggggtg tggttgcact gaagttaaca agattcaaac    1620
cgtcgcccaa gttggtattt ccatgttttgg tacacatcac tctgtgccat atcaggtcgt    1680
tgttaagtgt ggtgacaaaa tcagtggtta gtcatttttt taattaaaaa tgtgtatagt    1740
gtgtacctgc tggtcttact gtatgtgcaa ctaaaggttt acatagtctg tgtatgggtt    1800
gtaaattttt ggctggctgt gctgataaag cattgggctt gaataaagca aagcagaaaa   1860
```

```
tcatctcaat cttttatatg tggatttaga ctgtgttatg acttggttca gccagttttc   1920
tatcttattt tatattaaat atgtctgtgt tctctgagtc agcacattta tttccttatt   1980
acatgttcca gacaggagtg ctagcccagt ttttgttcag tttgcacagt gggatgggga   2040
aacaagtctg gaatttaaaa aaaaatgttt tagaggttgg agccttgatt ttagtctcta   2100
tattagcaca tccatcacaa agaaccatta gtaaattcat gaatcttttg ttttttatgt   2160
agttcatttg agaagaataa tcacttagaa atatccacag tgccaggcat ggtggtgcac   2220
acctctgatc ccagctaatt gaaggctgag gtgggaggat tccttgagtc aggagttga   2280 gtctggtctg ggcaacatgg tgagaggcca ggaattgggt ctagagtcta gtctaagcac   2340
cataatgaga acccatcttt aagaaagaaa gaaggaaag gaggaagaaa ggaaagaaaa   2400
agaaataccc acagcacagt tatgaattaa cccacaaagg acttgtgagg tgggtagttc   2460
acataacaat taccctaata tcgtagataa gaaaattgag gccaaaggat caagacactt   2520
ggccaacgca gcagagtgcc atagtggtgg aatttgtgcc tccttctgta tattttgtga   2580
aaagtatcag tgaaattctt tttttttttt ttttgagtc agagtcttgc tctgttgccc   2640
aggctagagt gcagtggcgc aatcttggct cactgcaacc tctgcctcct gggttcaagc   2700
gattctcctg cctcagcctc ccaagtagct gggactacag gcgtgcgcca ccacgcccag   2760 ctaattttg tattttagt agagaccggg gttttaccat attggccagg ctggtcttga   2820
actcctgacc ttgtgatttg cccacctcta tctcccaaag tgctgggatt acaggtgtga   2880
gccaccgcgc ccagtaagta tcagtgaaat tctaacatat atctgaacag taaaatacca   2940
ccaataggct gaaagacttc atgggaggta aatattcaat aaacaggtga aaaagaaat   3000 acaaatggag cttgcttaga ttattttct aattgctatg tctaacttgg gaagtgagga   3060 actgttttg gtcagcataa tttaccatca gaatttagct atttactaat gaaaagaaat   3120
actaatctag gtttgtttta gattaaggac agtcatgacc taaatgtcat ttaaaccaga   3180
gtgcattgtg gcttgatcag tggtcatttc tgtctctaga aagttgcttt aacttctctg   3240
cctctacgtg tctcttgaca ttcagatatg aggtggggta gaggtggtga ccaactttcc   3300
agacgcctga gtccaaacct tcttagctta tggttttctt aggtgatgtg caaatcaaca   3360
aatatatact tttttttttt ttttttgag ttggagttgc actctatcac ccaggctgga   3420
gtgcagtggc atgatcgtgg ctcactgcaa cctcctcctc ccgggttcaa gtgattctcg   3480
cacctcagcc tcctgagtag ctgggattac aggtgccgc cactacgccc ggctaatttt   3540 tgtatttta gtagagataa ggtttcacta tattgaccag gctggtctca aactcctgac   3600
ctcaagagat ctgcccacct cagcctccca agtgctggg attacaggcg tgaaccacct   3660
tgcctggcca acatatatat acctttgca actttgtcag agttgctatg aagaataagt   3720
tgtatcttgt tcacagaaat tgcagtctac tgggggagct gataaatgtt ttaaccatcc   3780
aatgtaacat gttgtcatca aagagatggt gagactttac acttgtgcta acaaggtagc   3840
tgttctacat aaaagaacat acagtacaga tgtagaactt ttctgttatc atagaacgtt   3900
ctattggaca gtgctaggct gaatgctaca gatcttcaga gaaggagag ttatgaggc   3960 ctggagttgt ctagaaagtc ttttgccaa agagggattt caactgggtc ccaaataatg   4020
ggtgaatttt gataggtgta aagaatttgc ggtggtttat gcctgtaatc ccagcacttt   4080
gggaggctga ggcaggagga ttgcttgagc ccaggagttt gagaccagct tgggcaacgt   4140
ggtaaaactc cctctcccct aaaaataaaa aaaattagcc aggcctggtg gcgtggacct   4200
gtagtcccag ctactggtga gactaaggtg ggaggatcac caagcccg ggggttaagg   4260
```

```
ctgcagtgag ccgtgatccc gccaccgcac tccagcctgg gtgacagagt gagaccctgt    4320
ctccaaaaaa aaaaaaaatt cctggtagcc cggtagacta ggagggtaag taggggagaa    4380
gtgattactt acaaaagaca ttgaatacag gaccaaggaa tttcagttct gttcttttgt    4440
aggggaagct tttaaaactt tcggggcgcc gggcgcggtg gctcacgcct gtaatcccag    4500
cactttggga ggcccagacg cgcggatcac gaggccagga gatcgagacc atcctggcta    4560
acacggtgaa accccatctc tactaaaaat acaaaaaaaa gtagccgggc gttgtggcgg    4620
gcgtctgtag tcccagctac tcgggaggct gaggcaggag aagagcgtga actcgggagg    4680
cggagcttgc agtgagccga tatcgcacca ctgcactcca gcctgggcga cagagcgaga    4740
ctccgtctca aaaaaaaaa aaataaataa ataaataaat aaataaaact tggagccga    4800 agcactgatt tttaatcata gagtgcttac tatgtgttag gcacaggcct gattgcctga    4860
tgctggttaa tttgtacaaa gtaaatcagt gcatatgccc tctgccctag gggagttatt    4920
aactggagtc tgacattgta caaaggtagg tatcctgact agtttgattt ggtactttgg    4980
gtgaaaaaag tatagtgtgc ttaagtgcag aagtgttttt tgaggatttt tgattggata    5040
caaaccacca ctcatatttt atgtctttgg cacttaaaaa tttcaccata acttttgagt    5100
catttataaa aaccactgaa agagtacttg agggacatcc ccgaatcctg aagaacttct    5160
ggtgttctgg agcagcctca gtgagatcca ggaggatggc attgctgggc tggcccagcc    5220
cttattgatt atggtgtaaa gaattaatat ggtggttata tactctttgt tagacacctt    5280
ggcttacaag acgtaagcgt aaagtgtagt gcgctttagt cagtatggcc acatggtcct    5340
ttggtggtaa attgtttgag atgcctccag ttttaaaag gagtagcata tcgggccagg    5400
agcagtggct catgcctata atcccagcac tttggaaggc cgaggcaaga ggattgcttg    5460
agcccaggag ttcaagacca gcctgggcaa catagtgaga ccactttgtt tctttaaaaa    5520
aaaaaaaaag gcaaaacag gctgggcatg gtggctgatg cctgtaatcc cagcgctttg    5580
tgaggcagag gtgagcggat cacttgaggt caggagtttg agaccagcct ggccaacatg    5640
gtaaaacccc gtctctacta aaaatacaaa aattagccag gtgtggtggc acacgcctgt    5700
agttccagct actctggagg ctgagccagg agaattgctt gaacctggga ggtggaggct    5760
gcagtgagcc aagatcctgc cactgcactc cagactgggg gacagagtga gacattctga    5820
cagtgctaca ctgaatgcta catgtcttca gaggaaggag aggttatgag gcctgggaat    5880
aacatatgga agaatgaatt tctgttatgg tcagttctca tttgtcatgt taggattact    5940
gcaactctta cccagccggg tgtggtggct catgcctgta attccagcac tttgggaggc    6000
tgtgggcgga tcacgaggtc aggagatcga gaccatcctg gctaacacgg tgaaactccg    6060
cctctactaa aaatacaaaa aattagccca gcgtggtggc gacgcctgt agtcccagct    6120 actcaggagg ctgaggcagg agaatggcat gagtcctgga ggcggagctt gcagtgagct    6180
gagatcgtgc cactgcactc cagcctgggc aacagagtgg gactccatct caaaaaaaaa    6240 agaaaaaaa aaggattacc gcaactcttt aattcagatc agcaaacatg ttgagagcca    6300
ggtattgcgt caggcaggat ccaaggataa tgaaatattg tccgttttca tgaaactgga    6360
gatgttgcag ggaccgaggt gtgtgctatg ccagtatgga agtaggacag gggagacgac    6420
agggcagtga gtggttcaag actctggctc tgaagtcaaa cagatctggg actgaatcct    6480
ggatctgcca cttcctagtc agaatctgag cctctatttt cttatctgta aagaagatt    6540 ataacagtgc ttatcttgta ggtactgttg acgattcaat aagataatgt ggataaaatg    6600
cttagcatag tgcctggcac atagtaagag ctcggtaaat ctaagttctt actaaatatc    6660
```

```
caagaaaaga gattaattct tttcaggagt gagagaaagt catcattatt gagggggcttt    6720 atcagatggg aacacctgaa tagggtttta taggatgaat aggaattctt tccacgaagt    6780
tgcgttacaa aaagttgcat tcaaggctga aggaacatga gggtgcagag gcttaaaaca    6840
gccttgtgtg ttcagggagc tataagtaga agttcttaat ttaggagaac taaaccaagg    6900
ggaaaggagg ccaaggaacc acagttctta tccctttttct gttaataatt gggtttaaat    6960
gtcattaaaa taagttattt tgtccttttt agaaaagtaa taacatgcta ttataaaaaa    7020
aaagacttgt aggaatataa aatgtgtgtt ttacatgtat cctgttaatt gacttgcttt    7080
tattcagatt ttttgcagcc ctttctgttt accaggttat cttggagaca tatttattcc    7140
aaattccttt tttttttttt ttttgagatg gagtctcgct ctgtcgccca ggctggagtg    7200
cagtggcgct atcttggctc attgcaagct ccgcctcccg ggttcacgcc actctcctgc    7260
ctcagcctcc cgagtagctg gactacagg cgcccgccac cacgcccagc taatgttttt    7320
ttttttatat ttttagtagc gacagggttt caccgtgtta gccaggatgg tctcaatctc    7380
ctcacattgt gatccgcctg cctcggcctc ccaaagtgct gggattacag gcgtgagcca    7440
gcacgcctgg ccttccaaat tccttttaac agcctagcaa aagaataata aggaaggtaa    7500 atctgccccct acaagaaaat aatgcttcga cgatccggct ttccttcctg ctaccccag    7560 ccataagaat aaatgacctt gctcatcact gaaattttac ctgacctttg aattttaac    7620 tgcgtcagcc aaagaactta tattttgagt attcctaagg tgattgctat tgtagttttg    7680
aaacacttgg ttggtatgtt tgagggttttc atggtccaaa gttactatag cagttaaaag    7740
agtggactat caggtcagac ctattgggct ttaatcccag ttctgccttc tcttagacct    7800
tgggcctgtt gttttcactt ctctggtttt cagtttctct gtccacaatt gtggaaacga    7860
ggtccacttg tagagtaatt gagaggatga agcaagatga tgcatatcaa gtactttgca    7920
tagtgccggg cagacaggta acattcaagt gctaataatt actattatta ctatttattt    7980
tttgagacag gttctcactc tgtcacctag gctggagtgc agcggtgaga tcacagctca    8040
tgacagcctt gacctcctag gctcaagtga tcctcctgcc tcagccttcg gggtagctgg    8100
ggctacaggt gtgtgctacc accctcagct aattttctaa ttttttttgag tcaggatctc    8160 gtcacgttgc ctaggctgaa ttactcttat taaaaactat aatatcaggc cgagtgcggt    8220
ggctcacgcc tgtaatccca gcactttggg aggccaaggc gggtggatca cctgaggtca    8280
ggagttcaag accagcctgc caacagagt gagacccccc ccgtctctac taaaaatata    8340
aaaattagcc agtgtggtg gtgggcacct gtaatcccag ctactcggga ggctgaggca    8400
ggataatcgc ttgaacccgg gaggcggagg ttgcggtgaa ccgagatcgt gccactgcac    8460
tacagcctgg gtgacagagt gagactctgt ctcaaaaaaa ccgaaaaaca aaaagcataa    8520
ttagggtggt aacgcttata catagggca ggtggaataa aacataatta ggaggtcggg    8580
catggtggct cacgcctgta attccagcac tttgggaggc cgaggcgggt caggagttca    8640
agaccagcct gcccaacata gtgagacccc gtctctacta aaaatataaa atttagcctg    8700
ttgtggtggc gggtgcctgt agtcccagct acccggagg ctgaggcagg agaattgctt    8760
ttgaacccag gaggtggggg ttgcagtgag ctgagatcgc gccgctgcac tccagcctgg    8820
gagacagagc aagactccgt cacaaaaaca aaaaacaaaa aactgtcata tcaaaaacta    8880
aactaaaatg gtaatatctg ttagatatta caaagtcagg caaattatga ttcatggcag    8940
ccactaatga cccaaaggag agaaagaata attagcagat tctaacctaa tgggaaaaaa    9000
actaaatgaa tagggatggg ggacttacat tctgttagag gaaattgagg ctgtcatata    9060
```

```
aaaggaatag gtaaggcaaa ctgtaaattc ctgtttacac aaatgccctt ctgataaatc    9120
tctgcattgc ccacagtcca tgattacctc tcccttattt taagtaatat ttaacacatt    9180
aaaaatggat taccacccaa ggaattgctc ccgacccaga aagtgcaggt agtgttgaag    9240
gtttgagggg aagaggaatg attagagttg gttgtgtctc aggaagaagc caacaggagg    9300
aaccttattt tgagtcaggt aaagaaggtg ggagtgagga ggcatcccgg tggccaggta    9360
tgaagctggg agctgattgc tgcacattac tcagctgaat taaatgtgcc ctcacatctg    9420
tgtgtgtgcg tacatgcaaa tgtacatgtg tatgagttag ttggaggggt agacctttat    9480
tttcctgtcc tgtaactttc ctttgcaaac taatctgtat tcagaacagt gttgcagtta    9540
agaaccaccc agcttgtcca tgaaacaggt tctctcaccc catctcccca gttttagaga    9600
aggcaggaaa gaaaaggcag tgcttttctt ttttcctggc cgtatgcggg gcaggaagaa    9660
gccagcagag cttgaaagag aaagtaaacc ttctgggaaa taaacggctt ggcttcccta    9720
ttgtggagga ggagtgcaaa ttattagggg gatgtttggg tagttttgt agaagccatt    9780 tctgaaaact gatttggatt agtgaaggta agcccaattt aggaaaaccc tgcccagtct    9840
ggtgtcagcc acctgtttcc cgcttgtttt gattgatttg attagtttgt ggtattctga    9900
cctctcattt ttattacaag agttggaaga tttgagtctg aacttgagca cctgcttcgg    9960
tgaaagcttc ctaaaatgca tgttttttca cattttttct catgttcatt ttgttttgct    10020
ttttagcaaa cacttttct gacagaatct aaaagcatta gacttttctt gttttcccct    10080
tctctcccca caatgtaatc ttgaaaaccc aaatgttagc tgtgtaaatt acctctcccg    10140
taaaccaaac aaagtgcaat attgcattga gttagcattg aaatagtcgg cctttgaatt    10200
tttttctact tgtggtttag acataataaa tatttcatct cagactgact ttctcgacaa    10260
atcagttttg catttgggcc tcttttcatc agtatgttta gggaaagcac atttattgaa    10320
acattaacca aaatgaaaca taattaggag gccgggagcg atggctcacg cctgtaatcc    10380
cagcactttg ggagaccaag gcatgtggat tgcttgaggt caggagttca agaccatcct    10440
tgccgacttg gtgaaatcct gtttctactg aaaatacaaa aaactagctg ggtgtggtga    10500
cgcgtgcctg taatcccagc tactctggag gctaaagcaa gagaatcgct tgaacctggg    10560
aggcagaggt tgcagtgagt cgagatcgtg ccactgcact ccagcctggg caacagagac    10620
tccgtctcaa acaaccaaaa aaacaaaaac aagcataatt agggtggtaa cgcttataca    10680
taggggcagg tggaataatt gaagcattct ggagccagaa ataatcaact gattaagaat    10740
aatctggctg ggtgcggtgg ctcacgcctg taatcccagc tactcaggag gctgaggcag    10800
gagaatcgct tgaacctggg aggtggaggt tgcagtgagc cgagatcgcg ccattgcact    10860
ccagcctggg ctatgagca agactccatc tcaaaaaaaa aaaaaaaaa atcctgtttt    10920 ctgcagaaat atcccaggtg tcctgggtca gcagtgcccc atagattcca cggacgttta    10980
ccctaagttt tccaatggga gttcatacct ctatacccag tgagaatatt ttctgagtaa    11040
tgggaatgag attggagatg tagggtagag aagatccata cagtctttgg gttaaacttt    11100
ttcctctttg cctaggaaag attaatgcta atcttaacca cagatttgta gtaagaatgt    11160
atcagttttg tcattcagtt ctagactcca gttttcttta ttgtaatacc aatatttag    11220 agtaaatttt gaaatgaatc agtacaaaag atatgtagta agtggaaagt tagtccgcac    11280
cttatccttg ggactctttc ccagggacag ctagttacct actatttatc tctcctgagt    11340
tacttcatat gtatgcatgc aaacatgtta ttctctgggt gttgttcctt ccatatatag    11400
cagcaaatac accaaactct gtattttgct ttttgtcact ttatcttaga gaatactcaa    11460
```

-continued

```
tgcaaataca tgtgtatata cctcatgttt aaaaaatcta catagtaaaa ttagccaggc    11520
atggtagtgt gtgcctgtaa tcccagctac tcgggaggct gtggtgggag aatcacttga    11580
accctgagat cacaccactg gactccagcc tgggccacag agcaagattc tgtctcaaaa    11640
aacaaaaaca aaaacaaaaa aactacagag tagtattcta ggctatgcat atcataaatt    11700
tgatttccta atgataggca tagatgattt gcctgggcgg caaattagcg ttggctgtgt    11760
ctcaggaaga agccaacagg aggaacctta ttttgagtca ggttccaaag acagaaacat    11820
tgtctgacat ttgttttttgg gcttatatga ataaatctgt acacatatat ttttaatgtt    11880
ttaatcgtaa tatgtatact atttggaaat gtggcttttt agttaacaga gtgcatgttt    11940
taccccattg cacttaaaca ttaacttggg gataattaaa tgagtctgtc acttggacag    12000
gcaggaattg taccccccac aaacccataa accgccaatt ttttttttttt gagacagagc    12060 ctcattctgt tgcccaggct ggagtgcagt ggtgcgatct gggcccactg taagctcagc    12120
ctcccgggtt catgccattc tcctgcctca gcctcccaag tagctgggac tacaggcgcc    12180
cgtcacaatg cccggctaat ttttttgtatt tttagtagag tcggggtttc accatgttag    12240
ccaggatggt ctctatctcc tgaccttgtg atccgcccgc tttggcctcc caaagtgctg    12300
gaattacagg tgtgagccac cgcacctggc cggttttttt ttttttttttt gagatggagt    12360 cttgctctgt tgccaggctg gagtgcaatg gcatgatctc cgctcactgc aacctccacc    12420
tcccgggttc aagtgattct cctgcctcag cctcctgagt agctgggact acaggcgtgt    12480
gccaccacgc acagctaatt tttgtaattt tagtagagat gggggtttcat taataatcat    12540 taatattaga caactgtcag actcacagtg gtggatacaa actttctcaa attctgattt    12600
ttactctaaa gctcaaattt tatcattggc aacaaatatt gtcagttgct ttccctgaac    12660
agacagcttc ccttctttca tttttgagaa aatatctgcc agtatcccag ttggtttatc    12720
aatcattctt tctctttttt tttttgagac ggagtctcac tctgtcaccc aggctggagt    12780
gcagtggcat gatctcggct cactgcaacc tccacctccc aggttccagc aattctcctg    12840
cctcagcctc ccgagtagct gggattacag gggctagcag ccacacctgg ctaattttttg    12900 catttttagt agagacaggg ttttaccatg ttggccaggc tgatcttgaa ctcctgacct    12960
catgatatgc ccaccttggc ctcccaaagt gctgggatta caggtgtgag ccattgcgcc    13020
cggctctatt atttctttttc tttctttctt tttcttttttt tttttgaga tggagtttcg    13080 ctcttgttgc ccaggctgga gtgcaatggc gcgatctcgg ctcaccacaa cctccgcctc    13140
ccgaattcaa gtgattctct tgcctaagcc tcccgagtag ctgggattac aggcatgtgc    13200
caccacaccc gtctagtttt gtatttttat tagagatggg ggtttctcca tgttggtcag    13260
gctggtctcg aactcccaac ctcaggagat ctgcctgcct cagcctccca aagtactggg    13320
attacagttt tgagccacct gacccggttt gcttattatt tcttttaaat ttaaaaaata    13380
ataaataaag gggccatgag agcgaagagt ttgagaaagg ttggtctaaa ggttttaaca    13440
taagaatccc tgggttattt gcttaaaaag aagaaagaat ctatggatct gcctgagagg    13500
gtctgatgta gttatctgg ggtcatcctc acaggcatag cagatattct gattcagatg    13560
gtccttggtc cttagtttga gaaatgtggc tttacaaggc ccatagaata taaagtcttc    13620
tttggattag tgaagtcatg tccacagggt ttagaaaatg ttttgtttt agagataaag    13680 gtaagtggaa gagtagacat gtagtgaatg agggaaaatg ttttagagat ttcttttttat    13740 tctgtttact cttcttggta tgcacgtacc tgaatattaa ggatatttta tgaagtcatg    13800
acattaccag attaatgttg gttttgtttt aaggtacttt ctgactgctg gggttaattc    13860
```

```
ctacagacga ttctggtaaa gaatagcctt aagtttttaa aagtgttgac ttatttcaga   13920
tgtcttaata aagttaactt ccagttatta catgtaacgt atataaagct ctcatttttcc  13980
tttattctcg ttaattgttt gcataacaaa ttcaaaggga aatttgcttg gcagagatca   14040
gatagcagag atgagattta aaaacaggta atttggctac tagcctggga gtttgaagat   14100
tccaagtttg catccatgtg tagtcactta acatttctgt ccttatctgt aaatgggaat   14160
aacacctact tgatagggtt gttacattat cttggccacc tcaggttctc tttggctgag   14220
tgattgactg gaaaacgcaa tgtgaattca tgcttcagac tgggttcttt ttttttttttt  14280
tttttgagat ggagtttcac tcttattgcc caggctggag tgcaatggca cgatctcagc   14340
tcactgcaac ctctgcctcc caggttcaag cgattctcct gcctcaggct cccgagtagc   14400
tgggattaca ggcatgcacc accatgcctg gctaattttt ttgtattttt agtagagacg   14460
gggtttcact gtgttggtca gactggtttc aaactcctga cctcaggtga tccacctgct   14520
tcagtctccc aaagtgctgg gattacaggc atgagccacc gcacccagcc caggctaggt   14580
tctatatggg tgtgcttttt agaatttaga tcatgggcta tccccaacac aaactggata   14640
atgtttcttt ctagattctc tctaagcgtg tattctcttt ctttcctagg cacagccacc   14700
acttcactta cattgtggga ttataattc atgagtagtg gaatttcctt aaccttctct   14760
tgtgtgggag ctgaaggaca aaatgagata ttctctgaag agtggttaca tcatgcaaaa   14820
ctatgatgtg taatgaggtc acttagtttt ctaagtacat tatacatttt gataagattt   14880
tcatagaaaa gcttgtctcc ttggggagat cactcatctt ccatcttgac tattatttaa   14940
actttatggg tcagatttat cttttttaaaa acttaaccat aaagctcaat taattttttt   15000
tttttttttt tgagacggag tctcgctctg ttgcccaggc tggagtgtag tggcgcgatc   15060
tcggctcact gcaagctctg cctcccaggt tcatgccatt ctcctgcctc agcctcctga   15120
ctagatggga ctacaggcgc cgccacgat gcccggctaa ttttttgtat ttttagtaga   15180
gacggggttt caccgtgtta ggatggtctc gatctcctga cctcgtgatc cacccgcctc   15240
ggcctcccaa agtgctggga ttacaagcgt gagccaccgc gcccggctca attaatatat   15300
tttaaaaatt aatagacttt attattttta ttttattttta ttttgaggc agagtctcgc   15360
tctgtcaccc aggctgagtg cagtggtgtg atcttggctc actgcaaact ccacctcccg   15420
ggctcaagtg attctcctgc ctcagcctcc taagtagcta ggattacagg tgcctgccac   15480
catacccggc tagttttttgt aattttagta gatacgtgtt ttctttcttt tcttttcttt   15540
tttttgagat ggagtttcac tcttttgcc caggctggag tgcaatggca tgatctcggc   15600
tcactgcaac ctccgcctcc caggttcaag tgattctcct gcctcagcct cccaagtagc   15660
tgagattata gttgtctgcc accacgcctg gctaattttt tgtatgtttg atagagacag   15720
ggtttcacta tgttagccag gatgtctcga tctcttgacc tcgtgatccg cctgccttgg   15780
cctcccaaag tgctgggatt acaggcgtga gccactgcgg ccagtctaga ctttatttttt  15840
taaagcagtg ttagttttac agaaaaatta tgtggaaagt acagagagtt tccatatacc   15900
ccttacttc tcccacaact tctattatta acatcttgca ttagtatagt acgtcccttta  15960
caactaatga accaactcga tacattatta ttaaccaaat tcctgagtttt attttatttc   16020
tatttttatt ttattattat tattttttag aggtagggtc tcactgtgtt gtccaggcca   16080
ggttgcagtg gcatcatcat agcttgctat agcctgaaac tcctgggctc aagcaatcct   16140
cctgcctcag tctcccaaag tgttggaatt acaggtgtga gccactctgt ccagcctgaa   16200
gtccatagtt tacattacat ttcactctgt tgagcattct atggattttg acaaatgtgt   16260
```

```
gatgatgtat atttgccagt acacaattat ataaaatagt tttactgccc tagaaacccc    16320
ctgtgctcca cctattcatt cctctgctga accactggca accactgatc ttttataata    16380
tctccatagt tttgtctttt ccagaatgtc atatagttgg acatacagtg tgtagccttt    16440
tcagattggc ttctttcagt aaatgatatg catttcaggt ttcttcatgt tttttgtgg     16500
cttgataggt tgtttctttt cattggtgag taatactcta ttgtatggat ataccacatg    16560
ttgtttatca acattcacc tgaaggatag acatcttggt tgcttccaag tttgagcagt     16620
tatgaataaa gctgctataa acattccagt gcaggacttt tcacctcctc tggataaata    16680
tcaaggagtg caattgctag atcatatggt aagagtatgt ttagttttgt aagaagctat    16740
caaactatat tcaaagtgac tgtaccatta tacattccca tcagcagtga gtgagagttc    16800
ctgttactcc acatcttcac cagcatttag tggtgtcagt gttttggatt ttagccattt    16860
taatgggtgt ataatggtat acctattaaa attggttttt tttggagaca gagtttcaca    16920
gtttcactct tgttgccctg gctggagtgc aatggcgcaa tctcggctca ctgcagcctc    16980
cgcctcccag tttcaagtga ttctcctgcc tcagcctccc aagtagctgg gattacaggt    17040
gcacgccacc atgttctgct aattttttg tattttagta gagatggggt ttcactgtgt     17100
tacccaggct ggtcttgaac tcctgagctc aggtaatcca cctgcctcag cttcccaaag    17160
tgttaggatt acaggcatga gccaccgcac ctggcctcaa ttttttttt tttttttttg     17220
agacagagtt ttgctcctgt tgaccaggct ggagtgcagt ggcacaatct cggctcactg    17280
caacctccgc ctcctgagtt caagcgattc tcctgccaca gcctcctgag tagctgggat    17340
tataggcgcc cgccactacg cctggctaat ttttttttt ttttaatta gagacgaggt      17400
ttctccatgt tggtcaggct ggtcttgaac tccccgttct caggtgatcc gcctgcctca    17460
gcctcccaaa gtgctgagat tacaggtgtg agccaccgtg cccgcctgt tttggctttt     17520
actgtgaaga cgtgttagcc gctgtgatga ctagcaagtg tggccctcca cccagtcgct    17580
ctgggctccc agctcctgca tcctgctgca aacttgacat cttccctcaa gtaacttgta    17640
gttgtctcct gtctacttgc ccaaaatata actcttaaac ttttctctct gcaagtttgt    17700
gcctctctcc ctgtctgact tccccatcta aataaatggt agaccaccat ctactccttt    17760
gtgcaagcca gaaatctagg aatcatcctt aaattccctg ttctgtctta tctctgcttt    17820
cattcaaagc atcagcaaat cctgttggtt ctacctctga agttttctca aatactgtta    17880
cttgactcat cctgactttt gtttctgctt tatgttaggc taaatgccct gaaaactctt    17940
ttgtacaaaa cacctagaaa tactggataa actgggctta acagggaggc ccggtgtggt    18000
ggctcacgcc tgtaatccca gaactttggg aggccaaggt gggtggatca cctgaggtca    18060
ggagttccag accagcctgg ccaatacgta gtgaaacccc acctctacta aaaaaaaaa     18120
aaaaaattag ctgggtgttg tggtgcacac ctgtaggtgg tgcatgcttg aacttgggag    18180
gcggaggttg cagcgagctg agatcgcgcc actgcacttc agcctgggtg acagagcagg    18240
attctgtctc ttaaaaaaaa aaacaaaaaa agaaaaacag gaaaatcttc agaagcaaaa    18300
accaaacaat ctcaccaaag aaatgagaag atggctgggc gcggtggctc acgcctgtaa    18360
tcccagcact ttgggaggcc gaggcgggca gatcacccga gatgggcaga tcacccgagg    18420
tcaggaattc gagaccagcc tggccaatat ggtgaaaccc cgtctctgct aaaaatacaa    18480
aaattagcca ggtgtggtgg caggcgcctg taatcccagc tactcaggag gctgaggcag    18540
gagaatcgct tgaacctggg aggcggaggt tgcagtgagc cgagatcatg ccactgtact    18600
ctagcctgga cgacagagca agactctgtc tcaaaaaaaa aaaggctggg gtgtggtggc    18660
```

```
tcatgcctat aatcctagca ctttgggagg ccaaggtggg cggatcactt gaggccaggt    18720
gaacatggcg aaaccccatc tctactaaaa atactaaagt tagctgggca tggtggtggg    18780
tgcctgtaat cccagctact cgggaggcga ggcaggagaa tcgcttgaac caggaggtgg    18840
aggttacagt gaaccgagat ctcgccaccg cactctagtc tgggcgacag agcaagactc    18900
cgtctcaaaa aacaacaaca aaaaaccaac acatggccaa agtgcagtga cttacatctg    18960
tataatccca atgttttggg aggctgaggc aggaggatcg cttgagtcca ggaatttgag    19020
accagcctgg gcaacataga cctcatcacc aaaaaaaaaa tatttttttaa ttagctgggt    19080 ttggcagcat gtacctgtag tcctagctac tcaggaggct gaggtgggag gatcacttag    19140
gcccaggagt ttgatagttc gaggttatag tgagctatga tcctgccact gcactccagc    19200
ctgggccaca gagtgagacc ctgtctctta gaaacaaaac aaaacaaaaa aagaaactg    19260 aattaaaaac aacaagaaca aaaatgctgc tttttgttat tgagttgtag cccaagtttc    19320
ttgagggtaa agcattgaaa agcaggcagt aatagatttg ctgtttaaag agatttactt    19380
gcagcactat tcacaatagc aaagacatgg aatcaaccta aatgcccatc agtgacaaat    19440
tggataaaga aaatgtggta catacactgt ggaatactat gcagccataa aaaacaacga    19500
gatcatgttt ttgtttgttt gtttgtttgt ttgttttttga gatggagtct tgctctattg    19560
cccaggctgg aatgcaggtg gcacgatttc agctcactgc aacctccgcc tcccaggttc    19620
aagcaattct ctgcctcagc ctcccgagta gctgggatta caggtgccct ccaccatgcc    19680
tggctaattt ttgtatttct agtagagatg gggtttcacc gtgttgggca ggctgttctt    19740
gaactcctga cctcatgatc ctcccacctc ggcctcccaa agtgccggga ttacgtgtga    19800
gccaccgtgc tcggctgaga tcatgttttt gcaggaacat ggatggagct ggaggctatt    19860
atccttagca aagtaatgca ggaacagaaa accgaagacc acgtgttctc acttataagt    19920
gggagctaaa tgataaggac ttgtgaacac aaagaaggaa accacagata ctggggttta    19980
cttgagggtg gagagtggga ggagggagag gaacagaaaa gataactatt gggtattggg    20040
cttaatactt aatattttat caaaataagc tgtacaacaa acccctctga catgagttta    20100
cctatataac aaacttgcac gtgtaacccc aaacctaaaa taaaagttaa aaaaaaaaa    20160 aaaggctggt tgcattggga ggctgaggca ggcagagcac ttgaggccag gaattcgaga    20220
ccagcttggc taacgtggag aaaccctgtc tctactaaaa attcaaaaat tagccaggtg    20280
tggtggtgca tgcctgcagt cccagctacc agggaggctg aggcaggaga attgcttgaa    20340
ctcaggaggc agaggttgca gtgagctgag attgcaccac tgcattccag cctgggcgac    20400
agggcgagac cttgtctcaa aaaacaaaac aaaacaaaac aaaacctgt cactttggga    20460 atatctcaaa cctagtcatc caagtggttg tacgatttta gtgtctgcat atcaatattt    20520
agtgtgatct actttcttag attctcaaat actgccaatg ggcacatgtc atgaaataat    20580
gtcttttaga ggacaagaga gtgctaaagt ctcattattg cagtttaaga aaaacaattc    20640
tgtaacagtt taactttata ggaaatgcct tttgtttatt tatttttttt cttttgaggc    20700
ttagattttt attttatgt ttttagagat ggggtcttcc tatgttaccc aggctggcct    20760
tgaattcctg ggctcaagtg atcttcctgc ttcagcctcc tgagtagctg gactagacg    20820 tccactactg ctcctggctg gaagtttaga ttttaattta aactcttcta ttgggaaact    20880
ttgtatgttt gctttaccac ttaacatttg catgcattat tgtacctatt gtctcctact    20940
taaggaaggg cagtttatgc tgttatatga agtgaattaa cctccatgg tacttcagtt    21000 ttctctatgc taaaagtgtg ttctagattt ttgaaaaact tacttaattt tcattcattt    21060
```

```
attcaaatat ttgagcattc tgtagttgct ggggaaatag cagtgaactg aagaatgtct   21120
ttgttcttat ggggcttaag ttcctagttg atcatattgg aaggagatac atgaaaaaag   21180
aaatatatga acaatggagg gcgatgagta ctgtaaagga gaattcagca ggggagatgt   21240
tgctgtttta gatagagggg tgtcaagaga cattgtgcag agacctgaac gaagtgaggg   21300
agcaagccat ggagatatct agggaaagag cctatcaggt ggagagaaga gtcctagggc   21360
agaaacgggc aaggtgtgtt ccaggagcag agagggaca gctgtgagca aggggagagt   21420
tgtagggaag gaggcaaaga gagacatctg gggcaaaatg gattgactgg tgggccgtgg   21480
taggactttg gatttttttcc tgagtgggtt ttgagcaggg gaatgaaatg atctgactct   21540 ggttttttttt tttttttggag acaaaatctt gctctgttgc cgaggctgaa gtgcagtggc   21600
gcaatctcgg ctcattgcaa catctacttc ctgggttcaa gctatgctcc tgcctcagcc   21660
tcccgagtag ctaggattac aggcttgggc caccatgccg gcgaatttct gttttattt   21720 ttatttttta tttatttta tgtttatgtt ttttgagacg gagtctcgct gtgtcaccca   21780
ggctggagtg cagtggcgcg atctcagctc actgcaacct ctgcctcccc ggttcaagca   21840
acttctcctg cctcagcctc ccgagtagct gagattacag gcgcctgcca ctacacctgg   21900 ctaattttg tatttttagt agaaacggga tttcaccttg ttggccaggc tggtctcgaa   21960
ctcctgacct taatttatct gctcgccttg gcctcccaaa gtgctgggat gacaggtttg   22020
agccaccgtg ccagccagga ctcttatttt gaaaggatct gtaatgtgga aatagaagg   22080 tagagggaca aggatgaaag catccaggcc agttagccta gtccagctat ctaggtaaga   22140
gatgctggtg gcctggatta aggctgcgtc agtgggaggt tgtgagaaag gctcaccttc   22200
cttttttttt tttttttttt tttttgagac aggatcttac tctgtctccc aggctggagt   22260
gcagtggtgc aatctcagct tactacaacc tccgcctcct gggctcaagt gatacccca   22320 cctcagcctc ccaagtagct gggatcacag gcttgcgcca ctatatccgg ctaattttg   22380 tatatttcgt agagacaggg ttttgccatg ttgcctaggc tggtctcaaa ctcctgagct   22440
caagtgatcc acccgcctca gcctcctaaa gtgctgggat tataggcctg agccattgtg   22500
cccggtcact tccagatttt gaagacagag ccaacaggat ttgttaatgg attaggtgtg   22560
gcaggaggag ggggaggaag agagagagag actggagttg aagttaaggc tcatttcaag   22620 gttttttagcc tcaacatgtg caggaatgga gttgtcactt gctagaatgg gggagactgg   22680
aggagaagcc ggctgggaga ggtttttaat gaaggggttg gctttggata cattaagttt   22740
gacatgcatt ttagacatcc aggtggagat attgaagagg cagttggcta taagtgtctg   22800
atgttcatat tagcggatgg ggctagagac ataaatttga gaattgtcag tgtataaacg   22860
ttgttttgaa agaaagtggg gctgaataat ttagaaagga gtgcatagag aaaataagtt   22920
tactattaaa atagctttaa caggccgggc acggtggctc atgcctgtaa tcccagcact   22980
ttgggaggct ggggtgggca gatcaaaagg tcaggagttt gagaccagcc tggccaatat   23040
ggtgaaaccc tgtctctact gaaaatacaa aaattagcca ggcgttgtac cgggcacctg   23100
tagtcccagc tacttgggag gttgaggcag gagaatcact tcaacccggg aggtggaggt   23160
tgcagtgagc caagatcacg ccactgcact ccatcctggg caacagagca agactccgtc   23220
tcaaaaaaaa aaacaaaaaa aaacaaaaaa aaaaactttt aacagcaaag cctcttcctt   23280
taaaattatg aattttttc ttatggaagt tggactcttt cattattaag tctacattca   23340
atcactatgt tagtaaaaat gttgttctag ttgccgaatg caataaacca gctcagactt   23400
agtggcctaa agcagcaatc atttgactat gttcgaagat gccgtgggca ggaatttaga   23460
```

```
taacagcagg gatggcttgt ctttgctctg cgatgtctga ggtctcactg agaaaactca   23520
agcggctggg ggtaataatc atctggaatt ttctttactc ctgtatctga tgtctgggct   23580
gcgatgactc aaaggctgat ttcagctgag actgtagacc acgtgcctac ttgtggcctc   23640
cccttttgcc ttgggtttct cacagaatgt ggctggttct ggagaatgag acttccaatg   23700
aaatcaggtg gaaatgacat ctcgccgctt tcagcatgct ctattggttg aacagttat    23760 ggacttagct agattcaaag gaagggaaca aagacccct cctctcagag agtgggcat    23820 aatgagagaa tttagggcca tgttatccaa ccaccacaaa tgccttctga atttgaggtt   23880
ctgcctcaaa agttcatagt tcctttgact gaaggacttc tatatatcca agcatcgtca   23940
gccccaggta tattgttcca tgtaagtgac caggactacc ttagtatttc gtatagggaa   24000
agtgacctga ataaatttga gaaaagaatc ttccttctct ccagtaagca ctgaggtaag   24060
cattgagcca tattataggt ttatgacttt gagactcaga aatttaaatt cttggccagg   24120
cgcagtggct cacgcctgta accccaacac tttgggaggc caaggcaggc agatcacttg   24180
aggtcaggag tttgagacca acctggccaa aatggtgaaa ctccatctct acgaaaaata   24240
caaaaattag ccaggtgtgg tggcgggcac ctgtaatccc agctacttgg gaggctgagg   24300
taagagaatg gcttaagttc tctttatctg ctttatttca gttgcctctc ttagatgaat   24360
attaatgact tacatagcat tttagatcag tggatgtttt tgtgattctt ttatttgagc   24420
tttggccaaa gataacagta cccacaggtt ttttccagct actcgctctt ctcccttcag   24480
tggccctcga gcctggaaaa tctgacatga caatgtgctt gctcaaccta ccactgtttt   24540
tcttttgaaa agtttggcag cctgtttctg actcctatga aggtgaattc ctcagcattc   24600
acagtttatt agaaaaatac tttgcttctc tccaaactcg aaattcaaga taaccaaacc   24660
tatatatagg ctgatctttc aggatgcagt tgtcatgttg atgccatgct tttcagtatc   24720
gtggccatca tctgttcagt aggggaggtg tacttctgta atgggaggtg gtggttatgt   24780
gtgtgtgcaa gtgtttattt ggtgtcttaa gttagcctgt gggaagttct aaatcaggat   24840
ggtacgtggt tgccagcaga gagctgctcc tcaagtgaag gaggtagaat caaagccaat   24900
aggaaagagc ctcagatgct tatatatgta ccgtggggat tcagagtgaa agcagtcatt   24960
ggactagggg tggggttagg gagagcctgt ctgacagaca caagaaaggg atggataacg   25020
ccacccagag aaaaaagcat tttaggcaag aacaaatatg aaaaaggaac aaagtctgtg   25080 ggtgggggc aaggaggaga taagttgact tgaaggaaga caacacttat gaaagtcacc    25140
tggaggctgg gtgccatggc tcatgcctat aatcgcagca cttgggagg ccgaggtagg    25200 aggacaactt gagcccagga gttcgagacc atcctgggca acatggtgag actgagtctc   25260
taccaaaaaa aaaaaaaaaa gaaaattatc cagacatggt ggcatgtgcc tgtaatccca   25320
gttactcagg aggctgaggt gggagggttg cttgagccca ggaggttgag gctgcagtga   25380
gctgtgatcg tattattgca ctccagcctg ggtaacagag caagaccctg tctcaaaaaa   25440
tgaaagtcat ctgtaggctg gagagaggaa ctggaagggg ctaaagttgg ctgagtagtt   25500
acagagcctg agataaggt aaagatttg cattggacaa tgatgtta gtgtgtgttt       25560 ttgagctggg gagtgctgtg attttactct tattgaagaa tcactgaagg attattcttg   25620
aatcagtgat tcttgatcat tcttgaattt ttcaaacagc aaaactggaa gagttggcct   25680
attcctcaga atatttctta attgggcgca gtgtcctcac ttgggagaac ctggctacac   25740
actttagttg taattcactc cagtcgttca ttcattcaat acctattttt tcagcaccta   25800
ttatgagcca gacactatgc tggatgccag ggttcagggt aggacacgct agtgagcaaa   25860
```

```
agccaagact cttcttgtct tcatggggct ttcagtccag catagtggtt atgagtccaa   25920
gttaatggag tcacagtact tgggtgcaag tcatggtgat ggtgatagaa ggaaggcatg   25980
tgtgagggcc agtggcaggc aggagcctgg tgttttttgag gacctgaaga aggagcagag   26040
tgagtgccag gaacttagcc accagctggt accagcccata cgagaggggc agagccagcc   26100
aggatgtcgg tcatgctagt aatgagtaca aacacttaca tgctgcacgc tattgggctc   26160
ctgagtgcta cgtgttcatt agctcgatga atttgtacag caaccctgtg aggtaagcac   26220
tgttctctcc cctttctata gatgaggaaa ttaaggcaca agaggataa ataactggca   26280 ccagctacac gctaagtgat cgaagtggtg gaaccaggat tcaaatccat gctattctgc   26340
cttaagataa caaatcttgt tttttagcct aagaacagag cagtcatcag gagggtttta   26400
agtaggggtg tggcaagatc aagtttgtgt cttgaaaagg tctctctacc cacagtgtgg   26460
aaaatggcct ggaggcaagc acacagatgt tgggagacag ttaacagctc ttgccatggc   26520
cccctatgca ttttggctct gatgtttctg cctgattttt ctcttgcctc tgcctctttt   26580
cctgagggga tggcaggttt taccattcag ctggagtaca aaccctgaac ccttttttggt  26640 taaatatcta cttgcttttc ctacagtatt attttgagtt gctgtggctg taatgtcttg   26700
agggaatcga gcttgacagt aatttataga acaaacagtt tttagagact gtgtggccca   26760
attgccctct caatgttggc actcctgcca tgacatttac catgctgagc atgtgaccgc   26820
catctgaata ccaaatgcca caggaacctg ggaggttgtc acttactcct cccttttctct  26880 gagtcacctt tgcccttcag tcagtcacca agtcccatca catgtagctc tgtaatgtca   26940
cagaagatgg atgtctgcct caaaacactt acaatgctgc tacctaaatt gggcagccac   27000
gacctcccac caggattatt gcagcctgag ggatcttttt gaaatgtaaa tcaaactatc   27060
acttgtctgt ttaaagcttt tcaaagactt accccattgc ccttggaaga aagtgcagat   27120
atcttgacag gagagccttc tccagcctcc tcttctgccg tggtctcctt gtacagtctc   27180
tacagtgtac tgcttcatta gaaccctgga gattattatt tgctagttct gggctaagaa   27240
ctggcacctg gctttgtaga gctcctcagg agattctgag gcgtattcag agttgagccc   27300
tgatctctgc tctgatttcg aggttctcgt tatatttatt aatgatcacg aaaaaattta   27360
ttattattct ttggcctcac tttagcatca tctgaggaat tttttttttt ttttgacaga   27420
gttttgctct tgttgcccag gctggagtgc aatggcgtga tctcagctca ctgcaacctc   27480
cgcctcccgg gttcaagaga ttctcctgcc tcagcctccc aagtagctga aattacaggc   27540
atccaccacc atgcctgcta atgttttttgt attttttagt agaggtgggc tttcacagtg   27600
ttggtcaggc tggttttgaa ctcctgacgt cagctgatcc acccacctag gccccccaga   27660
gtgctgggat tacaggtgtg agccaccgtg cccagccgta gctttcgaaa tttgaaacct   27720
ggtcccactg tcagaggttc caatttggca ctggtttggt tcccaggcat ctttcttgct   27780
gtatatattt tttagtgtca gccagggtgg agacctctgt attacttcat ggggaagaat   27840
ttgggagaag atgttgtgag gagacaggtt ctagtcctag agtgatttat cctttctcgt   27900
acagatttcc aggtatttga ggggccactc ttctgtaatt catgttttttc tctcctaacc   27960 tcactcctgt tgcctgcatc ttcttgctga gcaaaatatt caaggtcttc aactcctcac   28020
accctggttg tccctccctg gatgtgtttg gttgtttttag tgttccattt caattttgat   28080
acacagaatt agaatagcat ccagatgtgg gtctgttaca gctagactac tagatccttc   28140
aaaatccaag tactagtatg tctattaaaa taccataaga tcacattggc tagttacaat   28200
ggttggtttg tgggttactt aaaaatcaac taaaattctt tttttttttt tgagatggag   28260
```

```
ttttgctctt gttgcctagg ctggaatgca atgacacaat cttggctcac tgccacctct    28320
gcctcccagg ttcaagcaat tccctgcct tagcctcctg agtagctggg attacaggca    28380
tgtgccacca tggccagcta attctgtatt tttagtagag atgaggtttt ccatgttgg    28440
tcaggctggt ctcgaactcc cgacctcagg tgatccacct gcctcagcct cccaaagtgc    28500
tgggattaca ggcgtgagcc actgagcctg gccaaaattc ccactttcta atactcctgt    28560
agtagctggg tacggtgggt cacatctgta atcccagcac ttttggaggc tgaggctgga    28620
ggatcgcttg agcctaggag ttcgagacca gcctgggcaa gatggccaga cgccatctct    28680
aatttaaaaa aaagaaaaaa caagactcct atagtggtga agaacagaca ttccgaaaac    28740
agactgtgcg ttatgattcc agctccatgc ctttactacc tgtgttgtga ctttggataa    28800
atcacttaaa aatctttttt tttttttttt tttttgaga cggagtcttg ctctgccgcc    28860
caggctggag tgcagtggcg cgatctcggc tcactgcaag ctctgcctcc caggttcaca    28920
ccattctcct gcctcagcct cccaagtagc tgggactgca ggtgcccgcc actacacctg    28980
gctaattttt tgtattttta gtagagacgg ggtttcaccg tgttagccag gatggtctcg    29040
atctcctgtc ctcgtgatcc acccgcctca gcctctcaaa gtgttgggat tacaggcgtg    29100
agccaccgca cccggccaaa tcacttaaaa ttctgtgcct cagtttctcc tctgtaaagt    29160
gggataaaaa tagtacctat ctgatagggt tgttacaatt atgaaatgag caaataagta    29220
tgtcaagtgt ttaaaacagc gcctggcttc ttgtaaaaag tgctatataa atcatagcta    29280
taatcattac ttatttcgac tgctctttaa ccaaggttct tattttttcat cttttttcttt    29340
tgttttgaat atcacttagt gttttcacct tttactcttt ttaggaccta gagccatcct    29400
aggtgaaata cgtatggaga tatttgatca ggtcaccacc cagctctcct gacctccctt    29460
ctctccttaa attaacatgc caaatcacag catcactgac tccttccctc ccgatatgat    29520
aagagtgtgc attgaaatgc atgtatttta cttagcaggg aaagctgatt agtgattatc    29580
acacttaacc cctagtgaat ctgatggatt aacctgcttt ccaggacact aaggaaatgg    29640
gtttaagata agaaatatct ggctgggtgc ggtggcttta cgcctgtaat cccagcactt    29700
tgggaggccg aggtgggcag atcacgaggt caggtgattg agatcatcct ggctaacacg    29760
atgaaacccc ctctttacta aaaatacaaa aaattagccg ggtgtggtgg cgggcgcctg    29820
gagtcccagc tactcgggag gctgaggcaa gagaatggtg tgaacccagg aggcagagct    29880
tgcagtgagc tgagattgtg cccaccgcat tccagcctgg gcaacagagt gagactacat    29940
ctcaaaaaaa aaaaaaaaaa aagtaagaaa tgtccatgaa agggagaccc tgggggaaag    30000
gaacaataac tgcagctctg aggatctggc accagcagca ccagcacaga gggatgctgt    30060
acaaccatta ttgattttaa ctttacaaca gttcttcaaa ggagagagag ttccctgttt    30120
tactgaagag aaagcccatt tggtagtgaa ataccattcc caaagacaaa tagctaataa    30180
atgtcaggca gggttttgca cccaggccca tccagctccc gtctctactg tcctttcccc    30240
cacaccacac tgatacagag gaatgtgtct ggttgggaa gtggaagtgt tcccaagtgg    30300
ggaggtcatc tgatgcacaa atttggtctg ttttgtgggt tttcttgttt tagttttagt    30360
ttttgtagag ctcagacctg ttcttaggca gctttaacaa tcaactgtgc actcagtaat    30420
tgacaaatca tgtttgttac ttttaattta gagggaatta ggtttgttaa gctcttgctc    30480
cttctttaga gatggggtct agctctgtca cccaggctgg agcgcagtgg tatgatcaca    30540
gctcactgca gtctcaatct gctcaagtga tcctcctgcc tcagcctcca tgggactaca    30600
agcatgggcc accatgctag gctaattttta aaaaattttt tttgtagagg caaggtctca    30660
```

```
cggtgttgcc caggctggtc ttgaactcct gagctcaagc aatccctctt ccaccttggc   30720
ctctcaaagt gctagaatta taggcatgag ccaccatgcc tggcctttac ttctttcata   30780
tattcaaatt ttgtcatatt agtagggaac tataactcaa gttttcttat agattgatgt   30840
tcatttttac aagcttgatc gtcattggtt tttaatttta aagcaaatcc tgttatatgt   30900
aattgaacat tacagtaatt atagtaattt gtttcagatt gggcactcaa gtgttaatat   30960
tttgtctctt taggaaatca aaactagatt tatatataga cttcttattg caagtatcta   31020
gtcttaaatc ttacaaaggt actatttgga cttaaaacta tgaaattgtg tgcttactat   31080
ataagtgtac ttattttgag ttatgtttta aacttgaaat tccattctta atgtctagag   31140
taattatgaa tggttaaatt atgaatgact ctaatagttt aaagctacag tatttattta   31200
tttatttatt taatttattt tttgagatgg agtttcgctc ttgtcgccca ggctggagtg   31260
tagtggcacc atcttggttc actgcaacct ctgcctcgcg ggttcaagtg attctcctgc   31320
ctcagcctcc caagtggctg ggattacagg tgtatttcac catgcctggc taattttgt    31380
attttagta gagacaggct tttgccatgt tagcctggct ggtctcgaac tcctgacctc    31440
aggtgaccta ccctcctcag cctcccaagg attacaagca tgagccacca cacctggcct   31500
acagtatttt aatgtggact ctctgtcatc cattatgctg tttatcctgt ggtgaaaatt   31560
ttatgaagat tgaatgtttt tctctagcgt gaattgcttt ctcttacttt tctcattttt   31620
ttccttccta atctacttgc agatacttca gattattttt agaacgtggt atggtgagaa   31680
caaataaatt gggggtttcca aatcttaata aattatgtgg ccctcagtgg gattagcagg   31740
gttgtattga aacaccaat agaaacaaaa tagttctttt atgcgcttta aataaaaatt    31800
tcttttcagg ccaggcgcag tggctcacac ctgtaatccc agcacctggg aggctgagg    31860
caggcagatc acctcaggtc aggagtttaa gacaagcctg gccaacatgg tgaagcgccg   31920
tctctactaa aaatacaaaa attagccggg tatgatggcg catgcctgta atcccagcta   31980
ctccagaggc tgaggcatga gaatcacttg aactcaggag atggaggttg cagtgagctg   32040
agatggtgcc actgcactct agcctgggca acagagtgag attctgtctc aaacaacaac   32100
aacaacaata acaaaacatc tcttttcagg ccaggtactg tggctcacgc ctgtaatccc   32160
agcactttgg gaggccaaaa caggagggtc gcttgagacc aggagtttga gaccagcttg   32220
ggcagctggt ctctatttga acaaacaaac aaacaaacac aatactcttt tcatagaaaa   32280
atgtttacta cacaataaac tttaaagaa tatgcagctg tattaatgct atgactccaa    32340
tgtaaaaaaa aaaaaatata tatatatata tacacacaca caaacacatt ctgaaataga   32400
tttaaaggaa ttacatcaac atgtcaattt ttattttttc ggagacaggg tctcgctgtg   32460
tcacccaagc tggagtacag tggtgcaatc acagctcact gcagccttga cttcctggcc   32520
tcaagtgatc ctccccctc agcctcccaa agtgctgggg tcacagacca ccacacctgg    32580
caacatgtca gttttgttc tgcatagtgg atggtggga tatggatgtt tttatctttt     32640
attttctttt ttatatttt ctaaatttttc cacattgaac attatttat aatctttcaa    32700
acatatctct taaaggact ggttcctata gaattcagtg caagaaatct tctgtgtttc    32760
tttatacttt ggttgccttg atcactgggc ctttcctgac agcaaagaag aggttagtgt   32820
aggcagcaga taaacacag gtatgctcta tttaaaatgc atgtatttat aataaaagta   32880
taggtggtac ccaaaggaaa atgtcatgac acattgcaaa gtggaacaga agttatcttt   32940
agatcacttt ctgttctgga ttattgtatg agcctgattt tcgtctctct ttccgccttc   33000
cctcacccctc gttgtaaatc cactagtgca tggatgtgaa gtacaagtct taactttaaa  33060
```

```
aagttttatg aagctgtgta gtaaatccct tttgtaagtg gtcttgactg cgtttctcaa   33120
tatatctttt ggtttcatta gattcaagta tataaatgag aactgtaact ttggacagac   33180
tttttcagtc atctttacgg taataagttc ccaattagac aatagttatt tgttttatga   33240
cttgctgttg gtaggttatc cccaagggac tgagaaattc ctgttttgaa aagtccaaaa   33300
agtctttgat gacttgctgt ttcatttttt tcttttctct tcagttatag aaaacaggat   33360
tacacccacc ttgcctttgt acagtgcatc tactatctgc tgacttaacc tgagtaaatg   33420
ctttgaattg agccccatat aatgtcctaa ggcagcctat atggagtaat gaattgtctt   33480
ctctcttatg cacccagagt ggtagttggc actcaagttg ttcctcagat aactttgtgt   33540 gttctgggc tcaatgaagt agttattaag tcacaggctt ggggagaaca ttcatcctat    33600
ggcattgaat gaagtgttgc ccaattctag aatgtctaat aaaatttttt taaaaaccca   33660
caggcttaga attattccgt agatatgaag taatgtagtt agaacttagt ggagttcttt   33720
agattaactt gtaatttgaa aaaccaaaat tgaaattgtg aaataacatg gctctttga    33780 ggtcttttcc agtaaaacag ttacagtaaa gctgcttggc agtgattttc ctagacactt   33840
tggctagtca tctcctgtga ctgctgttaa ttaaatatgg tttgtagcta agcagcctgt   33900
aaggagaaga ctatggaagt atttgcatat tctctccttg aaaatactac ctggtctttg   33960
gctttaagtt atacttttat tttccctgt agaataacta ttaaagtatt acctatggtg    34020
attagactaa gaagtaaaac atgaaatcag tcattgttgg tgccctggtg ccttcttttt   34080
tttttttttg agacagagtc tcactctgtt gcccaggctg gagtgcaatg gcacgatctt   34140
ggctcactgc aacctctgcc tcccaggttc aagcgattct cctgcctcag cctcccaagt   34200
agctgagact acaggcgccc accaccacgc ctggctaatt tttgaatttt tagtagagac   34260
agggtttcac tatattggct aggctggtct caaactcctg accttgtgat ccgcccacct   34320
cagcctccca agtgctggg attataggtg ttagccactg tgcccagcct ggtgctttaa    34380
ttttatggaa aaaactacta gctggtttct gttttaagaa ataacacagg ccgggtgcca   34440
tgacttgcgc ttgtactccc agcagtttgg gaggccgagg cgggcggatc acgaggtcag   34500
gagtttgaga ccagcctggc caacatagtg aaacccgtc tctactaaaa atacaaaat     34560 tagccgggcg tggtggggca tgcctgtagt cccagctact cgggaggctg aggcaggaga   34620
atcgcttgaa cctgggaggt ggaggctgca gtgagccaag atcgcccac tgcacaccag    34680 cccgggtgac agtatttcat ctcaaaaaaa aaaaaaaaa aaagaacaca attattgtac    34740
tacttactag ccctcctctg tccccagcta aaaataagaa cagcaacaac caaaaaatcc   34800
ttagttatgt actggaaatg aattagataa ttttcaataa cttacacgtt tttaggatat   34860
gttagtttga aaatgcaaat attcatgcat gaccccagtg ttaatctatg atggagcagg   34920
tatagtggga tgctgtttca tgatttaatt tggaccttca gggagtagac tgtgatgcct   34980
ctgcatttgt atccaagaca aataattaaa tagtctattt ttggctgggc atgatgcctc   35040
atgcctgcag tcccagcact tgggaggct gaggtgggag gatcgcttga ggccaggagt    35100
tcaagatcag tctgggcaac aaaatgagac cttgtctcta caaaactac aaaaaattag    35160 ctgaacattg tggcttgtgc ccctagtccc agctactcag gtccctgagt taggaggatt   35220
gcttgagccc aggagttgga ggttacagtg atctatattt gccactgcac tccagcctgg   35280
gtgacagaga gagaccctgt ctcaaaaaat aaagtctgtt tttaaaatta attttaaaca   35340
ctggagttta ttacaaaaag cagttggttc ttttttttaaa tcattttttt ttaggagaac  35400
caccgctttt tggctacatt gtctagagta gcagtgttca ataaaaataa gatccaagtc   35460
```

```
acatatgtaa tgttaagttt tcttttagtt tcttttctt ttcttttctt ttctcttctt    35520
tctttctttc tttctttttt ttttttttga tatgcagtct cactctgttg cccaggctgg    35580
agtgcagtgg cacgatctcg gcccactgca acctccgcct cccgggttca agcaattctc    35640
ctgcctcagc ctcccgagta gctgggacta caggcatgtg ccaccatacc cagctaattt    35700
ttgtattttt agtagagatg gagctttgcc atgttggcca gtctggtctc aaactcctga    35760
cctcgggtga tccacatgct ttggcctccc aagtgctgg gattacaggc atgagccacc     35820
atgccctacc aatgttaagt tttctagtag ccatattaaa agaagtaaaa agaaatgggt    35880
gaagttaatt ttaataatat attttattta acccaatata tctaaaatat tatcatttca    35940
acatgaacaa gatacttac attcttttgt ttttcactaa gtcctcaaaa tccagtgtgt     36000
attttatatt gacagcatag ttcagtttga agcagccaca tttcaagtgc tcagtagcca    36060
catgtggcta gtgactccat actggactgt gtaggtttag agtttcagta aatttgtatg    36120
caatagaatc tacataaatt ggcatattat gcagatttct ttgtatgcac atcagttctt    36180
gcatagcata agtcaggtca tgatgctttt agtctatgag gcagattttt tttttttttt    36240
ttttgagaca gagtctcact tggtcaccca ggctggagtg tagatgcaca atcttggctc    36300
actgcaacct ccatgtgagg cagattttaa cttggcccta atgcaaatat tgtaagagag    36360
atctaatggc ctttgatttc ttacagaggg caatcaatac atgccatggt tacaatgctt    36420
cagcatatag tatgcacgtc agccactgct tttactctgg ctagtgctta gtgtacctgt    36480
accactgccc aggcagcatt tgtcctgtgg caggtgaatc ttagggtgga aggtggcaag    36540
taacattgct tttttttgag agggagtctt gctgtattgc ccaggctgga gtgcagtggt    36600
gcgatctcgg ctcactacaa cctccacctc ccgggttcaa gtgattctcc tgcctcagcc    36660
tcctgagtag ctgggattac agacggccac caccatgctc ggctaatttt tgtatttta     36720
gtagagacgg ggtttcacta tgttggccag gctggtctcg aactcctgac ctcgtgatcc    36780
acccgcctcg gcctcccaaa gttctgggat tacaggtgtg agccaccgtg cccagcctac    36840
atttttaaat taattaatta taagcaggat ctcactgtgt tggccagact ggtcttgaac    36900
tgataagagt tcaagaccag cctaggcaac atggtaaaac cctgtctact aaaaaataca    36960
aaaaaaaaaa ttagctgggc atggtggtgc gtgcctataa tcccagctac ttgggaggct    37020
gaggcaggaa aatcgcttga acccgggaga ctgaagttgc agtgaggtga gattgcacca    37080
ctgcactcca gcctaggcga ttccatctca aaaacaataa caacaaaata acattgttgg    37140
aatatttagt taatttatag aagcgtattg gcctaattgg ggcaaatacc ttattctgac    37200
attctctcta tttgctttac tgagcttttt caccagtgga atttaagccc ttgatacatg    37260
aggagggaaa ataccttgga gctgtgctgc acatgtaaag tacacaggag atttagaaaa    37320
cttcgtagca aaaaaagag tgtaaagtat ctcattaata gttttgtgg gctggacacg      37380
gtggctcaag cctatactct tggcacattg ggaggctgag atgcatgagt ctaggagttt    37440
gagaccagcc tggcaacac agtaggaccc cgtctctaca aaaataatca gccagatgtg     37500
gtgcgcatct gtagtcccag ttacttgaga ggctgaggtg ggaggatcgt ttgagctggg    37560
aagttgaggc tacagtgagc tgtgattgaa ccactgcact ccagcctggg tgacagagtg    37620
cctgtctcca aaaataaat aaataaataa taatatgttt tgtatgttca tatgttgcaa     37680
taacattttg gatatattaa atgaaataaa atacattaaa attaatttca cctgtttctt    37740
ttcttttctt tttttttttt tttttgaga tggagtctcg ctatgtcatc aggctggagt    37800
gcagtggcac gatctcggct cactgcaacc tcctcctcct gggttcaagc gattcttctg    37860
```

```
cctcagcctc cctagtagct gggattaaag gcatgtgcca ccacacccag ctaattttg    37920 tatttttagt agagacgggg tttcaccata ttggccagga tggtctcgat ctcctgacct   37980
catgatccgc ctgccttggc ctcccaaagt tctgggatta caggcgtgag ccactgcacc   38040
cagcctcttt taacttttta agtatggcta ccagaaaatt taaaatgcat gtgtggcctg   38100
tattctattt ctgttggatg ctgctgcctt agattattaa ttattcaatg taaagactgc   38160
tgggaggtac tacctgcact tccctgaata tatgcttgag agctccacca gccgtcttca   38220
cagtagcaag aggggtattc tgagtctgtc ccccaaagag ggagggagaa gtgcagccct   38280
ctcaggttct gtcagaaaac ctgatcccag gccaggcgtg gtagcttacg cctgtaatcc   38340
cagcactttg ggaggttgag gcaggaggat tgcttaagcc caggagttcg agaccagcct   38400
gggcaacaca gtgaagaccc tatctctaca aaaattttt taaaaaatt agccaggtgc    38460 agcaatgctg cctgtactcc cagctgcttg ggaggctgag gtaggaggat tgcctgagcc   38520
caggagttag aggttgcagg agttagaggt tccacgatcg caccttcat tccgttacat    38580 ttgctgcctt gagaacagaa gacctgctgg ttttgttgcc agtttgctca gtcattttta   38640
tgaaaaagcc agtgctaact aggtgcttct tcgtgccttc tctgagaatc aagaactcta   38700
gtatgtttgc gtgtgttcag tctctcatta aatgttctca ctatcccaga gaaccatctc   38760
attggacctt ggtctgtaca taccttcatc ttttggctctg acttgtaatt attttttagaa 38820 cttctctttt tttttttttg gagacagagt tttgctctag ttgccagact ggaatgcagt   38880
ggcacgatct cagctcacct caacctctgc cttccaggtt caagcaattc tcctgcctca   38940
acctcttgag tagctgtaat tacaggcatg tgccaccacg cctggctaat tttgtgtttt   39000
tagtagagac agggtttctc caagttggtc aggctggtct caaactcccg acctcaggtg   39060
atctgcccgc cttggcctcc caaagtgctg ggattacagg cgtaagccac tgcgcctggc   39120
ctaattttag aacttgttaa acaacttggg cctctattga tatttccatg acccatgcta   39180
ttcagaaaga ggattacagg taattagctg gctgggtttc tcataccaga gcatttcact   39240
gggatgttcc tgaacctggg acaacttta tgcctggcat ttttcttcc ttctctgttg     39300 tcccagacta agcaattttt aaaatagtta ttatttgttg agtaggagaa tctcaggcag   39360
atcttcctgg atcctcattt atacttttaa acctgtagtc ttggaattag tgctctgtcc   39420
cccaacccca aacatccaat ttctacattt tggctacagt acaggttac tgtgtataac    39480 taaaagggct gtggaggaga aagaaaggaa ccgacatttg ttgggcatct gttatgtgcc   39540
atgcactgag ctgatgctg taggaatatc tcaatacctc tgaggagtgg gaattattat    39600 ctctattta tagacaaggg aatagaaatc tgggagttaa gtaattttt aatttcacac    39660 acttctggta gataatggat tctagaacct ggcataatag ccacttgtca tcccagtgta   39720
aaagagatgt gtggccagat ggggtggctc acatatgtaa tcccagcact tgggaagcc    39780 gaggcaggag gatgacttga gcccaggagt tcaagaccag cctgggcatg tttgttgt     39840 ctcacgaaac atttttaaa aaatgagtgt ggcatggtgt tgtgtgccta gtcccagc     39900 tcctcgggag gctgaggtgg gaggatctct tgagcccatg atcatgccat tgcactctag   39960
cctgggccac agagcaagac tctgtcttca aaaaataata aaaggagct gtgattatcc    40020 caaggtgggg attgtgaatg tgtttgtatt gttctaaact gggagaaaca ggctgggtgt   40080
gttggcttat gcctgtaatc tcagcacttt gggaggccaa ggtgggagga tcacttgagt   40140
ccaggagttc aaggccaccc tgggcaacag gcaaaaaata gagacccat ctctattttt    40200 taaaaataaa ataaactggg agaaagaagc agggtcctcc ccagagcatc tttatcccta   40260
```

```
gtcacagacc tgacacctgt gttgggcaat ggctacttct agattgttta cccctactgg   40320
gacttgtggt gaacatatgc acactttggt ttacagttgg gacccctgat tttagcagga   40380
tggcccaatg gaatcagcta cagcagcttg acacacggta cctggagcag ctccatcagc   40440
tctacagtga cagcttccca atggagctgc ggcagtttct ggccccttgg attgagagtc   40500
aagattggta agtccttctt aagtgactct ccaaattgtt aggtttcagt ttgagtcaag   40560
agacatgaac tcttaatgtc atgccttgct gttccattaa aaaatgtatg ggtacaggtg   40620
atggggaaaa tgagatcagg agataaaggg gcaccctttg gtcttgtaaa gcctttttta   40680
tcttagaagg gcatgtgggc aactgtcttt gacacattga aaccgcctgt atggtggtgg   40740
atgtcttgaa ggttgatttg gacctcattt acttgggcag atcctctata tattctgata   40800
atccagtgat gtggtagaca tattttttct ctgaatgtga attctgtcat agctagaact   40860
ttgggttgat acttgtaatt cccctttagt taaaggaagg agccacaggg gtgtattagt   40920
ctgttctcaa tttgctataa agaaatacct gagactggga aatttataag aaaagaggtt   40980
taatcggctc atagttctgc aggctatata ggaagcatag cagcatctgc tgctggggag   41040
gcctcagcaa gcttccaatc atggcggaag gcagagaggg agcaggcagg tcacatggcc   41100
acagcaagag caagagagca aggggaggt gccacacact tttaaactat cagatctcac    41160
aagaactcac tgtctcgagg acagtatcaa cagggatggt attaaaccat tcatgagaaa   41220 cccacccca tgatccagtc accttccacc aggccccacc tcaaacagtg ggggttacat    41280
ttcagtatga gatttgggca gggatgtaga tccaaactag atcacaggat aagggaagta   41340
gattccattc atagagcaga taatggcaca gatgtccagc aactattttc ttcactttaa   41400
tatgctcagg ctcactactg attttggttt aattcaggcc agtgttaata tgacctggtt   41460
tttccagaat gcatactctg atttggtgaa gggccaggag gtgattcaca gatgttggag   41520
ataggccatc ccagcctggg attacttatt tgtactaata aatctgacca gagttaattg   41580
agggtttaaa gcaaaacagc atatctgtct actttgctca aatattttac aaatacaaca   41640
gattatgaga gtgggtaata atatctggaa taattgtttt tttgttttgt ggttttttt    41700 ttttttttt tgagatggag tctggctgta gcccaggctg gagtgcagtg gtacagtctc    41760
ggctcactgc acctctgcct cttggattca gcgattctc ccgcctcagc ctcccgagta    41820
gctgggatta caggtgccca ccaccacacc tggctaattt tttattttta gtagagacag   41880
cgtttcacca tgttggccag gttggtctgg aactcctgac ctcaggtgat ccgcctgcct   41940
cagcctccca aagtgctggg attacaggca tgagccacca tgcctggcct ggaataattg   42000
ttaataatta ttacattgat ggcatttat tgctgagcaa gaagaatcta acatgatgaa    42060
tgggttatag catcaggttt gctttgtttt tttgttttt tcctcttct tgatggtgat    42120 ttctgtgttt gtgtgtatgc gtcggcttca gagccattct ttatcattct cctttttcct   42180
agggcatatg cggccagcaa agaatcacat gccactttgg tgtttcataa tctcctggga   42240
gagattgacc agcagtatag ccgcttcctg caagagtcga atgttctcta tcagcacaat   42300
ctacgaagaa tcaagcagtt tcttcaggta tgatgagaaa ctgaggacaa ggagaaacag   42360
gacccgcaga gtcgggtgtt agtgttcttt cctggaagca tctctttct catttggcta   42420 agtaacgaga atctatcttg tattttcaat cacaggagaa gtaattagcc ctttctcaaa   42480
gctctgtata cttacccgtg agcatcatta cctgagaatc acttctcttg tcacagttga   42540
agtaataaag tgattgttat gttaatcata catgttagca tgttaacgcg gtccactgat   42600
aggaagatga ctctcactgt tacatgttaa atgtttgacc ataatgggat acttcttgac   42660
```

```
taagtcagta gcttccctgc aagaccagga tagtatactg tgtaaagact cagacaaggc    42720
caggcatggt ggctcacgcc tgtaatccca acaccttagg aggttgaggt gggaggattg    42780
cttgagcctg ggagttttga ccagcttggg caacataa caagacacca tctctacaga    42840
aatttttttt aaaaactagc tgattgtggt ggcatgcacc tgtagtccca gctactcaga    42900
aggctgaggt gagaaaattg tttgagcctg ggaggtcgaa gctgcaataa gccgtgattg    42960
cgccactgca ctccagcctg gcggacagag tgagagccag tctcaaaaaa aaaaaaaaa    43020 gactcaggct aatgtgcctt ctgttacaga aatagtaacg acctcccctt cgcccccgc    43080 cgacagagag cctcacccca ggctctgaag cctttgttcc gttgtttcct agaataaatg    43140
ctttccttga tgaatacatt agttttaagg tgccacagtt cagtccacat ctccatggtc    43200
tgctgctgat ttttattctc tttctctcct acttatagag caggtatctt gagaagccaa    43260
tggagattgc ccggattgtg gcccggtgcc tgtgggaaga atcacgcctt ctacagactg    43320
cagccactgc ggcccaggtg agacctgaga caaaacaaat ccctggtctg ggaggaatgg    43380
aaaatcaaac aactttataa tgagataaat tattagatct actaaaaaag aaggaaaaga    43440
aattaaatag atcaataatc ataaaaatac attgaaaaac tctaaaaaaa aagaaagttc    43500 cacccccaa aatacattga aaaactctaa aaaaagaaa gttccaccaa aagaatccaa    43560
cagacccaat ggtttaaaag ttttgttttg ttctgacaaa ttttctttgt ttttcttttt    43620
ttttttttct gagacagagt tttgctcttg ttacccaggc tagagtgcaa tggcgcgatc    43680
ttggctcact gcaacctcca cctccagggt tcaagtgatt ctcctgcctc agcctcaaga    43740
gtagctggga ttataggcgt gtgccaccac acccagctaa ttttgtattt ttagtagaga    43800
cggggtttct tcatgttggt caggctggtc tcgaactcct gacctcaggt gatccgcccg    43860
cctcagcctc ccacagtgct gggattacag gcgtgagcca ctgtgcccgg cctgttctga    43920
caaactttca tagtacagat tattccaata tcattcaaac ttttccaaag tataggaaaa    43980
caagggatgt tttcagctta ttttatgagg ctggaaaaat cctcatatca aaacctaaaa    44040
aacagccagg tgtagtagct cacgcctgta atcccagcac tttgggaggc tgagacgggc    44100
agattgcctg agcctcagga gttcgagacc agctggggca atgtagcgag acctcatctc    44160 tcttttttttt ttttttgag acagagtctc tctctgtcgt ccaggctgga gtgcagtggt    44220
gccatcttag ctcactgcaa cctccgcctc ccaggttcaa gcgattctct gcctcagcc    44280 tcccgactag ctgggactac aggtgtgtgc caccaagcct ggctaatttt ttgtattttt    44340
tttagtagag atggggtttc accttgttag gcaggatggt cttgatctcc tgacttcatg    44400
atccaccggc cacagcctcc caaagtgctg ggattatagg catgagccac cacgcccagc    44460
cttttttttt tttttgagac agagtcttgc tctgttgcca ggctggagtg cagtggcgtg    44520
atctcagctc actgcaactt ctgcctccca ggttcaagct attccctgc ctcagcctcc    44580 caagtagctg ggactacagg cgcgcgccac cacacccagc taattttttg tgttttagt    44640 agagatgggg tttcactgtg ttagccagga tggtctcgat ctcttgacct cgtgatccgc    44700
ccgcctcggc ctcccaaagt gctgggatta caggcgtgag caaccgcacc tggcttaatt    44760
aaggatcttt ctaaacacaa gaaagaatat ttatcagaaa ccaaagggag catgatgcac    44820
agtggtgaaa cactattctc agtaaaaaca gcaaagata aggatgtctt ttaccattga    44880
tacttttctg agggatccag cctatgcaaa aagaaaaaga aatgagggta caaatattgg    44940
aaagcaaggg acagaactct tattatttac agatagatag gtcttcctcg aagatccaag    45000
agaaacaaaa ctaacaataa caattggaac tagcaaggtt tagaaaggcc attgtataca    45060
```

```
agataaatat ttttagaatc tgcagttccc ctaatcagta gcagcagtaa cctgttagaa    45120
gatgtaatga aagtaaagat ctgggccagg cacgatgtct cacgcctgta atccaagcac    45180
tttgggaggc caaggtgggc agatcatgag gtcaagagat tgagaccatc ctggccaaca    45240
tgatgaaacc ccatctctac taaaaataca aaaattagct gggtgtggtg gtacgcgcct    45300
gtagtcccag ctactcggga agctggggca ggagaatcgc ttgaacctgg gaggcggagg    45360
ttgtagtgaa ccaagattgc gccactgcac tcctgggcga cagagcgaga ctccgactga    45420
aaaaaaaaaa aaaaaaaaaa gaaagatctg attcatagta gtaaaactaa atgtatgcaa    45480
tttgcatata ctattggtat gtatgggaaa atatctggaa acacatatac taaatcatta    45540
aagtagtcgg tcataggaga cttttttact ttctgtgagg ggttttaccg tctttaatat    45600
cctataatca gggacatttt ttcttttttct ccgtgacccc ctgcttttta aaaaattgtg    45660
gtgaaataca cataacatta catttcaaat ttacctttgt aacctttgtt tttttttttt    45720 tttttttgaga cagtctcact ctgtcaccca ggctggagtg cagtggtgtg atcacagctc    45780
actgcagcct caaccacctg ggccctagcg atcctcctgc ctcagcctta tgagtagctg    45840
ggactacagg cacatgccac catgcccagc taatttttt ttttttttt tttggtagag    45900 atgggctctt gccatgtttc ccaggctggt gttgaactcc tgggctcatc aactgatgag    45960
aaagagctct ccaggcagaa agaagatcat gttcaaagac agaaacagaa atgtgtattc    46020
ttgggagaag tgtagaaagt tcagcatctg attgggtcgg ggaagacaag ctagtcaagg    46080
ccacatgatg ttttaattag tcatgcctaa cagtggggcc ctggaagagc agtttaccac    46140
aaggggccaa ctgcttcggt ttgaacccgc agccctgcca cttgctctgt aaccttaagt    46200
aaacaatttt tactctctct gttcctccaa tgggagtgat aacaataccct tcttcataga    46260 attaattcat acatgtaaaa tgcttagaac agtatctgac acataaatgc aaaataattt    46320
aactgctttc tgctgctgct gacatcacta tcatcaccct caccattact gtaggaaatg    46380
gggacccagt gaagaatttt tttttttct tttgagacag agtctcactc tgtcacccag    46440
gccggagtgc agtgacgcga tttcggccca ctgcaacctc tgcctctcag gttcaagcga    46500
ttctcatgtc tcagcttccc aagtagctgg gattacaggc atgagccacc acactgggct    46560
aattttttgt attttagtg agatagggtt tcaccatatt ggccaggctg gtctcaaact    46620
cctgacctca ggtgatccat ccacctcggc ctcccaaagt gctgggatta caggcataag    46680
ccactgtgtc cggccctagt gaggaatttt aagcagaaaa ctgatatgct caggtgtgag    46740
cgaggtggta ggtaacactt actgtgcagt gccctgtagc ccaagaggtt agcacacagg    46800
catttgctca ggcagcacta ggattttctg ctgtggaaaa cctttgtatt ttatcctgct    46860
ccacaagata aaaataagtg gtttaagtca atttggatag aggctccaac ttaccatggg    46920
aggtaggaaa gccaaagtta tcccaaggat gttttcaatc gtacggatta ggggtctgca    46980
aactgtgagc gtggcccaaa tccagcctgc tgcttgtttt tgtaaatgag gttttttcgg    47040
aacccagcca cactcattta tttatgcatt atctgtggct gctttggtgc tgcagtggca    47100
gggctatttg tggcagggac tgtatgaccc aggaaaccaa aaatatttac cctctgtccc    47160
ttagagaaaa agtttgcaac ccctgatata aagctataag ttggttattt gtggcctcaa    47220
cccaggcctc actgctattt tttctgttta caatacctgg catgctctta agtgtctaga    47280
attggttaaa gatagaagag tggatgtaat ccctgctacc aagggctgtc aggctagttg    47340
ggattataag tacacaaaca ctcaaagtga gaaaacacac gaaaaggatg tgtgtcattt    47400
tgtctaagga agttgaataa gatttctcag gaaaagaaac atttgaactg aatttgaagg    47460
```

```
tgagtgagtt caggtgtgtt tgggctgaag cccaggccat gctgagtgga tagcgggtgg   47520
gaagagagtg tggaaacaca ctgcatgcag ggaagagttg ggagtctggg gtgaccaagg   47580
cacagggagg gaaagttgaa gttatcaatt gtgtgaaaca gctttctgtg ttggcctgag   47640
atgtttatag ctggaagcag tggggagcca atacagtttt ttacgaaggt attagaggtg   47700
ggtttctgtg ggtgatcgtt aatcatgttt tctccctttta agtgtagtcc tgcttgagaa   47760
atagacatga gaaggaatg aaggttaaaa catcagctgt attgttggta aaactagaat   47820
ggaaagtgtg gcttgagctg gtaaccatag gggctttcca atgcctgtgc cctgagttag   47880
atcttggggt agagagactg gatgtgcaga gcagcacccc cacccaccc cagccatcca   47940 tatggagctt cagctgccat agaccaacaa ggcagaggga taggcctcta gacctgcttc   48000
tagaaaccag gctgctgctc ttgcttatgg tgggccctag gaaggcaaga gtgagaggag   48060
ggaggcacca gcttaggtgc tgggttcttt gaagatctgt gtgtacacag agtctttctc   48120
tccatcttac caatcagatg agtcactgtc actgtgggaa gaagtagggg catgggtcac   48180
cttcccaaaa cttctaagaa gtttgtattc tgtgggcttg gatagggacc atgggaaagg   48240
aagagaatgg ttgcccataa aactggctgt agtgtggcct caaacttctg gacttaaatg   48300
atcctcccac ctcagcctcc caagtagcta gaactacagg tatatgccac catgcccagc   48360
tagttaaaaa aaaatttttt ttttttttg gttgagatga ggtctctttc tatgttccct   48420
gggccggtct caaactccca gcctcaagtg atcctcctgc cttggtttcc caaagtgcta   48480
ggattatagg tgggagctac catgcctagc ccaagcctgt aattttttt tttttttt   48540 gagatggagt ttcacttttg ttgctcaggc tggagtgcat ggcgcagtct tggctcacca   48600
caacctccac ctcccgggtt caggcgattc tccttcctca gcctcccgag tagctgggat   48660
tacaggcatg caccaccaag ctcagctaac tttgtatttt tagtagagat gggtttctcc   48720
gtgtcggtca ggctggtctc aaactcctga cctcaggtaa tctgcccacc ttggcctccc   48780
aaagtgctgg gattacaggc atcagccacc gcacctggcc cgaacctgta atttttaagt   48840
ttcatatgct atttatttt tgttatttct ttaattcatt cattcattta ttcattcgag   48900
atggggcctc actatgttga ctaggctagt tttgaactcc tggcctcaag cagtcctccc   48960
acttcagcct tcccaagtgc tgatattata ggtgtgagct gctacatcca gccttctttc   49020
ttctttttct ttttccatgt gctatttgac attttccaag gtaccagcct ccccttctcc   49080
ccaagataat atcttttaat atggaatttc atccctaggg caggactttt ttttattat   49140 ccctcagaaa tatactggac accacgttta agtagacatc caacatctgc tgtcataaat   49200
tgttttgaat tttttgacat acttgcccat gaggttttttg aaggcataga ccatgtctta   49260
gctgaacatg tggtctctta gtgccataaa gggggtttat ggtatgacct gtgtagtgtc   49320
acctgtgtag tgacagcacc actgcctctg tttcccttcc tcttgtgatg gcagcagcgt   49380
ctcaagccaa acaagaaggg tagttagggt gggatggaag ctgggtagag gtattcctct   49440
ccccatagtt ctgtgttcac atgtgcattg acctcctttt tggcagcaag ggggccaggc   49500
caaccacccc acagcagccg tggtgacgga gaagcagcag atgctggagc agcaccttca   49560
ggatgtccgg aagagagtgc aggtgatgca agttacaagc ctcgggcagg gagctttcat   49620 taatttttt ttttttttt gagacagggt cttgctctgc cactcaggct gggctgcagt   49680
ggcatgatca cagctcactg cagcctcgac ctctcaggcc caagcgatcc tcctacctca   49740
tcctcccaag tagccgggac cacaggcatg caccaccacg cccagctaat taaaaaaaaa   49800
aaatttgtag agatgggggt ctccctgtgt tgtccaggct gatcatgaac tcctgggctc   49860
```

```
aagtgatcct cccaactcag cctctcaaag tgctggcatt acaggcgtga gccactgcac    49920
ctggccaaca gggagccttc tcttggggat actgcctgca ggtcctgcat gtatcttttt    49980
tgaggttttg gcttcatttg aattctcctc agaaacttta tattttctgt tcccaaggaa    50040
atctttcttt acttctgttt ttttgtttgc ttattttaaa caggatctag aacagaaaat    50100
gaaagtggta gagaatctcc aggatgactt tgatttcaac tataaaaccc tcaagagtca    50160
aggaggcaag tgaatattag agatgttaaa atctctagaa agtgagtttg tgttgttgag    50220
ttgaaagact catttgtctt aactctgttt agatcttaag gcgggcgggg cgcaagggag    50280
gtacgggtcc tcaaaggagc ctggtcatta aggacaggag tattccctca ggtccaggag    50340
tattccctca ggtccaggag tattccctca ggtcaaggag tattccctca ggtcaaggag    50400
tattccctca ggtccaggag tattccctca ggtccaggag tattccctca ggtccaggag    50460
tattccctca ggtccaggag tattccctca ggtccaggag tattccctca ggtcaaggag    50520
tattccctca ggtccaggag tattccctca ggtccaggag tattccctca ggtccaggag    50580
tattccctca ggtccaggag tattccctca ggtccaggag tattccctca ggtcaaggag    50640
tattccctca ggtccaggag tattccctca ggtccaggag tattccctca ggtccaggag    50700
tattccctca ggtcaaggag tattccctca ggtccaggag tattccctca ggtccaggag    50760
tattccctca ggtccaggag tattccctca ggtccaggag tattccctca ggtccaggag    50820
tattccctca ggtccaggag tattccctca ggtccaggag tattccctca ggtccaggag    50880
tattccctca ggtcaaggag tattccctca ggtccaggag tattccctca ggtccaggag    50940
tattccctca ggtccaggag tattccctca ggtcaaggag tattccctca ggtcaaggag    51000
tattccctca ggtcaaggag tttttcttc cttcgcagac atgcaagatc tgaatggaaa    51060
caaccagtca gtgaccaggc agaagatgca gcagctggaa cagatgctca ctgcgctgga    51120
ccagatgcgg agagtaaggg cataggtcgg accacttccc ccatgtgtct cgctcacttg    51180
cgggatttca gcgtcttgtg gcagaacttg cttggtttct aagaagttcc tgctctggag    51240
ttgactaaag aatgtggtta gagacagtct gaggaaatgt tttctgactt tgttttggtt    51300
tccaaccaga gcatcgtgag tgagctggcg gggcttttgt cagcgatgga gtacgtgcag    51360
aaaactctca cggacgagga gctggctgac tggaagaggc ggcaacagat tgcctgcatt    51420
ggaggcccgc ccaacatctg cctagatcgg ctagaaaact ggtaaaggat gaaagaagct    51480
tttcctttct ttctcgaaag ctagattgaa ttctgatctt aactgcaggc ccacagaatt    51540
ggtactatat ctccaacgtg gggacttttc catattcaaa tttagcccaa gaattaaagt    51600
ttttacttta tttcggccag gcgctgtggc tcacacctgt aatcccagca ctttgggaga    51660
ccaagatggg cggatcactt gaggtcagga gtttgagacc agcctggcca acatggtgaa    51720
aacacatctc tactaaaaac ataaaaaaat tagccgggcg tggtggtgcg cacctgtagt    51780
cccagctact ctgggcggct gaggcaggag aatcacttga acctgggata tggaagttgc    51840
agtgagcgga gatcttacta ccgcacacca accagcctgg gagacagagt gagactccat    51900
ctcaaaaaaa taaaaataaa ataaagtttt tactttattt ggagaaactt tgttttaaaa    51960
aatgtattta tattattata ttttaagtat attttactta ataattcaat taaggctttt    52020
ggtttaactg tatttaacag atagacaaac cttttaattt tagttatttt agtaatctaa    52080
aatgacacat gcccttttta agggaaaaaa ttcaaataca gaaaattaat caagagaaga    52140
aaaaatttt aaatgaaatc atcagcagta ctagtagtta aaatttagtt gatgctcaat    52200
ctagacatct gtcattatgt atatacacat tatgtatata cacataaaga tagaaattta    52260
```

```
tacagtttat attaggatca ttttttttc ttttttttgga gtcagggtct cactgtgtta    52320
cccagtctag agtacagtta tgcagtcatg gctcactgga gccttgacct cctgggctca    52380
ggcagtcttc ccaccttagc cttctcagta gctgggacta caggcatgca ccaccacacc    52440
tggctaattt ttaaattttt tatagagaca gggtcttact tgttgcctg gctggtctc      52500 aaattcctgg gctcaaggga tcatcccact tcggcctctc aaaagctctg gaattataga    52560
tgtgagctgc cgtgcccagc ccaggatctt cctttatatg cttttctgta atttgcactt    52620
ttaccttcat ccagcatatc ttactgcaac ccttcctgtg caaggcccta tagtgagcat    52680
gttgcaccag cttgccttag gagaaacttg agatacagag cctgcactgg aaatttagcg    52740
caactctaca tgagaatgcc tgtctattca tatcctcact aaccctgagt gttgttaatt    52800
tactgaaagc agttttaaat gcttcctgac cagggaacga agaagcttaa gttctgggaa    52860
tgggaggata gaagtgccag aaaagagctc aggagttcag aaatccctgc agcggtcccc    52920
ctccctctcc tttcactttc tgtctttctg gtcttttggt ctttgttaca ctagtgataa    52980
accatcaaag aatgatggaa tgatgctaac ttctctcttt ttttaatttt tttgagacag    53040
agtctcactc tgtcacccag gttagagtgc agtggcatga tcttggctta ctgcaacctc    53100
ctcctcccag gttcaagcga ttcttagtca caaccttcca agtagctggg attacaggcc    53160
catgccacca tgcctggcta ttttttttgta ttttagtaga tcgacctgcc tcggcctctc    53220 aaattttgg gattacaggt gtcagccact gcacctggcc taatatctct attcttggag    53280
atagatttaa tgagcttttt ctccctctct attcacttat tccttgtgca tgttatcaat    53340
attttgaaac ataatgtcat gtcctttgat cagttgaagg ctgacattga aaaggcttat    53400 gggattggg tgttgtggct cacgcctgta atcccaatg ctttgggagg cagagtcggg      53460
aggatcactt gaacccagga gtttgagacc agcctgggca acaaagtgag atcccatccc    53520
tacaaaaatt taaaaaacta gacatgtgcc attacacttc agcctgggtg acagagtgag    53580
actccatctc aaaaaactaa actaaactaa acaggcatgg tggcacacac ctatagttct    53640
agctactcag gaagctgagg taggaggatc actcatgtcc aggagttgga ggaggcagtg    53700
agctatgatc atgccattgc actgcactag gccacagagt gggaccctgt ctcaaaaaaa    53760
aaaaaagaaa gaaagaaaag aaagggctca tgtagttcaa gcccttctct tcatgcaagg    53820
ggatgctaag gcccatgatg gtgaagggcc tggcaaagct tgcacagata gtgtgtgaca    53880
gagctggctc aaacccatct ttgggagctg tctaatctct ttttctgagt ctttatgttc    53940
atagacaagt taggatgagt aaagtaagtg ctaaattcca tatttcgtgt tctgcatatc    54000
tgggctcaga tgcttgtcat tttccagtga taactccatc aatgcctcct agtggtataa    54060 atttaatac ttcttgtgtg cccagccccc tcttagaaat ttgagatttt aggaagggac    54120
tagtaataaa aggtaaaata aattattttc tggccaggca tggtggctca cctgtaat     54180 gccagtactt cgggaggtcg aggcagatgg atcacctgag gtcaggagtt caagaccagc    54240
ctggccaaca aggcaaaatc ccatctctac taaaaatgca aaaattatcc gggagtggtg    54300
gtgggtgcct gtaatcccag ctacttggga ggctgaggca ggagaatcac ttgaacttgg    54360
gaggcggagg ttgcagtgag ctgagactgt gccactgcac tccagcctgg gcaacagagt    54420
aagactctat ctcaaaaaaa aaaaaaaaa aaaaaggcc aggcgcagtg gcttacacct      54480
gtaatctctc aggaggctca ggcaggagaa tcacttgaac ccgggaaatg gaggttgcag    54540
tgagccgaga ttgcaccact gcactccagc tcaaaaaata aataaataaa taaattattt    54600 tctttttta tttatttttt cagcatccac ccaacatggt gaaaaattcc tctttcttta    54660
```

```
atgtcactga actgtaaact taagatgaaa aattgtaaat ttcatgctat atatatttca   54720
ccacaataaa aaaattcctt gttcttattg tagtggtctc catgtcttca gtatttcctt   54780
cccCTtctcc atctcacctg tatacattca ctttggtaat tagcatcttt cttaatttat   54840
tggcaggata acgtcattag cagaatctca acttcagacc cgtcaacaaa ttaagaaact   54900
ggaggagttg cagcaaaaag tttcctacaa aggggacccc attgtacagc accggccgat   54960
gctggaggag agaatcgtgg agctgtttag aaacttaatg aaaaggtaat ttagcatcct   55020
tgtccctttc cctcatctaa aaaatacctc aagactcacg tggtagagtg agaggcgggc   55080
tgacttctgg tcatggccgt ggcgcgtgag cccatcttct ctttcctcag tgcctttgtg   55140
gtggagcggc agccctgcat gcccatgcat cctgaccggc ccctcgtcat caagaccggc   55200
gtccagttca ctactaaagt caggtaggcc atgccacttc catttccagt agagatttta   55260
ctgagggaca ctgttagggt gagggtagag ttggtggcca gggtcattct ttccaggtgt   55320
ggtgtcacag gcagtacact gttgcggggt tgaaatttgt tgccatacta tctgcttgct   55380
ctctgattct gatgtcaaaa gcaaaagagc agtcatcttt ttgaaggtac ctgggcatat   55440
tcctatgatt gtagacctgg agtctcaggc cacagcttct ccttctgccc aagggacaaa   55500
ataatgtcat ctatttttctg ttctttgagg ctactcttcc ctgtggattt taagggaaag   55560
agtaaggctt agtgatgggg aagctgagag gccccagggc aggtgggtgg tgggcctgta   55620
gggtgaggtg ttactttcac actcaagtca gaacaggtgt gctggggttt tgaccttctg   55680
cagcaaaatt tccctcctca gaaacttagt atggtgttcg gtttcaggat taatagaaca   55740
aaatgccagc tgcacagcat gtgttcctgt aatattttc attatatggc tttgattatc   55800
cttttgtgaa tctctcacaa ctttaagttg ttagttctta gatgttttct cagtaccttt   55860
ggcttgaagg agtgatactc atcttttgtt tttgtttgag acagggtctc actctcaccc   55920
aggctggtgt gcagtggcat gatctcagct cactgcaacc tccatctccc aggttcaagt   55980
gattcttgtg cctcagcctc ctgagtaact gggaatagag gtgcgtgcca ccacacccgg   56040 ctaattttt ttttttttgag acagagtctc gctctttcgg ccaggccaga gtgcgtgttg   56100
caatctcaac tcactgcaac ctccacctcc caggttcaag cgattctcct gccttagcct   56160
ccctgagtag ctggaccggc acactccacc atgcccggct aattttttgta ttttttagtag   56220 agacagggtt tctccatgtt ggccaggctg gtctcaaaac tcctgacctc agtaatccac   56280
ccaccccggc ctccaaaagt gctgggatta cagatgtgag ccaccacgct cggccttttt   56340
tttttttttt tttttttga gatggagtct ttctctatca cccaggctag agtgctgagg   56400
tgtgatctcg gatcactgca gcctctgcct cctgggttca agtgattctc ctgcctcagc   56460
ctcccaagta gctgggatta caggtacctg ccaccatgcc cggctgattt ttgtattttt   56520
agtagagacg gggtttcacc atcttggcca ggctggtctc gaactcctga ccttgtgatc   56580
cacctgcctt ggcctcccaa agtgctggga ttacaggtgt gagtcaccgc acccagccct   56640
attttaattt ttttaaagag agagataggg gccaggcacg gtggctctcg cctgtaatcc   56700
cagcactttg ggaggccaag gtgggtggat cacctgaggt cgggagttcg agaccatcct   56760
gaccaacatg gagaaactct gtctctacta aaaatacaaa attagctgag cgtggtggcg   56820
cgcgcctgta atcccagcta cttgagaggc tgaggcagga gaatcacttg aacccaggag   56880
gcggaggttg cggtgaacgg agattgcgcc attgcactcc agcctgggta acgagagaaa   56940
ctgtctcaaa aaaaaaaaaa gagaaagaga gataggatct cgctctgtca tctaggctag   57000
agtgcagtgg catgatcata gatcactgta gccttgaact cctgggcaca agtgatcctc   57060
```

```
ttgcctcagc ctcccgagta actgcgacta caggtacatg ctaccacacc ccgctaattt    57120
ttaaattttt tatagatgtg ggctctcact ttgttgccca gactgttatg gaactcctgg    57180
gctcaaggga tcctcccagc ttggcctccc acagtgctga gattatagat gtgagcctgt    57240
aattatagac agcttggcct atttacctgt tggaaatgaa gaattatgaa ttttacattt    57300
cttcaagaaa aggttatggg agagttactg acttttttc cttggatttt ttcttttaa    57360 ataggttgct ggtcaaattc cctgagttga attatcagct taaaattaaa gtgtgcattg    57420
acaagtaagt actcctatct tagctctgtt tttcaaatga ggaatagaaa aatgagaact    57480
ttgacagaca tcatttgaac tagagactct gtctttattc agagatcttc attttgtgga    57540
caaaagtttt caaaagcctt ggggtgcatt gtcatttacg tgtctgaaca aagccacaaa    57600
gctgggggta cagatttgat ttgtggttgc tattgtgaca accagtccct cttttccttg    57660
tttagttttt tacttgtaca tgtcattcat gcatattata tataagactg agatcatgtg    57720
ttaattaacg actgggatac gttctgcaaa atgtatcatt aggcaatttt gttgtgcaaa    57780
tgttgtagag tatatagtcc ttacacaaac ctgggtggca gaacctactg cacacctacg    57840
ctatgtggca gagcctactg gtcgtaggct gtaaacctgt acagtatgtt actgtgctga    57900
ataccgtagg caattgtaac acatctcaat gaagtaggaa tttttcagct ccatgataat    57960
cttatgggac caccatcata tatgcatttt gttgttgacc gaaacgtcgt tatatattct    58020
ttccatacat agcatgtgga aagaatagat ctctttttt taattgttcc acactttacc    58080
atataatgga atacgcaaaa tttcacaata cctttcagga tgtaaaatac atataccctt    58140
tgacgacatt agaaaagaga aaatgtgggc cgggcgcggt ggctcatgcc tgtaatccca    58200
gcactttggg aggccgaggc gggcggatca cgaggtcagg agatcgagac catcctgggt    58260
aacacggtga accccgtct ctactaaaaa tacaaaaaa ctagctgggc gtggtggcgg    58320
gcacctgtag tcccagctac tcaggaggct gaggcaggag aatggcatga acctgggagg    58380
tggagtttgc agtgagccaa gatcacacca ctgcactcca gcctgggcga cagagactcc    58440
atctcaaaaa aaaaaaaaa gaaaagaaaa gagaaaatgt ggctgggcgc ggtggctcac    58500
gcctgtaatc tcagcacttt gggaggctga ggtgggcaga tcacctgagg tcgagagttc    58560
gaaaccagcc cgaccaacat ggagaaacct tgtctctact aaaaatacaa aattagccag    58620
gtgtgttggc gcatgcccgt aatcccagct acacgggagg ctgaggcagg agaatcactt    58680
gaactcagga ggtggaggtt gtggtgagcc gagatcacac cattgcactc cagcctgggc    58740
aacaagagcg aaactatctc aaaaaaaaaa aagaaaaaa gaaagataa aatgcattct    58800 tatttttagt tgatgtaatt atgtggaaat tcatgagga tgcactggaa aataatgaaa    58860
taagggagtt gacgaaggtg gtaggtttaa taagtacata tgcaatatga aacataggtt    58920
cccctcccta tggggaggca accaactgtg cctgctacgc agaggtgtta tgttgcgctg    58980
atcaactgta actgaatagt ttaaagaaat gcccaggagc acagaggttt tttcatgaca    59040
gtaaataaca ggtggtcaaa gtaggctttt tgaagaaaca cagagcctat tttattaaca    59100
acagtctgtg ttcttacaga gactctgggg acgttgcagc tctcagaggg taagttcagc    59160
ctagaggctt ccttttgttc cgtttaacct aacttcatcc tccggctact tggtcaccta    59220
catagttgat tgttcccctg tgattcagat cccggaaatt taacattctg ggcacaaaca    59280
caaaagtgat gaacatggaa gaatccaaca acggcagcct ctctgcagaa ttcaaacact    59340
tggtatgtgg gaggagctcc ccttcacaaa gggcctctgg ctgccggaga gggctaggga    59400
gagcctcaca ggacacctgc ctttttcttt tcttacagac cctgagggag cagagatgtg    59460
```

```
ggaatggggg ccgagccaat tgtgatgtaa gttttgttgg ggatgaaaga caactggggt   59520
gttttccttg agggagagag gggtaaagat ccttcttaat ccccagaatt agaaacatca   59580
acctgttctt tcagctgtag ttattccaaa aagtcacttc aggccaaagt gacatgaaca   59640
gaagttccat gtgccatgga gctctctggc ttggaacatt ccgtgaata tctgggagtt    59700 ggctcctcct taaggagaag tggaaagtcc cttgctgagt tgttctccac acccatgtgg   59760
tataaagcag ctttccacct tgcctgggc ttttccaaatt cccatccag ctcctgcggc    59820 tgaccctgct tggctccatt tttagtgccc tgttttctc tcccactgag gtgggataga    59880
gggtgtaaaa gcaacagatt tgagttaaac tttaaaataa atgaccacct tgcattagct   59940
tgcttaggaa aagagtacat aaaataaaat gaacaaacaa aaacccatct tgttctttat   60000 ccccttatt ttctgctttt cattgattca gattattgga ttcttattgt caagaataaa    60060
ctttaaacaa acaaacaaaa aaaggtaaat gtgacggaag gctagttttc agtcattttt   60120
aaaaattgtg atgccccgtt ctttttctta catttgtccc ctgaacaatt cttcctcttt   60180
aaaatgtagc agtcctagct gggcgtgctg gctcacaccc cgtactttgg gatgccaagg   60240
caggctggtc acttgaggtc aggagttcaa gaccagcctg gccaacatgg tgaaagcccg   60300
tctctactaa agatacaaaa attagctggg tgtggtggtg cacgcctgta gtcccagtta   60360
ctggggaggc tgaggcatga gaatcgcttg aacctgagag gtggagcttg cagtgagcca   60420
agattttgcc actgcactct agcctgggca acagagtgaa actctgtctc aaaaaaataa   60480
ataaaataaa atgtagcagt ccttttaaa aatgtggaat tttacttgac agtagagtga    60540
agtagcctgt atgcaatgat atgggaaaat gtacatgaca tattaagaaa aagcaaaatg   60600
taaaataatt tgaatagtat tattagtata tgtgttttaa aaatacacta tactcttatg   60660
tgtattcata tgtatattaa gaaattctgg aggaatatac cagcagtgct atgtgtatta   60720
gtgctgctgt tggtatccat ggctattcta gactgtctct gtgatatttg cattttaaac   60780
tgaatatatt acttttataa tcagaaaaat agtattaaaa atgaattata atttaatttc   60840
tttttctttt ttttttttg agtcggagtc tcgttctatc ggattgcagt ggtgcgatct   60900
cagctcactg caacctctgc ctcctaggtt caagcgattc tcctgtctca gcctcccaag   60960
tagctgggac gataggtgca tgccaccacg cctggctaat ttttgcattt ttagtagaga   61020
cagggtttca ccatattggt caggctggtc ttgaactcct gacctcgtga tccacccatc   61080
tcggcctccg aaagtgctgg gattacaggc atgagccgct gtgcccagac tagaattcaa   61140
tttttgagaa ttcattgaca actcttactt aaaataaggt tgctgtactg atgtgagaca   61200
ttgttgtagt cagtttggaa aacaatttgg cagtataaaa atgaacatac ctgtaaacca   61260
acggtgccat tcccaggatt taatagcaga gaaatctttg catatatgtc ccaggagaca   61320
tatataaagt ggacatcagc ctgattataa gctctaaatg caacccaaat aaatacccat   61380
caacattaga atgaatacat tatttgtggt atagacacaa tggaatactc cgcagctgtg   61440
aaaaggaata cactgcagat acacataacc atgtggattc atttcacatc aagtgaaaag   61500
tgaatcccaa aagaattcat tggagtccat aagtgtaagg ttcacaaatg tcccaaacta   61560
aacaatacct gcattgctta gataaacaaa tatggtaaaa ctgtaaaaaa acaaaacaaa   61620
acaagacaaa aagggctagg aaatgataaa cccaaaagac aaaatagcag ttatttctga   61680
gggaggaggg aaggggatgg ggttggggaa gggcacccag agaattttag gagtgatgga   61740
ctttccctta aattgaatgg tgggttcata ttgttttgtt attctttgtg ccttacgtat   61800
tttacaaata accaattgga tctatgtaat attataaatac aaactgagta aaggattagg   61860
```

```
ttgaggatca cagcattgga agttcttggt gttgaagaga gtaagtgccg agcaagttgt   61920
gtccctggca gtttgtttgt gaccacctgg tggcttaccc ttcttggtgt ggtgaggctt   61980
ggcatgtcac tttccttggc tgtggctgtt agtactgaat gccattctct ctgaggaaaa   62040
gtgtccttct ctttttttatt gattgactga ttgattgaga cagagtctca ctctgtcacc   62100
caggctggag tgcagtggcg tgatctcggc tcactgcatc ctctgcctcc tgggttcaag   62160
cgattctcct gcctcagcct cctgagtagc tgggactaca ggcgcccact accacaccca   62220
gctaattttt gtattcttag tagaaacggg gtttcaccaa attattggcc aggctggtct   62280
cgaactcctg accatgtgat ccacctgcct cggcctccca aaatgctggg attgtaggtg   62340
tgagccatca cgctcagcct ttttttttat ttaatttaat ttttttttaa dacagggtct   62400
cactctgtca cccagctag agtgcagtgg cacaatcata gctcgctgca gcctccatct   62460
cctaggctca agccatcctc ccacctcagc ctctcgagta gctgggctagt taggtgtgca   62520 ccaccacacc cagctaattt ttgtatttttt tgcagagatg gagttttgct gtgctgctta   62580
gactggtctc gaactcctgg gctcaggcaa tcctcctgcc ttggcctccc aaagtgctgg   62640
gattacaggc atgagccacc acacctggcc taagagtgtc cttctcgtta ctgtaggctt   62700
ccctgattgt gactgaggag ctgcacctga tcacctttga daccgaggtg tatcaccaag   62760
gcctcaagat tgacctagag gtaagttctg cagcagaatc ggtgagaggc tacgtacagg   62820
ggtgactcag gacaaaaact tccactggga ttttacaag agaaggtgga atgattactg   62880
tttgcttaac actgtgttta ttttttgctta cttttctcca aaaaaatcct tggcatccca   62940
tctggcaata aagtcttgct tgaatgctta gaagatgtgt gtatattcag ctttcagcaa   63000
acttgatatg aaaatctcta tttagaaatt gattggccgg gcgcggtggc tcacgcctgt   63060
aatcccagca ctttgggagg ctgaggcggg tggatcacga ggtcaggagt tcgagaccag   63120
cctggccaac atgacgaaac cccgtctcta ctaaaataca aaaattagct gggtatggtg   63180
gcggacgcct ataatcccag ctactcggga ggctgaggca ggagaatcac ttgaacctgg   63240
gaggcagagg ttgcagtgag ctgagattgt gccattgcac tccagcctgg gtgacagagt   63300
gagactccgt ctcaaaaaaa aaaaaagaa attagaactg actttataaa gtttgggcat   63360
aagagtctta gcagccagtg tgtttagtat acagaaaatt gtggcaatga cattctcctt   63420
tcccaacttt cttgattttt aaattaagat ataccctagaa aagcaggaat cctggtcttt   63480
gattcctgag acctccctgt ttcatgtgaa gatacagctt caagtcttgg agaatgcctc   63540
caaggtctta aaaatgggga atctgtggat tgtgagtcaa gctttgagca agtcaggttt   63600
tacaagggac cggtatattc cgactgcagc ctgagttgtg tggccacgct gggcattctt   63660
tccactatga gtgctcactg agctgactca ctcacactcc tcgcctagag ttggcagcag   63720
gtgtggttta tggcatgtcc tttcattctg agcccgtga gatgcgggtg aagagatttc   63780
caaggctgtg agagcccctc tgcctcccca gctcagtccc cactccctcc gcagaccac   63840 tccttgccag ttgtggtgat ctccaacatc tgtcagatgc caaatgcctg ggcgtccatc   63900
ctgtggtaca acatgctgac caacaatccc aaggttagtg ccccctcctt ttagttggtg   63960
ccccgggatc tcttgcgact taggggtacc tagtatagac aatgagcacc atccctcatc   64020
taaacaagca aatgtgttct ttccaataga atgtaaactt ttttaccaag cccccaattg   64080
gaacctggga tcaagtggcc gaggtcctga gctggcagtt ctcctccacc accaagcgag   64140
gactgagcat cgagcagctg actacactgg cagagaaact cttgggtccg catttcaccc   64200 cttctcccctc ccgcccaccc gcccagaaaa gggatccggc ccatagggct gttcatttgg   64260
```

```
gccatgtcta ctgagcatta ggccatgttt ctttcctgag caaggcgctg tgctggtgcc    64320
aggaaacagg ggagttgggg agttggggtg cagagacagt ttgcagtttt cagtcgaggt    64380 gatcatttt gaggtgggag gtagatttct tttctcctgg ttgctgtctc attcacccac    64440
tctatctaac tttagaagat cttttaagtg tgtgttggaa ggtggcacta aaggcttgac    64500
attccctgtc cattttttta ataaactata ggctagttgg ttttttttgt cttatttat    64560 ttatttattt attttttga gacgagtctt gctctgttgc ccaggctgga gtgcagtagt    64620
gtgatctcgg ctcactgcaa cctccgcctt ctgggttcaa gcgattcttc tgcctcggcc    64680
tcccgagtag ctgagactac aggtgctcac caccacgccc agctaatttt tgtatttta    64740 gtagagacgg ggttttacca tgttggccag gatagtctcc gtctcttcac ctcgtgatcc    64800
gcccacctcg gcctcctaaa gtgctgggat tacaggcttg agccactgtg cccagcgtag    64860
gctagttttt aaaaagaat tagtggaata ttttatgtgc cacctgggct agaagtagct    64920
ttgttctaat aaagctgttg ccaccaaata cacctgtctg acacccgatg tcagcttgtt    64980
agtgagtgct gctgttggtt cccagcctac cacccgaggt tgggaagagc aggggggactt    65040 gttatatcac cctccatccc tgctgggcta cccagcaaca caagtgagtc aaatgatggg    65100
atagtgtttg tcctcatgtg cacacacaca acagtgccta ccttcaaaga tgtgaaagct    65160
gattattttg tggcccattg tgggatgaat gtgtgtgtgt tctgttttaa gaaataacct    65220
cttgacccca agctgaaaat gtactacttg actcttttc tttccttcag gacctggtgt    65280
gaattattca gggtgtcaga tcacatgggc taaattttgc aaagtaagca atcttgttaa    65340
attctcgtgg gaatgggaat gctcacctgc acggctgtcg ttgagggctc tggcttgaag    65400
gccctgaact cttggtccag cggccagtag gacctgcctg aaggtagacg ggcctgagga    65460
tttgggtgat gcactgcacc cctaggaagg gaagggctgg gatggcagta gacttggctt    65520
tcccattact ctttctcca ggaaaacatg gctggcaagg gcttctcctt ctgggtctgg    65580
ctggacaata tcattgacct tgtgaaaaag tacatcctgg cccttgggaa cgaagggtag    65640
gttggacaga gtgtgcacag atgtaaccaa gtcccctgct ctcagcaagc cagtggcagg    65700
ggatggatgc cctgttagca ataacaacat tgttcctcct ccttggctcc aggtacatca    65760
tgggctttat cagtaaggag cgggagcggg ccatcttgag cactaagcct ccaggcacct    65820
tcctgctaag attcagtgaa agcagcaaag aaggaggcgt cactttcact tgggtggaga    65880
aggacatcag cggtaaggga ggctcccacc caccccacct gctggtggct gctgaggcct    65940
catcactgct tctagttgca agcacctact gcccctggt gggtggagat ggccttgact    66000
ccctgtttca ctcagactcg caaaacacat ttgcgtgact tctaaatcct tccagctgaa    66060
ggattggttt gctttgtttt gcttgctcca gtgactattt ttgagaatt ttgcaattta    66120 aattgtattc ttcatctctt tttctactta accctgttaa tatatcttac gcaagtagtt    66180
atattcaagt ttatttcta tgacccaact agtagcctct tcttaattag aagccagcct    66240
gaatatttcc acagtgccag gccactgaac agggtgttca gggtctcaac actagggtgg    66300
cttaagtctt ttccccttcg aggaaagaaa aaatgggcag ttttctctga gatgacctag    66360
ctgtaggttc catgatcttt ccttcccatg tcctgtgaca ggtaagaccc agatccagtc    66420
cgtggaacca tacacaaagc agcagctgaa caacatgtca tttgctgaaa tcatcatggg    66480
ctataagatc atggatgcta ccaatatcct ggtgtctcca ctggtctatc tctatcctga    66540
cattcccaag gaggaggcat tcggaaagta ttgtcggcca gagagccagg agcatcctga    66600
agctgaccca ggtagttgtt gattttccat gttcctggca tttaattttt gggaaaagtt    66660
```

-continued

```
ggaaattttg ggatccttgg aggatagata ggcaaatgcc tgaataacct gggggataat    66720
tatttctcct tatgggaaag aattgtagtg agtgcttttg ttggggtgac cgatgggatt    66780
tgagaggaga atcagaatca cttagagtag tgtagttcct gctccacaga gagtgcatga    66840
gtctaaagag gggatacagc ctgggcaata tggtgaaacc tcgtctctac aaaaaatcca    66900
aaaaaattac ccggtgtggt ggcacgcatt tgtagtcgta gctacttggg aggctgaggt    66960
gggaggatca cctgagccaa ggagttcaag gctgtagtga gcggtgatca tgccaccgca    67020
ctccagcctg gctgatagag tgagatactg tgtcaaaaaa taaaaataaa gagggatca    67080 atacacatac gtcccccaaa acatgcctga aacacgagaa gggaaagtga gggcagttaa    67140
caggatgccc tgctggcaca gtgcttctta gtagatgcta gaaggtttga ggcccagatt    67200
tcagcccagc atatggcttt ttgcctgtaa ctgaaccatg tcagtgtgcc agatggtctg    67260
aagaaagggt ttctggagga aattattatt agctgcatgg gagtatggtt tacactagag    67320
tagaagagct gggagcatca cgtttgaagg ggaagacagt gactgggtgg aggggcaagg    67380
gattagtatt tagagtgtgc aactattgaa aataaggtat attttaatgt gtaagaggac    67440
atgtacttat atgttatata taaattattt tagctgggtg aagtggctca tgcctatagt    67500
cctagcactt tgggaggccc aggcgggagg atcacttgag cctgggagtt tgagaacagc    67560
ctagacaaca tagtgagacc ctatctatac aaaaataatt ttttttaaat tagccacgtg    67620
tggtggtttg tgcctgtagt cctagctact cgggaggctg aggtgggagg attgcttaag    67680
cccaggaggt tgaggctgca gtgagccatg atcgcaccac tgcactccag cctgggtgac    67740
agagcaagac cttgactcac caaaaaaaaa aaaaaaaaa agagagagaa attaaaaata    67800
ctgtaatctc agctgggcat ggggggttcac acctgcagtc ctagcacttt gggaggctga    67860
agcaggagga tcacttgagg ccaggaactc aagaccagcc tggcaacata gcaagacccc    67920
actacacaca cacacacaca cacacacaaa gaagagaaag aaaaaaacga aacaaaactg    67980
taatctctgc agctgtcctc agtgtggagg gggtagccct gtctgttccc cttcagcact    68040
tgctgttttg actctctggg ttctttgtgc aggtcttgat ggggagtctc tggtttgcca    68100
ttctttgttt gatttaactt tctgtaatca taaagccaat gatgggcttt ttttttttt    68160 ttttttttag actaagtctt gctctatcac ccaagctgga gtgcagtggc accatctcgg    68220
ctcactgcaa cctccacctc ccggttcaag caattctcct gcctcagcct cccgagtagc    68280
tgggattatg ggcttgtgcc accatgccca gctgattttt gtattttttg tagagaaagg    68340
gtttcgccat gttggccagg ctggcctcga actcctgacc tcaggtgatc tgcccacttc    68400
agcctcccaa agtgctggga ttacaggcgt gagccactgt gcctggccta atgatgggct    68460
ctttaatgtg atcctttagg gttggcgcct tgccctagtt gctgttgaaa aaactatttt    68520
tgtccaaata gcacacacac agaaacctac caacttccct cccactttt cctaggaatt    68580 ccttctgagg gatttcttga gatggggcag aatggggctt ggaagaggga gttggagcta    68640
attgaccgtt gcctttctcc tttgttgggg tcctgagtct tgttcctgct gtaagagtta    68700
ctcacttcct gtctgccacc tatctccctt tgcatgtgtg cttcagttgg gagatctgtt    68760
tatcagcccc tgccacacgg ctctttgttc cttctgcaga ggacgttggg gtcccacggc    68820
tggtcctttt gactcatttt gctttcaagg tcccacctcc cagtctgagg ctgcatcctc    68880
cattaccatc gcccttcctg tgggctggga ggccaggtcc tttcctgccc agcgatgtca    68940
gcgtttcctc aggggccagg cactcatcag gagaaaggaa ctaattactt gagtaatttg    69000
ccttgccttg ctgagaggag tgtgccctga gggactccat gtgagtgtgg tgacgggtgt    69060
```

```
gggggtgtcc ctgtgttatt ttaaaatggg tgccttcagg acgatgagca tgtgaccatt   69120
tcctctctat ttccatcaca agagtattat ggtatgaggg tctcaggtta gattatcctc   69180
ccaagactct tctctcttcc ttctctactg gaagcccaca tagcatttcc ttatggcttg   69240
agggagaggt tcggagccac ttacaaatta gataaagtac atttacaatc ttgtacaaag   69300
ccacacaatg aagtcatttt tctcagcttt tttttttttt tttttttttt ttttgagcct   69360
gagtctcgct ctatcgtcca gactggagtg cagtggcgcg atcttgcttc actgaaacct   69420
ctgcctccca ggttcaagag attctcatac ctcagcctcc tgagtagctg ggattacaga   69480
catgcaccac tatgcctggc taattttttgg attttttagta gagaccgggt ttcaccctgt   69540
tggccaggct ggtctcgaac ccctgacctc aagtgatctt cccgcctggg cctcccaaag   69600
tgctgggatt ataggtgtga gccacagtgc ccagccttgt ttttgttttt gttttgtttt   69660
gacagtctgt cactctgtca cccaggctgg agtgcagtgg tgcgatctca cctcacttca   69720
gcctctgcct cccaggttca agtgattctc ctgtctcagc ctcctgagta gctgggatta   69780
caggcgtgcc accacgccca gctatttttg taatttcatt aaagacaggg tttccccatg   69840
ttggtgaggc tggtcttgaa ctcctggcct caagtgatcc acctgcttca gcctcccaaa   69900
gtgcagggat tacaggcatg agccactgtg cctggcctca gctatcttga atgctggaga   69960
attaaatcct tttctgtcta gggtgtcagc tccctaaggg ctgggccaaa acagttggat   70020
ttataagaca ctagagtctt gcctcagtag ctcctttgaa ttctgcactg aattgatcag   70080
tttcttggcc caaagtaaac tcagatggca gcccaagagc cactctgcag tgccttcttt   70140
cacatggtca tcatgctctc tgatccctca ggttctgtct aagcctcatg ttttatgacc   70200
gtgctgttct cagcccacct caccctgccc catgccttct caatggtttg ttcacctgaa   70260
ttccccagat ttcatgccag tatccccaag gttccttgac ctcttggtgt aagcattcag   70320
catctaaaat tcattttatt cccgtcaacg catttctaac tgtagaacaa gaattataaa   70380
tgacaaagct catagaaaat tggcaccttg tcttcccct ccctcttatt ttatacataa   70440
aagagaatat gggctgggca ttgtggccaa ggctgggcat gatagctcat acttgtaatc   70500
cagcactttg ggagggtgag gcagatggat cacctgaggt caggagttca agaccagcct   70560
ggccaacatg gtgaaaccctc atctctacta aaattacaaa aaaaaaatta gctaggcatg   70620
gtggcagatg cctgtaatcc agctactcag gaggctgatg aaggagaatc acttgaaccc   70680
tggaggcaga ggttgtagag agccaagatg gcgctactgc actccaacct gggcgaaaga   70740
gagcaagact ccgtctcaaa aaaaaaaaag acaaaaatta gccaggcatg gtggtgccac   70800
ctgtagtccc agctgcttgg gagcctaagg caggagaatc gttttgacct gggagtagga   70860
ggttgcggta accgagattg tgccactgca cttgagcctg gcaacagag tgagactctg   70920 tctcaaaaca ataagaacaa cagcaacaaa agagagagac catgccttgc tccaggtctc   70980
ttagctattg aagatgtacc tggacccagg tctccggtct tctagttgaa gcaattgtac   71040
tgccttacaa agtcacattc tctttggtgc ttttttgattg acgtatttat ccaactagaa   71100
agttactcat gccctcatcc aaaaatgtgg tagaggccag attagtgctg gtaggaataa   71160
gagatataac ctttggctttt ggaaccacaa gcattagcag tctccatgtt ctttaaagac   71220 ttggtgtatat tggtatttag gctggacacc atgcaaagac tacacaggct cggttcctgc   71280
atgcagagaa gttatctaag agatatgacc aggccggaat agaatgctca gaccacgtgg   71340
aggctgttaa acttttacat aatctaggga aagaagggac acaaggtggc attagtctag   71400
ggtcaggtgg gaaaaggtta tgctgaaaag tctctgcagc tcaggacagc tttgtgcaaa   71460
```

```
gaactgaagt tcacagctgc tagtgcctgg gagatcaaat agtataaatg agggcagaca   71520
accctgaggg gcagatggag cttccagac  aatcttggca tgaggatgag tgagtttcaa   71580
atcagtcctg ccgaggcaga tggcttcctc cagctctgct tactgaatgc gaagtcacag   71640
tcagtaagaa aactggtttt cttcttccca ggcgctgccc catacctgaa gaccaagttt   71700
atctgtgtga caccgtaagt ggcttccttt ccccgttttg ccttcatttc taatatcctc   71760
agttatccct gggaatggga cactgggtga gagttaatct gccaaaggtt ggaagcccct   71820
gggctatgtt tagtactcaa agtgaccttg tgtgtttaaa aagcttgagc ttttattttt   71880
ctgttggaga ccagagtttg atggcttgtg tgtgtgtgtt ttgttctttt ttttttttcc   71940
attgtgtctt gtcaaccccc cgtttcccct cctgctgccc cccatttcct acagaacgac   72000
ctgcagcaat accattgacc tgccgatgtc cccccgcact ttagattcat tgatgcagtt   72060
tggaaataat ggtgaaggtg ctgaaccctc agcaggaggg cagtttggtg agtatttggt   72120
tgacagactt tgtccctata agggaagttg gtccccttg  tgtgatgctc tcacatgtac   72180
acaccgagag ctggtcactc ggaatggtag gagattctag agctttgctt tccaaaagag   72240
atggtatgaa tgccacatgt gtgagtataa atcttctagc agccacactg gaaatagacg   72300
aacttaattt ttacaatata ttttatttaa cccactaaat ccaacatact ctcaatttaa   72360
catttcagaa aaagttgagg ctgggtgagt ggctcatgcc tgtaatccca gcactttggg   72420
aggccgaggt gggtggatca cttgaggtca ggagttcgag accagtctga ccaaaatctc   72480
taaaatataa aaattagctg gcatggtgg  cgcatacctg taatcccagc tactcaagaa   72540
gctgaggtgg gaggatcgct tgagcctggg aggtggaggt tgcagtgagc agagatcgtg   72600
ccactgcact ccagcctggg cgacagagtg agactccatc tcaaataaac aaaactaaac   72660
taaaagaaa  aagttgagac cttttttat  tctttttttt catactaagc ctttaaaatc   72720
cagtgggctt ttgacagcca cagcacagct cagtttggac aaaccaaatc tcaaatgctt   72780
ggtggccacg tgtgtctcgg ggctcctgaa ttaaacagta gatcaagggc agaagatctc   72840
aggacagcct tagagcttct gtaaacatgg agctctggga atcagttaag gtgggaatga   72900
gaaaggaccc ttcccgaggc agggtcctcc agggaggagg gtaaatctgg cttttctgac   72960
catccctggg ccttaagggg caggagattg gatagcagtg gtagcctggg ccctgtcctc   73020
tgaagggctg ggggcgtggc ctgccagttg cagagggtgg acaactgaac tagttttccc   73080
tgtctgtccc tccagagtcc ctcacctttg acatggagtt gacctcggag tgcgctacct   73140
cccccatgtg aggagctgag aacggaagct gcagaaagat acgactgagg cgcctacctg   73200
cattctgcca cccctcacac agccaaaccc cagatcatct gaaactacta actttgtggt   73260
tccagatttt ttttaatctc ctacttctgc tatctttgag caatctgggc acttttaaaa   73320
atagagaaat gagtgaatgt gggtgatctg cttttatcta aatgcaaata aggatgtgtt   73380
ctctgagacc catgatcagg ggatgtggcg ggggtggct  agagggagaa aaaggaaatg   73440
tcttgtgttg ttttgttccc ctgccctcct ttctcagcag cttttgtta  ttgttgttgt   73500
tgttcttaga caagtgcctc ctggtgcctg cggcatcctt ctgcctgttt ctgtaagcaa   73560
atgccacagg ccacctatag ctacatactc ctggcattgc acttttaac  cttgctgaca   73620
tccaaataga agataggact atctaagccc taggtttctt tttaaattaa gaataataa   73680
caattaaagg gcaaaaaaca ctgtatcagc atagcctttc tgtatttaag aaacttaagc   73740
agccgggcat ggtggctcac gcctgtaatc ccagcacttt gggaggccga ggcggatcat   73800
aaggtcagga gatcaagacc atcctggcta acacggtgaa accccgtctc tactaaaagt   73860
```

```
acaaaaaatt agctgggtgt ggtggtgggc gcctgtagtc ccagctactc gggaggctga      73920
ggcaggagaa tcgcttgaac ctgagaggcg gaggttgcag tgagccaaaa ttgcaccact      73980
gcacactgca ctccatcctg ggcgacagtc tgagactctg tctcaaaaaa aaaaaaaaaa      74040
aaaagaaact tcagttaaca gcctccttgg tgctttaagc attcagcttc cttcaggctg      74100
gtaatttata taatccctga aacgggcttc aggtcaaacc cttaagacat ctgaagctgc      74160
aacctggcct ttggtgttga aataggaagg tttaaggaga atctaagcat tttagacttt      74220 ttttataaa tagacttatt ttcctttgta atgtattggc cttttagtga gtaaggctgg       74280
gcagagggtg cttacaacct tgactcccctt tctccctgga cttgatctgc tgtttcagag     74340
gctaggttgt ttctgtgggt gccttatcag ggctgggata cttctgattc tggcttcctt     74400
cctgccccac cctcccgacc ccag                                              74424

<210> SEQ ID NO 154
<211> LENGTH: 3455
<212> TYPE: DNA
<213> ORGANISM: H. sapiens
<220> FEATURE:
<221> NAME/KEY: CDS
<222> LOCATION: (241)...(2553)

<400> SEQUENCE: 154
ggtttccgga gctgcggcgg cgcagactgg gaggggagc cggggggttcc gacgtcgcag        60 ccgagggaac aagccccaac cggatcctgg acaggcaccc cggcttggcg ctgtctctcc      120
ccctcggctc ggagaggccc ttcggcctga gggagcctcg ccgcccgtcc ccggcacacg      180
cgcagccccg gcctctcggc ctctgccgga gaaacagttg ggaccctga ttttagcagg       240 atg gcc caa tgg aat cag cta cag cag ctt gac aca cgg tac ctg gag       288
Met Ala Gln Trp Asn Gln Leu Gln Gln Leu Asp Thr Arg Tyr Leu Glu
1               5                  10                  15 cag ctc cat cag ctc tac agt gac agc ttc cca atg gag ctg cgg cag       336
Gln Leu His Gln Leu Tyr Ser Asp Ser Phe Pro Met Glu Leu Arg Gln
            20                  25                  30 ttt ctg gcc cct tgg att gag agt caa gat tgg gca tat gcg gcc agc       384
Phe Leu Ala Pro Trp Ile Glu Ser Gln Asp Trp Ala Tyr Ala Ala Ser
        35                  40                  45 aaa gaa tca cat gcc act ttg gtg ttt cat aat ctc ctg gga gag att       432
Lys Glu Ser His Ala Thr Leu Val Phe His Asn Leu Leu Gly Glu Ile
    50                  55                  60 gac cag cag tat agc cgc ttc ctg caa gag tcg aat gtt ctc tat cag       480
Asp Gln Gln Tyr Ser Arg Phe Leu Gln Glu Ser Asn Val Leu Tyr Gln
65                  70                  75                  80 cac aat cta cga aga atc aag cag ttt ctt cag agc agg tat ctt gag       528
His Asn Leu Arg Arg Ile Lys Gln Phe Leu Gln Ser Arg Tyr Leu Glu
                85                  90                  95 aag cca atg gag att gcc cgg att gtg gcc cgg tgc ctg tgg gaa gaa       576
Lys Pro Met Glu Ile Ala Arg Ile Val Ala Arg Cys Leu Trp Glu Glu
            100                 105                 110 tca cgc ctt cta cag act gca gcc act gcg gcc cag caa ggg ggc cag       624
Ser Arg Leu Leu Gln Thr Ala Ala Thr Ala Ala Gln Gln Gly Gly Gln
        115                 120                 125 gcc aac cac ccc aca gca gcc gtg gtg acg gag aag cag cag atg ctg       672
Ala Asn His Pro Thr Ala Ala Val Val Thr Glu Lys Gln Gln Met Leu
    130                 135                 140 gag cag cac ctt cag gat gtc cgg aag aga gtg cag gat cta gaa cag       720
Glu Gln His Leu Gln Asp Val Arg Lys Arg Val Gln Asp Leu Glu Gln
145                 150                 155                 160 aaa atg aaa gtg gta gag aat ctc cag gat gac ttt gat ttc aac tat       768
```

```
Lys Met Lys Val Val Glu Asn Leu Gln Asp Asp Phe Asp Phe Asn Tyr
                165                 170                 175 aaa acc ctc aag agt caa gga gac atg caa gat ctg aat gga aac aac      816
Lys Thr Leu Lys Ser Gln Gly Asp Met Gln Asp Leu Asn Gly Asn Asn
                180                 185                 190 cag tca gtg acc agg cag aag atg cag cag ctg gaa cag atg ctc act      864
Gln Ser Val Thr Arg Gln Lys Met Gln Gln Leu Glu Gln Met Leu Thr
                195                 200                 205 gcg ctg gac cag atg cgg aga agc atc gtg agt gag ctg gcg ggg ctt      912
Ala Leu Asp Gln Met Arg Arg Ser Ile Val Ser Glu Leu Ala Gly Leu
                210                 215                 220 ttg tca gcg atg gag tac gtg cag aaa act ctc acg gac gag gag ctg      960
Leu Ser Ala Met Glu Tyr Val Gln Lys Thr Leu Thr Asp Glu Glu Leu
225                 230                 235                 240 gct gac tgg aag agg cgg caa cag att gcc tgc att gga ggc ccg ccc     1008
Ala Asp Trp Lys Arg Arg Gln Gln Ile Ala Cys Ile Gly Gly Pro Pro
                245                 250                 255 aac atc tgc cta gat cgg cta gaa aac tgg ata acg tca tta gca gaa     1056
Asn Ile Cys Leu Asp Arg Leu Glu Asn Trp Ile Thr Ser Leu Ala Glu
                260                 265                 270 tct caa ctt cag acc cgt caa caa att aag aaa ctg gag gag ttg cag     1104
Ser Gln Leu Gln Thr Arg Gln Gln Ile Lys Lys Leu Glu Glu Leu Gln
                275                 280                 285 caa aaa gtt tcc tac aaa ggg gac ccc att gta cag cac cgg ccg atg     1152
Gln Lys Val Ser Tyr Lys Gly Asp Pro Ile Val Gln His Arg Pro Met
                290                 295                 300 ctg gag gag aga atc gtg gag ctg ttt aga aac tta atg aaa agt gcc     1200
Leu Glu Glu Arg Ile Val Glu Leu Phe Arg Asn Leu Met Lys Ser Ala
305                 310                 315                 320 ttt gtg gtg gag cgg cag ccc tgc atg ccc atg cat cct gac cgg ccc     1248
Phe Val Val Glu Arg Gln Pro Cys Met Pro Met His Pro Asp Arg Pro
                325                 330                 335 ctc gtc atc aag acc ggc gtc cag ttc act act aaa gtc agg ttg ctg     1296
Leu Val Ile Lys Thr Gly Val Gln Phe Thr Thr Lys Val Arg Leu Leu
                340                 345                 350 gtc aaa ttc cct gag ttg aat tat cag ctt aaa att aaa gtg tgc att     1344
Val Lys Phe Pro Glu Leu Asn Tyr Gln Leu Lys Ile Lys Val Cys Ile
                355                 360                 365 gac aaa gac tct ggg gac gtt gca gct ctc aga gga tcc cgg aaa ttt     1392
Asp Lys Asp Ser Gly Asp Val Ala Ala Leu Arg Gly Ser Arg Lys Phe
                370                 375                 380 aac att ctg ggc aca aac aca aaa gtg atg aac atg gaa gaa tcc aac     1440
Asn Ile Leu Gly Thr Asn Thr Lys Val Met Asn Met Glu Glu Ser Asn
385                 390                 395                 400 aac ggc agc ctc tct gca gaa ttc aaa cac ttg acc ctg agg gag cag     1488
Asn Gly Ser Leu Ser Ala Glu Phe Lys His Leu Thr Leu Arg Glu Gln
                405                 410                 415 aga tgt ggg aat ggg ggc cga gcc aat tgt gat gct tcc ctg att gtg     1536
Arg Cys Gly Asn Gly Gly Arg Ala Asn Cys Asp Ala Ser Leu Ile Val
                420                 425                 430 act gag gag ctg cac ctg atc acc ttt gag acc gag gtg tat cac caa     1584
Thr Glu Glu Leu His Leu Ile Thr Phe Glu Thr Glu Val Tyr His Gln
                435                 440                 445 ggc ctc aag att gac cta gag acc cac tcc ttg cca gtt gtg gtg atc     1632
Gly Leu Lys Ile Asp Leu Glu Thr His Ser Leu Pro Val Val Val Ile
                450                 455                 460 tcc aac atc tgt cag atg cca aat gcc tgg gcg tcc atc ctg tgg tac     1680
Ser Asn Ile Cys Gln Met Pro Asn Ala Trp Ala Ser Ile Leu Trp Tyr
465                 470                 475                 480 aac atg ctg acc aac aat ccc aag aat gta aac ttt ttt acc aag ccc     1728
```

```
                Asn Met Leu Thr Asn Asn Pro Lys Asn Val Asn Phe Phe Thr Lys Pro
                                485                 490                 495 cca att gga acc tgg gat caa gtg gcc gag gtc ctg agc tgg cag ttc              1776
Pro Ile Gly Thr Trp Asp Gln Val Ala Glu Val Leu Ser Trp Gln Phe
            500                 505                 510 tcc tcc acc acc aag cga gga ctg agc atc gag cag ctg act aca ctg              1824
Ser Ser Thr Thr Lys Arg Gly Leu Ser Ile Glu Gln Leu Thr Thr Leu
            515                 520                 525 gca gag aaa ctc ttg gga cct ggt gtg aat tat tca ggg tgt cag atc              1872
Ala Glu Lys Leu Leu Gly Pro Gly Val Asn Tyr Ser Gly Cys Gln Ile
            530                 535                 540 aca tgg gct aaa ttt tgc aaa gaa aac atg gct ggc aag ggc ttc tcc              1920
Thr Trp Ala Lys Phe Cys Lys Glu Asn Met Ala Gly Lys Gly Phe Ser
545                 550                 555                 560 ttc tgg gtc tgg ctg gac aat atc att gac ctt gtg aaa aag tac atc              1968
Phe Trp Val Trp Leu Asp Asn Ile Ile Asp Leu Val Lys Lys Tyr Ile
                565                 570                 575 ctg gcc ctt tgg aac gaa ggg tac atc atg ggc ttt atc agt aag gag              2016
Leu Ala Leu Trp Asn Glu Gly Tyr Ile Met Gly Phe Ile Ser Lys Glu
            580                 585                 590 cgg gag cgg gcc atc ttg agc act aag cct cca ggc acc ttc ctg cta              2064
Arg Glu Arg Ala Ile Leu Ser Thr Lys Pro Pro Gly Thr Phe Leu Leu
        595                 600                 605 aga ttc agt gaa agc agc aaa gaa gga ggc gtc act ttc act tgg gtg              2112
Arg Phe Ser Glu Ser Ser Lys Glu Gly Gly Val Thr Phe Thr Trp Val
            610                 615                 620 gag aag gac atc agc ggt aag acc cag atc cag tcc gtg gaa cca tac              2160
Glu Lys Asp Ile Ser Gly Lys Thr Gln Ile Gln Ser Val Glu Pro Tyr
625                 630                 635                 640 aca aag cag cag ctg aac aac atg tca ttt gct gaa atc atc atg ggc              2208
Thr Lys Gln Gln Leu Asn Asn Met Ser Phe Ala Glu Ile Ile Met Gly
                645                 650                 655 tat aag atc atg gat gct acc aat atc ctg gtg tct cca ctg gtc tat              2256
Tyr Lys Ile Met Asp Ala Thr Asn Ile Leu Val Ser Pro Leu Val Tyr
            660                 665                 670 ctc tat cct gac att ccc aag gag gag gca ttc gga aag tat tgt cgg              2304
Leu Tyr Pro Asp Ile Pro Lys Glu Glu Ala Phe Gly Lys Tyr Cys Arg
        675                 680                 685 cca gag agc cag gag cat cct gaa gct gac cca ggt agc gct gcc cca              2352
Pro Glu Ser Gln Glu His Pro Glu Ala Asp Pro Gly Ser Ala Ala Pro
            690                 695                 700 tac ctg aag acc aag ttt atc tgt gtg aca cca acg acc tgc agc aat              2400
Tyr Leu Lys Thr Lys Phe Ile Cys Val Thr Pro Thr Thr Cys Ser Asn
705                 710                 715                 720 acc att gac ctg ccg atg tcc ccc cgc act tta gat tca ttg atg cag              2448
Thr Ile Asp Leu Pro Met Ser Pro Arg Thr Leu Asp Ser Leu Met Gln
                725                 730                 735 ttt gga aat aat ggt gaa ggt gct gaa ccc tca gca gga ggg cag ttt              2496
Phe Gly Asn Asn Gly Glu Gly Ala Glu Pro Ser Ala Gly Gly Gln Phe
            740                 745                 750 gag tcc ctc acc ttt gac atg gag ttg acc tcg gag tgc gct acc tcc              2544
Glu Ser Leu Thr Phe Asp Met Glu Leu Thr Ser Glu Cys Ala Thr Ser
        755                 760                 765 ccc atg tga ggagctgaga acggaagctg cagaaagata cgactgaggc                      2593
Pro Met
    770 gcctacctgc attctgccac ccctcacaca gccaaacccc agatcatctg aaactactaa            2653 ctttgtggtt ccagattttt tttaatctcc tacttctgct atctttgagc aatctgggca            2713 cttttaaaaa tagagaaatg agtgaatgtg ggtgatctgc ttttatctaa atgcaaataa            2773
```

-continued

```
ggatgtgttc tctgagaccc atgatcaggg gatgtggcgg ggggtggcta gagggagaaa    2833
aaggaaatgt cttgtgttgt tttgttcccc tgccctcctt tctcagcagc ttttgttat    2893 tgttgttgtt gttcttagac aagtgcctcc tggtgcctgc ggcatccttc tgcctgtttc    2953
tgtaagcaaa tgccacaggc cacctatagc tacatactcc tggcattgca cttttaacc    3013 ttgctgacat ccaaatagaa gataggacta tctaagccct aggtttcttt ttaaattaag    3073
aaataataac aattaaaggg caaaaaacac tgtatcagca tagcctttct gtatttaaga    3133
aacttaagca gccgggcatg gtggctcacg cctgtaatcc cagcactttg ggaggccgag    3193
gcggatcata aggtcaggag atcaagacca tcctggctaa cacggtgaaa ccccgtctct    3253
actaaaagta caaaaaatta gctgggtgtg gtggtgggcg cctgtagtcc cagctactcg    3313
ggaggctgag gcaggagaat cgcttgaacc tgagaggcgg aggttgcagt gagccaaaat    3373
tgcaccactg cacactgcac tccatcctgg gcgacagtct gagactctgt ctcaaaaaaa    3433
aaaaaaaaaa aaaaaaaaaa aa                                            3455

<210> SEQ ID NO 155
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 155
gtgcgcgcga gcccgaaatc                                                20

<210> SEQ ID NO 156
<211> LENGTH: 24
<212> TYPE: DNA
<213> ORGANISM: Artificial Sequence
<220> FEATURE:
<223> OTHER INFORMATION: PCR Primer

<400> SEQUENCE: 156
acatgccact ttggtgtttc ataa                                           24

<210> SEQ ID NO 157
<211> LENGTH: 27
<212> TYPE: DNA
<213> ORGANISM: Artificial Sequence
<220> FEATURE:
<223> OTHER INFORMATION: PCR Primer

<400> SEQUENCE: 157
tcttcgtaga ttgtgctgat agagaac                                        27

<210> SEQ ID NO 158
<211> LENGTH: 29
<212> TYPE: DNA
<213> ORGANISM: Artificial Sequence
<220> FEATURE:
<223> OTHER INFORMATION: PCR Probe

<400> SEQUENCE: 158
cagtatagcc gcttcctgca agagtcgaa                                      29

<210> SEQ ID NO 159
<211> LENGTH: 20
<212> TYPE: DNA
<213> ORGANISM: Artificial Sequence
<220> FEATURE:
<223> OTHER INFORMATION: Antisense oligonucleotide
```

<400> SEQUENCE: 159
agcctctgca ccctcatgtt                                          20

<210> SEQ ID NO 160
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 160
ctcctaaatt aagaacttct                                          20

<210> SEQ ID NO 161
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 161
ttttgcatga tgtaaccact                                          20

<210> SEQ ID NO 162
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 162
tattgaaaat tatctaattc                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 163
ttgggccatc ctgctaaaat                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 164
attcacttgc ctccttgact                                          20

<210> SEQ ID NO 165
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 165
atgcccttac tctccgcatc                                          20

<210> SEQ ID NO 166
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 166
ctgaacttac cctctgagag                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 167
aaatgcggac ccaagagttt                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 168
cttgttccct cggctgcgac                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 169
gcctgtccag gatccggttg                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 170
gaagggcctc tccgagccga                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 171
ggcggcgagg ctccctcagg                                              20

<210> SEQ ID NO 172
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 172
tccggcagag gccgagaggc                                              20
```

<210> SEQ ID NO 173
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 173
ccatcctgct aaaatcaggg                                          20

<210> SEQ ID NO 174
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 174
ccattgggcc atcctgctaa                                          20

<210> SEQ ID NO 175
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 175
tgtcaagctg ctgtagctga                                          20

<210> SEQ ID NO 176
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 176
aactgccgca gctccattgg                                          20

<210> SEQ ID NO 177
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 177
tcttgactct caatccaagg                                          20

<210> SEQ ID NO 178
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 178
cgcatatgcc caatcttgac                                          20

<210> SEQ ID NO 179
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 179
cgactcttgc aggaagcggc                                               20

<210> SEQ ID NO 180
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 180
tcgtagattg tgctgataga                                               20

<210> SEQ ID NO 181
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 181
agaaactgct tgattcttcg                                               20

<210> SEQ ID NO 182
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 182
gatacctgct ctgaagaaac                                               20

<210> SEQ ID NO 183
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 183
ttctcaagat acctgctctg                                               20

<210> SEQ ID NO 184
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 184
ttggcttctc aagatacctg                                               20

<210> SEQ ID NO 185
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 185
gtgattcttc ccacaggcac                                               20

<210> SEQ ID NO 186
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 186
atctgctgct tctccgtcac                                              20

<210> SEQ ID NO 187
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 187
ccagcatctg ctgcttctcc                                              20

<210> SEQ ID NO 188
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 188
tgaaggtgct gctccagcat                                              20

<210> SEQ ID NO 189
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 189
ttctgttcta gatcctgcac                                              20

<210> SEQ ID NO 190
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 190
ctggagattc tctaccactt                                              20

<210> SEQ ID NO 191
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 191
aagtcatcct ggagattctc                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 192
aatcaaagtc atcctggaga                                              20
```

```
<210> SEQ ID NO 193
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 193
gttgaaatca aagtcatcct                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 194
ttatagttga aatcaaagtc                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 195 gggtttttata gttgaaatca                                             20

<210> SEQ ID NO 196
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 196
cttgagggtt ttatagttga                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 197
tgactcttga gggtttttata                                             20

<210> SEQ ID NO 198
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 198
ctccttgact cttgagggtt                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense oligonucleotide
```

<400> SEQUENCE: 199
catgtctcct tgactcttga                    20

<210> SEQ ID NO 200
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 200
attcagatct tgcatgtctc                    20

<210> SEQ ID NO 201
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 201
tggttgtttc cattcagatc                    20

<210> SEQ ID NO 202
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 202
tggtcactga ctggttgttt                    20

<210> SEQ ID NO 203
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 203
tccagctgct gcatcttctg                    20

<210> SEQ ID NO 204
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 204
gagcatctgt tccagctgct                    20

<210> SEQ ID NO 205
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 205
cttctccgca tctggtccag                    20

<210> SEQ ID NO 206
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 206
ttctgcacgt actccatcgc                                                 20

<210> SEQ ID NO 207
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 207
cagccagctc ctcgtccgtg                                                 20

<210> SEQ ID NO 208
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 208
ctcttccagt cagccagctc                                                 20

<210> SEQ ID NO 209
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 209
tgccgcctct tccagtcagc                                                 20

<210> SEQ ID NO 210
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 210
ccagttttct agccgatcta                                                 20

<210> SEQ ID NO 211
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 211
acgttatcca gttttctagc                                                 20

<210> SEQ ID NO 212
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 212
agttgagatt ctgctaatga                                                 20
```

<210> SEQ ID NO 213
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 213
tctgaagttg agattctgct                                              20

<210> SEQ ID NO 214
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 214
cctttgtagg aaacttttg                                               20

<210> SEQ ID NO 215
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 215
aggcactttt cattaagttt                                              20

<210> SEQ ID NO 216
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 216
ttgaccagca acctgactt                                               20

<210> SEQ ID NO 217
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 217
agctgataat tcaactcagg                                              20

<210> SEQ ID NO 218
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 218
ttttaagctg ataattcaac                                              20

<210> SEQ ID NO 219
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 219
ctttaatttt aagctgataa                                          20

<210> SEQ ID NO 220
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 220
gcacacttta attttaagct                                          20

<210> SEQ ID NO 221
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 221
tcaatgcaca ctttaatttt                                          20

<210> SEQ ID NO 222
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 222
cccagaatgt taaatttccg                                          20

<210> SEQ ID NO 223
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 223
agaggctgcc gttgttggat                                          20

<210> SEQ ID NO 224
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 224
aagtgtttga attctgcaga                                          20

<210> SEQ ID NO 225
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 225
tctctgctcc ctcagggtca                                          20

<210> SEQ ID NO 226
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 226
atcaggtgca gctcctcagt                                              20

<210> SEQ ID NO 227
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 227
aggtgatcag gtgcagctcc                                              20

<210> SEQ ID NO 228
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 228
ctcaaaggtg atcaggtgca                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 229
gaggccttgg tgatacacct                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 230
tcaatcttga ggccttggtg                                              20

<210> SEQ ID NO 231
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 231
ctaggtcaat cttgaggcct                                              20

<210> SEQ ID NO 232
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 232
ggtctctagg tcaatcttga                                              20
```

<210> SEQ ID NO 233
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 233
aaggagtggg tctctaggtc                                        20

<210> SEQ ID NO 234
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 234
ctggcaagga gtgggtctct                                        20

<210> SEQ ID NO 235
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 235
accacaactg gcaaggagtg                                        20

<210> SEQ ID NO 236
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 236
tctgacagat gttggagatc                                        20

<210> SEQ ID NO 237
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 237
tggcatctga cagatgttgg                                        20

<210> SEQ ID NO 238
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 238
gcatttggca tctgacagat                                        20

<210> SEQ ID NO 239
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 239
ttcttgggat tgttggtcag                                             20

<210> SEQ ID NO 240
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 240
gtcagctgct cgatgctcag                                             20

<210> SEQ ID NO 241
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 241
tcccaagagt ttctctgcca                                             20

<210> SEQ ID NO 242
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 242
catgtgatct gacaccctga                                             20

<210> SEQ ID NO 243
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 243
tagcccatgt gatctgacac                                             20

<210> SEQ ID NO 244
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 244
gccatgtttt ctttgcaaaa                                             20

<210> SEQ ID NO 245
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 245
ccttgccagc catgttttct                                             20

<210> SEQ ID NO 246
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 246
gaagcccttg ccagccatgt                                               20

<210> SEQ ID NO 247
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 247
aaggagaagc ccttgccagc                                               20

<210> SEQ ID NO 248
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 248
cccagaagga gaagcccttg                                               20

<210> SEQ ID NO 249
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 249
tccagccaga cccagaagga                                               20

<210> SEQ ID NO 250
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 250
tctttgctgc tttcactgaa                                               20

<210> SEQ ID NO 251
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 251
atgttgttca gctgctgctt                                               20

<210> SEQ ID NO 252
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 252
atgacatgtt gttcagctgc                                               20
```

```
<210> SEQ ID NO 253
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 253
agcaaatgac atgttgttca                                                   20

<210> SEQ ID NO 254
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 254
atttcagcaa atgacatgtt                                                   20

<210> SEQ ID NO 255
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 255
tgatgatttc agcaaatgac                                                   20

<210> SEQ ID NO 256
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 256
ttatagccca tgatgatttc                                                   20

<210> SEQ ID NO 257
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 257
tgatcttata gcccatgatg                                                   20

<210> SEQ ID NO 258
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 258
atccatgatc ttatagccca                                                   20

<210> SEQ ID NO 259
<211> LENGTH: 20
<212> TYPE: DNA
<213> ORGANISM: Artificial Sequence
<220> FEATURE:
<223> OTHER INFORMATION: Antisense oligonucleotide
```

<400> SEQUENCE: 259
ggtagcatcc atgatcttat                                           20

<210> SEQ ID NO 260
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 260
aatgtcagga tagagataga                                           20

<210> SEQ ID NO 261
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 261
gcctcctcct tgggaatgtc                                           20

<210> SEQ ID NO 262
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 262
tccgaatgcc tcctccttgg                                           20

<210> SEQ ID NO 263
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 263
tactttccga atgcctcctc                                           20

<210> SEQ ID NO 264
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 264
gacaatactt tccgaatgcc                                           20

<210> SEQ ID NO 265
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 265
ctacctgggt cagcttcagg                                           20

<210> SEQ ID NO 266
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 266
ataaacttgg tcttcaggta                                                    20

<210> SEQ ID NO 267
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 267
gtcgttggtg tcacacagat                                                    20

<210> SEQ ID NO 268
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 268
tgcaggtcgt tggtgtcaca                                                    20

<210> SEQ ID NO 269
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 269
attgctgcag gtcgttggtg                                                    20

<210> SEQ ID NO 270
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 270
atggtattgc tgcaggtcgt                                                    20

<210> SEQ ID NO 271
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 271
ggtcaatggt attgctgcag                                                    20

<210> SEQ ID NO 272
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 272
gacatcggca ggtcaatggt                                                    20
```

```
<210> SEQ ID NO 273
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 273
caatgaatct aaagtgcggg                                                    20

<210> SEQ ID NO 274
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 274
tgcatcaatg aatctaaagt                                                    20

<210> SEQ ID NO 275
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 275
caaactgcat caatgaatct                                                    20

<210> SEQ ID NO 276
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 276
atttccaaac tgcatcaatg                                                    20

<210> SEQ ID NO 277
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 277
aactgccctc ctgctgaggg                                                    20

<210> SEQ ID NO 278
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 278
ggtgagggac tcaaactgcc                                                    20

<210> SEQ ID NO 279
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 279
cagtcgtatc tttctgcagc                                         20

<210> SEQ ID NO 280
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 280
agatagcaga agtaggagat                                         20

<210> SEQ ID NO 281
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 281
aaagtgccca gattgctcaa                                         20

<210> SEQ ID NO 282
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 282
tttttaaaag tgcccagatt                                         20

<210> SEQ ID NO 283
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 283
cagatcaccc acattcactc                                         20

<210> SEQ ID NO 284
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 284
tgcatttaga taaaagcaga                                         20

<210> SEQ ID NO 285
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 285
gaacacatcc ttatttgcat                                         20

<210> SEQ ID NO 286
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 286
atcatgggtc tcagagaaca                                                   20

<210> SEQ ID NO 287
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 287
cacatcccct gatcatgggt                                                   20

<210> SEQ ID NO 288
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 288
agacatttcc ttttctccc                                                    20

<210> SEQ ID NO 289
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 289
accaggaggc acttgtctaa                                                   20

<210> SEQ ID NO 290
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 290
gcaggcacca ggaggcactt                                                   20

<210> SEQ ID NO 291
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 291
gcttacagaa acaggcagaa                                                   20

<210> SEQ ID NO 292
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 292
aggtggcctg tggcatttgc                                                   20
```

<210> SEQ ID NO 293
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 293
gtatgtagct ataggtggcc                                             20

<210> SEQ ID NO 294
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 294
gcaatgccag gagtatgtag                                             20

<210> SEQ ID NO 295
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 295
ttaaaaagtg caatgccagg                                             20

<210> SEQ ID NO 296
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 296
ggcttagata gtcctatctt                                             20

<210> SEQ ID NO 297
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 297
taaaaagaaa cctagggctt                                             20

<210> SEQ ID NO 298
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 298
atacagaaag gctatgctga                                             20

<210> SEQ ID NO 299
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 299
ttaagtttct taaatacaga                                              20

<210> SEQ ID NO 300
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 300
gcatctgctg cttctccgtc                                              20

<210> SEQ ID NO 301
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 301
cagcatctgc tgcttctccg                                              20

<210> SEQ ID NO 302
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 302
tccagcatct gctgcttctc                                              20

<210> SEQ ID NO 303
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 303
ctccagcatc tgctgcttct                                              20

<210> SEQ ID NO 304
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 304
tgctccagca tctgctgctt                                              20

<210> SEQ ID NO 305
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 305
tgctgctcca gcatctgctg                                              20

<210> SEQ ID NO 306
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 306
ggtgctgctc cagcatctgc                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 307
aaggtgctgc tccagcatct                                               20

<210> SEQ ID NO 308
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 308
tgggattgtt ggtcagcatg                                               20

<210> SEQ ID NO 309
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 309
attcttggga ttgttggtca                                               20

<210> SEQ ID NO 310
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 310
acattcttgg gattgttggt                                               20

<210> SEQ ID NO 311
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 311
cacattcttg ggattgttgg                                               20

<210> SEQ ID NO 312
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 312
ttcacattct tgggattgtt                                               20
```

```
<210> SEQ ID NO 313
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 313
agttcacatt cttgggattg                                         20

<210> SEQ ID NO 314
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 314
gaagttcaca ttcttgggat                                         20

<210> SEQ ID NO 315
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 315
agattatgaa acaccaaagt                                         20

<210> SEQ ID NO 316
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 316
ggagattatg aaacaccaaa                                         20

<210> SEQ ID NO 317
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 317
caggagatta tgaaacacca                                         20

<210> SEQ ID NO 318
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 318
tcccaggaga ttatgaaaca                                         20

<210> SEQ ID NO 319
<211> LENGTH: 20
<212> TYPE: DNA
<213> ORGANISM: Artificial Sequence
<220> FEATURE:
<223> OTHER INFORMATION: Antisense oligonucleotide
```

-continued

<400> SEQUENCE: 319
ctcccaggag attatgaaac                                              20

<210> SEQ ID NO 320
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 320
ctctcccagg agattatgaa                                              20

<210> SEQ ID NO 321
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 321
atctctccca ggagattatg                                              20

<210> SEQ ID NO 322
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 322
cttgccagcc atgttttctt                                              20

<210> SEQ ID NO 323
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 323
cccttgccag ccatgttttc                                              20

<210> SEQ ID NO 324
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 324
agcccttgcc agccatgttt                                              20

<210> SEQ ID NO 325
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 325
gagaagccct tgccagccat                                              20

<210> SEQ ID NO 326
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 326
aggagaagcc cttgccagcc                                              20

<210> SEQ ID NO 327
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 327
gaaggagaag cccttgccag                                              20

<210> SEQ ID NO 328
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 328
aagcccttgc cagccatgtt                                              20

<210> SEQ ID NO 329
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 329
agaagccctt gccagccatg                                              20

<210> SEQ ID NO 330
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 330
agaaggagaa gcccttgcca                                              20

<210> SEQ ID NO 331
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 331
ccagaaggag aagcccttgc                                              20

<210> SEQ ID NO 332
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 332
acccagaagg agaagccctt                                              20
```

<210> SEQ ID NO 333
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 333
tgcctcctcc ttgggaatgt                                               20

<210> SEQ ID NO 334
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 334
aatgcctcct ccttgggaat                                               20

<210> SEQ ID NO 335
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 335
cgaatgcctc ctccttggga                                               20

<210> SEQ ID NO 336
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 336
ttccgaatgc ctcctccttg                                               20

<210> SEQ ID NO 337
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 337
tttccgaatg cctcctcctt                                               20

<210> SEQ ID NO 338
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 338
actttccgaa tgcctcctcc                                               20

<210> SEQ ID NO 339
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 339
ttgcaggaag cggctatact                                          20

<210> SEQ ID NO 340
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 340
tcttgcagga agcggctata                                          20

<210> SEQ ID NO 341
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 341
actcttgcag gaagcggcta                                          20

<210> SEQ ID NO 342
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 342
gactcttgca ggaagcggct                                          20

<210> SEQ ID NO 343
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 343
tcgactcttg caggaagcgg                                          20

<210> SEQ ID NO 344
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 344
ttcgactctt gcaggaagcg                                          20

<210> SEQ ID NO 345
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 345
cattcgactc ttgcaggaag                                          20

<210> SEQ ID NO 346
<211> LENGTH: 20

-continued

```
<212> TYPE: DNA
<213> ORGANISM: Artificial Sequence
<220> FEATURE:
<223> OTHER INFORMATION: Antisense oligonucleotide

<400> SEQUENCE: 346
tcttatagcc catgatgatt                                               20

<210> SEQ ID NO 347
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 347
gatcttatag cccatgatga                                               20

<210> SEQ ID NO 348
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 348
atgatcttat agcccatgat                                               20

<210> SEQ ID NO 349
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 349
ccatgatctt atagcccatg                                               20

<210> SEQ ID NO 350
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 350
gcatccatga tcttatagcc                                               20

<210> SEQ ID NO 351
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 351
tagcatccat gatcttatag                                               20

<210> SEQ ID NO 352
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 352
gtagcatcca tgatcttata                                               20
```

<210> SEQ ID NO 353
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 353
aaaggctatg ctgatacagt                                               20

<210> SEQ ID NO 354
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 354
agaaaggcta tgctgataca                                               20

<210> SEQ ID NO 355
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 355
acagaaaggc tatgctgata                                               20

<210> SEQ ID NO 356
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 356
tacagaaagg ctatgctgat                                               20

<210> SEQ ID NO 357
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 357
aatacagaaa ggctatgctg                                               20

<210> SEQ ID NO 358
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 358
aaatacagaa aggctatgct                                               20

<210> SEQ ID NO 359
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 359
ttaaatacag aaaggctatg                                          20

<210> SEQ ID NO 360
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 360
tcttaaatac agaaaggcta                                          20

<210> SEQ ID NO 361
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 361
ggtctcagag aacacatcct                                          20

<210> SEQ ID NO 362
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 362
tgggtctcag agaacacatc                                          20

<210> SEQ ID NO 363
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 363
catgggtctc agagaacaca                                          20

<210> SEQ ID NO 364
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 364
tcatgggtct cagagaacac                                          20

<210> SEQ ID NO 365
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 365
tgatcatggg tctcagagaa                                          20

<210> SEQ ID NO 366
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 366
cctgatcatg ggtctcagag                                              20

<210> SEQ ID NO 367
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 367
cccctgatca tgggtctcag                                              20

<210> SEQ ID NO 368
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 368
cagacccaga aggagaagcc                                              20

<210> SEQ ID NO 369
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 369
cagccagacc cagaaggaga                                              20

<210> SEQ ID NO 370
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 370
ccagccagac ccagaaggag                                              20

<210> SEQ ID NO 371
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 371
gtccagccag acccagaagg                                              20

<210> SEQ ID NO 372
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 372
tgtccagcca gacccagaag                                              20
```

<210> SEQ ID NO 373
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 373
attgtccagc cagacccaga                                               20

<210> SEQ ID NO 374
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 374
atattgtcca gccagaccca                                               20

<210> SEQ ID NO 375
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 375
catgatctta tagcccatga                                               20

<210> SEQ ID NO 376
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 376
tccatgatct tatagcccat                                               20

<210> SEQ ID NO 377
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 377
catccatgat cttatagccc                                               20

<210> SEQ ID NO 378
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 378
agcatccatg atcttatagc                                               20

<210> SEQ ID NO 379
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 379
tggtagcatc catgatctta                                                    20

<210> SEQ ID NO 380
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 380
ttggtagcat ccatgatctt                                                    20

<210> SEQ ID NO 381
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 381
gatattggta gcatccatga                                                    20

<210> SEQ ID NO 382
<211> LENGTH: 2924
<212> TYPE: DNA
<213> ORGANISM: M. musculus
<220> FEATURE:
<221> NAME/KEY: CDS
<222> LOCATION: (173)...(2341)

<400> SEQUENCE: 382
gtcgacccac gcgtccgcgc tgaggtacaa ccccgctcgg tgtcgcctga ccgcgtcggc        60
taggagaggc caggcggccc tcgggagccc agcagctcgc gcctggagtc agcgcaggcc       120
ggccagtcgg gcctcagccc cggagacagt cgagacccct gactgcagca gg atg gct      178
                                                          Met Ala
                                                            1 cag tgg aac cag ctg cag cag ctg gac aca cgc tac ctg gag cag ctg        226
Gln Trp Asn Gln Leu Gln Gln Leu Asp Thr Arg Tyr Leu Glu Gln Leu
          5                  10                  15 cac cag ctg tac agc gac acg ttc ccc atg gag ctg cgg cag ttc ctg        274
His Gln Leu Tyr Ser Asp Thr Phe Pro Met Glu Leu Arg Gln Phe Leu
     20                  25                  30 gca cct tgg att gag agt caa gac tgg gca tat gca gcc agc aaa gag        322
Ala Pro Trp Ile Glu Ser Gln Asp Trp Ala Tyr Ala Ala Ser Lys Glu
 35                  40                  45                  50 tca cat gcc acg ttg gtg ttt cat aat ctc ttg ggt gaa att gac cag        370
Ser His Ala Thr Leu Val Phe His Asn Leu Leu Gly Glu Ile Asp Gln
                 55                  60                  65 caa tat agc cga ttc ctg caa gag tcc aat gtc ctc tat cag cac aac        418
Gln Tyr Ser Arg Phe Leu Gln Glu Ser Asn Val Leu Tyr Gln His Asn
             70                  75                  80 ctt cga aga atc aag cag ttt ctg cag agc agg tat ctt gag aag cca        466
Leu Arg Arg Ile Lys Gln Phe Leu Gln Ser Arg Tyr Leu Glu Lys Pro
         85                  90                  95 atg gaa att gcc cgg atc gtg gcc cga tgc ctg tgg gaa gag tct cgc        514
Met Glu Ile Ala Arg Ile Val Ala Arg Cys Leu Trp Glu Glu Ser Arg
    100                 105                 110 ctc ctc cag acg gca gcc acg gca gcc cag caa ggg ggc cag gcc aac        562
Leu Leu Gln Thr Ala Ala Thr Ala Ala Gln Gln Gly Gly Gln Ala Asn
115                 120                 125                 130
```

```
cac cca aca gcc gcc gta gtg aca gag aag cag cag atg ttg gag cag     610
His Pro Thr Ala Ala Val Val Thr Glu Lys Gln Gln Met Leu Glu Gln
            135                 140                 145 cat ctt cag gat gtc cgg aag cga gtg cag gat cta gaa cag aaa atg     658
His Leu Gln Asp Val Arg Lys Arg Val Gln Asp Leu Glu Gln Lys Met
        150                 155                 160 aag gtg gtg gag aac ctc cag gac gac ttt gat ttc aac tac aaa acc     706
Lys Val Val Glu Asn Leu Gln Asp Asp Phe Asp Phe Asn Tyr Lys Thr
    165                 170                 175 ctc aag agc caa gga gac atg cag gat ctg aat gga aac aac cag tct     754
Leu Lys Ser Gln Gly Asp Met Gln Asp Leu Asn Gly Asn Asn Gln Ser
180                 185                 190 gtg acc aga cag aag atg cag cag ctg gaa cag atg ctc aca gcc ctg     802
Val Thr Arg Gln Lys Met Gln Gln Leu Glu Gln Met Leu Thr Ala Leu
195                 200                 205                 210 gac cag atg cgg aga agc att gtg agt gag ctg gcg ggg ctc ttg tca     850
Asp Gln Met Arg Arg Ser Ile Val Ser Glu Leu Ala Gly Leu Leu Ser
            215                 220                 225 gca atg gag tac gtg cag aag aca ctg act gat gaa gag ctg gct gac     898
Ala Met Glu Tyr Val Gln Lys Thr Leu Thr Asp Glu Glu Leu Ala Asp
        230                 235                 240 tgg aag agg cgg cag cag atc gcg tgc atc gga ggc cct ccc aac atc     946
Trp Lys Arg Arg Gln Gln Ile Ala Cys Ile Gly Gly Pro Pro Asn Ile
    245                 250                 255 tgc ctg gac cgt ctg gaa aac tgg ata act tca tta gca gaa tct caa     994
Cys Leu Asp Arg Leu Glu Asn Trp Ile Thr Ser Leu Ala Glu Ser Gln
260                 265                 270 ctt cag acc cgc caa caa att aag aaa ctg gag gag ctg cag cag aaa    1042
Leu Gln Thr Arg Gln Gln Ile Lys Lys Leu Glu Glu Leu Gln Gln Lys
275                 280                 285                 290 gtg tcc tac aag ggc gac cct atc gtg cag cac cgg ccc atg ctg gag    1090
Val Ser Tyr Lys Gly Asp Pro Ile Val Gln His Arg Pro Met Leu Glu
            295                 300                 305 gag agg atc gtg gag ctg ttc aga aac tta atg aag agt gcc ttc gtg    1138
Glu Arg Ile Val Glu Leu Phe Arg Asn Leu Met Lys Ser Ala Phe Val
        310                 315                 320 gtg gag cgg cag ccc tgc atg ccc atg cac ccg gac cgg ccc tta gtc    1186
Val Glu Arg Gln Pro Cys Met Pro Met His Pro Asp Arg Pro Leu Val
    325                 330                 335 atc aag act ggt gtc cag ttt acc acg aaa gtc agg ttg ctg gtc aaa    1234
Ile Lys Thr Gly Val Gln Phe Thr Thr Lys Val Arg Leu Leu Val Lys
340                 345                 350 ttt cct gag ttg aat tat cag ctt aaa att aaa gtg tgc att gat aaa    1282
Phe Pro Glu Leu Asn Tyr Gln Leu Lys Ile Lys Val Cys Ile Asp Lys
355                 360                 365                 370 gac tct ggg gat gtt gct gcc ctc aga ggg tct cgg aaa ttt aac att    1330
Asp Ser Gly Asp Val Ala Ala Leu Arg Gly Ser Arg Lys Phe Asn Ile
            375                 380                 385 ctg ggc acg aac aca aaa gtg atg aac atg gag gag tct aac aac ggc    1378
Leu Gly Thr Asn Thr Lys Val Met Asn Met Glu Glu Ser Asn Asn Gly
        390                 395                 400 agc ctg tct gca gag ttc aag cac ctg acc ctt agg gag cag aga tgt    1426
Ser Leu Ser Ala Glu Phe Lys His Leu Thr Leu Arg Glu Gln Arg Cys
    405                 410                 415 ggg aat gga ggc cgt gcc aat tgt gat gcc tcc ttg atc gtg act gag    1474
Gly Asn Gly Gly Arg Ala Asn Cys Asp Ala Ser Leu Ile Val Thr Glu
420                 425                 430 gag ctg cac ctg atc acc ttc gag act gag gtg tac cac caa ggc ctc    1522
Glu Leu His Leu Ile Thr Phe Glu Thr Glu Val Tyr His Gln Gly Leu
435                 440                 445                 450
```

```
aag att gac cta gag acc cac tcc ttg cca gtt gtg gtg atc tcc aac      1570
Lys Ile Asp Leu Glu Thr His Ser Leu Pro Val Val Val Ile Ser Asn
            455                 460                 465 atc tgt cag atg cca aat gct tgg gca tca atc ctg tgg tat aac atg      1618
Ile Cys Gln Met Pro Asn Ala Trp Ala Ser Ile Leu Trp Tyr Asn Met
                470                 475                 480 ctg acc aat aac ccc aag aac gtg aac ttc ttc act aag ccg cca att      1666
Leu Thr Asn Asn Pro Lys Asn Val Asn Phe Phe Thr Lys Pro Pro Ile
            485                 490                 495 gga acc tgg gac caa gtg gcc gag gtg ctc agc tgg cag ttc tcg tcc      1714
Gly Thr Trp Asp Gln Val Ala Glu Val Leu Ser Trp Gln Phe Ser Ser
        500                 505                 510 acc acc aag cga ggg ctg agc atc gag cag ctg aca acg ctg gct gag      1762
Thr Thr Lys Arg Gly Leu Ser Ile Glu Gln Leu Thr Thr Leu Ala Glu
515                 520                 525                 530 aag ctc cta ggg cct ggt gtg aac tac tca ggg tgt cag atc aca tgg      1810
Lys Leu Leu Gly Pro Gly Val Asn Tyr Ser Gly Cys Gln Ile Thr Trp
                535                 540                 545 gct aaa ttc tgc aaa gaa aac atg gct ggc aag ggc ttc tcc ttc tgg      1858
Ala Lys Phe Cys Lys Glu Asn Met Ala Gly Lys Gly Phe Ser Phe Trp
            550                 555                 560 gtc tgg cta gac aat atc atc gac ctt gtg aaa aag tat atc ttg gcc      1906
Val Trp Leu Asp Asn Ile Ile Asp Leu Val Lys Lys Tyr Ile Leu Ala
        565                 570                 575 ctt tgg aat gaa ggg tac atc atg ggt ttc atc agc aag gag cgg gag      1954
Leu Trp Asn Glu Gly Tyr Ile Met Gly Phe Ile Ser Lys Glu Arg Glu
    580                 585                 590 cgg gcc atc cta agc aca aag ccc ccg ggc acc ttc cta ctg cgc ttc      2002
Arg Ala Ile Leu Ser Thr Lys Pro Pro Gly Thr Phe Leu Leu Arg Phe
595                 600                 605                 610 agc gag agc agc aaa gaa gga ggg gtc act ttc act tgg gtg gaa aag      2050
Ser Glu Ser Ser Lys Glu Gly Gly Val Thr Phe Thr Trp Val Glu Lys
                615                 620                 625 gac atc agt ggc aag acc cag atc cag tct gta gag cca tac acc aag      2098
Asp Ile Ser Gly Lys Thr Gln Ile Gln Ser Val Glu Pro Tyr Thr Lys
            630                 635                 640 cag cag ctg aac aac atg tca ttt gct gaa atc atc atg ggc tat aag      2146
Gln Gln Leu Asn Asn Met Ser Phe Ala Glu Ile Ile Met Gly Tyr Lys
        645                 650                 655 atc atg gat gcg acc aac atc ctg gtg tct cca ctt gtc tac ctc tac      2194
Ile Met Asp Ala Thr Asn Ile Leu Val Ser Pro Leu Val Tyr Leu Tyr
    660                 665                 670 ccc gac att ccc aag gag gag gca ttt gga aag tac tgt agg ccc gag      2242
Pro Asp Ile Pro Lys Glu Glu Ala Phe Gly Lys Tyr Cys Arg Pro Glu
675                 680                 685                 690 agc cag gag cac ccc gaa gcc gac cca ggt agt gct gcc ccg tac ctg      2290
Ser Gln Glu His Pro Glu Ala Asp Pro Gly Ser Ala Ala Pro Tyr Leu
                695                 700                 705 aag acc aag ttc atc tgt gtg aca cca ttc att gat gca gtt tgg aaa      2338
Lys Thr Lys Phe Ile Cys Val Thr Pro Phe Ile Asp Ala Val Trp Lys
            710                 715                 720 taa cggtgaaggt gctgagccct cagcaggagg gcagtttgag tcgctcacgt           2391
ttgacatgga tctgacctcg gagtgtgcta cctcccccat gtgaggagct gaaaccagaa    2451
gctgcagaga cgtgacttga gacacctgcc ccgtgctcca cccctaagca gccgaacccc    2511
atatcgtctg aaactcctaa ctttgtggtt ccagattttt tttttaatt tcctacttct     2571 gctatctttg ggcaatctgg gcacttttta aaagagagaa atgagtgagt gtgggtgata    2631
aactgttatg taaagaggag agcaccctctg agtctgggga tggggctgag agcagaaggg   2691
```

-continued

```
aggcaaaggg gaacacctcc tgtcctgccc gcctgccctc cttttttcagc agctcggggg      2751 ttggttgtta gacaagtgcc tcctggtgcc catggctacc tgttgcccca ctctgtgagc      2811
tgatacccca ttctgggaac tcctggctct gcactttcaa ccttgctaat atccacatag      2871
aagctaggac taagcccagg aggttcctct ttaaattaaa aaaaaaaaaa aaa             2924
```

<210> SEQ ID NO 383
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 383
tggtattgct gcaggtcgtt                                                  20

<210> SEQ ID NO 384
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 384
cggcaggtca atggtattgc                                                  20

<210> SEQ ID NO 385
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 385
ggacatcggc aggtcaatgg                                                  20

<210> SEQ ID NO 386
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 386
ttgtacctca gcgcggacgc                                                  20

<210> SEQ ID NO 387
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 387
aaaagtgccc agattgccc                                                   19

<210> SEQ ID NO 388
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 388
aaaagtgccc agattgcc                                                    18

<210> SEQ ID NO 389
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 389
aaagtgccca gattgcc                                                    17

<210> SEQ ID NO 390
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 390
gctgcaggtc gttggtgtca                                                 20

<210> SEQ ID NO 391
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 391
ttctacctcg cgcgatttac                                                 20

<210> SEQ ID NO 392
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 392
gtacagttat gcgcggtaga                                                 20

<210> SEQ ID NO 393
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 393
ttagaatacg tcgcgttatg                                                 20

<210> SEQ ID NO 394
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 394
cgttattaac ctccgttgaa                                                 20

<210> SEQ ID NO 395
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 395
ctgctagcct ctggatttga                                              20

<210> SEQ ID NO 396
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 396
ctcttactgt gctgtggaca                                              20

<210> SEQ ID NO 397
<211> LENGTH: 15
<212> TYPE: DNA
<213> ORGANISM: Artificial Sequence
<220> FEATURE:
<223> OTHER INFORMATION: PCR Primer

<400> SEQUENCE: 397
gaggcccgcc caaca                                                   15

<210> SEQ ID NO 398
<211> LENGTH: 26
<212> TYPE: DNA
<213> ORGANISM: Artificial Sequence
<220> FEATURE:
<223> OTHER INFORMATION: PCR Primer

<400> SEQUENCE: 398
ttctgctaat gacgttatcc agtttt                                       26

<210> SEQ ID NO 399
<211> LENGTH: 14
<212> TYPE: DNA
<213> ORGANISM: Artificial Sequence
<220> FEATURE:
<223> OTHER INFORMATION: PCR Probe

<400> SEQUENCE: 399
ctgcctagat cggc                                                    14

<210> SEQ ID NO 400
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 400
attcttggga ttgttggtct t                                            21

<210> SEQ ID NO 401
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 401
ctccagcatc tgctgcttct t                                            21

<210> SEQ ID NO 402
<211> LENGTH: 20
<212> TYPE: DNA
```

```
-continued

<213> ORGANISM: Artificial Sequence
<220> FEATURE:
<223> OTHER INFORMATION: Antisense Oligonucleotide

<400> SEQUENCE: 402
tttgatcgag gttagccgtg                                              20

<210> SEQ ID NO 403
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-19
<223> OTHER INFORMATION: bases at these positions are RNA

<400> SEQUENCE: 403
cgagaggcgg acgggaccgt t                                            21

<210> SEQ ID NO 404
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 3, 4, 6, 8, 9, 10, 11, 12,
      14, 15, 16, 17, 19, 20, 21
<223> OTHER INFORMATION: bases at these positions are RNA

<400> SEQUENCE: 404
ttgctctccg cctgccctgg c                                            21

<210> SEQ ID NO 405
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 405
cgagaggcgg acgggaccg                                               19

<210> SEQ ID NO 406
<211> LENGTH: 19
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1, 2, 4, 6, 7, 8, 9, 10, 12, 13,
      14, 15, 17, 18, 19
<223> OTHER INFORMATION: bases at these positions are RNA

<400> SEQUENCE: 406
gctctccgcc tgccctggc                                               19
```

ANTISENSE OLIGONUCLEOTIDE MODULATION OF STAT3 EXPRESSION

RELATED APPLICATIONS

This application is a continuation of U.S. application Ser. No. 11/829,279 filed Jul. 27, 2007, now abandoned, which is a divisional of U.S. application Ser. No. 11/376,033, filed Mar. 15, 2006, now U.S. Pat. No. 7,307,069, which is a divisional U.S. application Ser. No. 10/773,678, filed Feb. 6, 2004, now U.S. Pat. No. 7,098,192, each of which is incorporated herein by reference.

FIELD OF THE INVENTION

This invention relates to compositions and methods for modulating expression of the human STAT3 gene, which encodes a naturally present DNA-binding protein involved in signal transduction and transcriptional activation, and is implicated in disease. This invention is also directed to methods for inhibiting STAT3-mediated signal transduction and transcriptional activation; these methods can be used diagnostically or therapeutically. Furthermore, this invention is directed to treatment of conditions associated with expression of the human STAT3 gene.

BACKGROUND OF THE INVENTION

The STAT (signal transducers and activators of transcription) family of proteins are DNA-binding proteins that play a dual role in signal transduction and activation of transcription. Presently, there are six distinct members of the STAT family (STAT1, STAT2, STAT3, STAT4, STAT5, and STAT6) and several isoforms (STAT1α, STAT1β, STAT3α, and STAT3β). The activities of the STATs are modulated by various cytokines and mitogenic stimuli. Binding of a cytokine to its receptor results in the activation of Janus protein tyrosine kinases (JAKs) associated with these receptors. This in turn, phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

The specificity of STAT activation is due to specific cytokines, i.e. each STAT is responsive to a small number of specific cytokines. Other non-cytokine signaling molecules, such as growth factors, have also been found to activate STATs. Binding of these factors to a cell surface receptor associated with protein tyrosine kinase also results in phosphorylation of STAT.

STAT3 (also acute phase response factor (APRF)), in particular, has been found to be responsive to interleukin-6 (IL-6) as well as epidermal growth factor (EGF) (Darnell, Jr., J. E., et al., *Science*, 1994, 264, 1415-1421). In addition, STAT3 has been found to have an important role in signal transduction by interferons (Yang, C.-H., et al., *Proc. Natl. Acad. Sci. USA*, 1998, 95, 5568-5572). Evidence exists suggesting that STAT3 may be regulated by the MAPK pathway. ERK2 induces serine phosphorylation and also associates with STAT3 (Jain, N., et al., *Oncogene*, 1998, 17, 3157-3167).

STAT3 is expressed in most cell types (Zhong, Z., et al., *Proc. Natl. Acad. Sci. USA*, 1994, 91, 4806-4810). It induces the expression of genes involved in response to tissue injury and inflammation. STAT3 has also been shown to prevent apoptosis through the expression of bcl-2 (Fukada, T., et al., *Immunity*, 1996, 5, 449-460).

Aberrant expression of or constitutive expression of STAT3 is associated with a number of disease processes. STAT3 has been shown to be involved in cell transformation. It is constitutively activated in v-src-transformed cells (Yu, C.-L., et al., *Science*, 1995, 269, 81-83). Constitutively active STAT3 also induces STAT3 mediated gene expression and is required for cell transformation by src (Turkson, J., et al., *Mol. Cell. Biol.*, 1998, 18, 2545-2552). STAT3 is also constitutively active in Human T cell lymphotropic virus I (HTLV-I) transformed cells (Migone, T.-S. et al., *Science*, 1995, 269, 79-83).

Constitutive activation and/or overexpression of STAT3 appears to be involved in several forms of cancer, including myeloma, breast carcinomas, prostate cancer, brain tumors, head and neck carcinomas, melanoma, leukemias and lymphomas, particularly chronic myelogenous leukemia and multiple myeloma. Niu et al., *Cancer Res.*, 1999, 59, 5059-5063. Breast cancer cell lines that overexpress EGFR constitutively express phosphorylated STAT3 (Sartor, C. I., et al., *Cancer Res.*, 1997, 57, 978-987; Garcia, R., et al., *Cell Growth and Differentiation*, 1997, 8, 1267-1276). Activated STAT3 levels were also found to be elevated in low grade glioblastomas and medulloblastomas (Cattaneo, E., et al., *Anticancer Res.*, 1998, 18, 2381-2387).

Cells derived from both rat and human prostate cancers have been shown to have constitutively activated STAT3, with STAT3 activation being correlated with malignant potential. Expression of a dominant-negative STAT3 was found to significantly inhibit the growth of human prostate cells. Ni et al., *Cancer Res.*, 2000, 60, 1225-1228.

STAT3 has also been found to be constitutively activated in some acute leukemias (Gouilleux-Gruart, V., et al., *Leuk. Lymphoma*, 1997, 28, 83-88) and T cell lymphoma (Yu, C.-L., et al., *J. Immunol.*, 1997, 159, 5206-5210). Interestingly, STAT3 has been found to be constitutively phosphorylated on a serine residue in chronic lymphocytic leukemia (Frank, D. A., et al., *J. Clin. Invest.*, 1997, 100, 3140-3148). In addition, antisense oligonucleotides to STAT3 have been shown to promote apoptosis in non small cell lung cancer cells (Song et al., *Oncogene* 22:4150, 2003) and prostate cancer cells (Mora et al., *Cancer Res.* 62:6659, 2002).

STAT3 has been found to be constitutively active in myeloma tumor cells, both in culture and in bone marrow mononuclear cells from patients with multiple myeloma. These cells are resistant to Fas-mediated apoptosis and express high levels of Bcl-xL. STAT3 signaling was shown to be essential for survival of myeloma tumor cells by conferring resistance to apoptosis. Thus STAT3 is a potential target for therapeutic intervention in multiple myeloma and other cancers with activated STAT3 signaling. There is a distinct medical need for novel therapies for chemoresistant myeloma. Velcade was approved in May 2003 with an 188 evaluable patient pivotal trial based on tumor shrinkage, not survival. 28% showed a partial tresponse. The data is currently under FDA review.

Catlett-Falcone, R., et al., *Immunity*, 1999, 10, 105-115. A gene therapy approach in a syngeneic mouse tumor model system has been used to inhibit activated STAT3 in vivo using a dominant-negative STAT3 variant. This inhibition of activated STAT3 signaling was found to suppress B16 melanoma tumor growth and induce apoptosis of B16 tumor cells in vivo. Interestingly, the number of apoptotic cells (95%) exceeded the number of transfected cells, indicating a possible antitumor "bystander effect" in which an inflammatory response (tumor infiltration by acute and chronic inflammatory cells) may participate in killing of residual tumor cells. Niu et al., *Cancer Res.*, 1999, 59, 5059-5063. Constitutively activated STAT3 is also associated with chronic myelogenous leukemia.

STAT3 may also play a role in inflammatory diseases including rheumatoid arthritis. Activated STAT3 has been found in the synovial fluid of rheumatoid arthritis patients (Sengupta, T. K., et al., *J. Exp. Med.*, 1995, 181, 1015-1025) and cells from inflamed joints (Wang, F., et al., *J. Exp. Med.*, 1995, 182, 1825-1831).

Multiple forms of STAT3 exist, generated by alternative splicing. STAT3β is a short form of STAT3 (also, STAT3α) that differs predominately by the absence of 55 amino acid residues at the C-terminus. This domain contains the transactivation domain, and thus, STAT3β may act as a negative regulator of STAT3 function (Caldenhoven, E., et al., *J. Biol. Chem.*, 1996, 271, 13221-13227). STAT3β has been found to be more stable and have greater DNA-binding activity than STAT3α, while STAT3α is more transcriptionally active.

There are currently several approaches for inhibiting STAT3 expression. U.S. Pat. Nos. 5,719,042 and 5,844,082 to Akira, S, and Kishimoto, T. disclose the use of inhibitors of APRF, including antibodies, antisense nucleic acids and ribozymes for the treatment of IL-6 associated diseases, such as inflammatory diseases, leukemia, and cancer. Schreiber, R. D., et al., in U.S. Pat. Nos. 5,731,155; 5,582,999; and 5,463,023, disclose methods of inhibiting transcriptional activation using short peptides that bind p91. Darnell, J. E., et al., in U.S. Pat. No. 5,716,622, disclose peptides containing the DNA binding domain of STATs, chimeric proteins containing the DNA binding domain, and antibodies to STATs for inhibiting STAT transcriptional activation.

The use of an antisense oligonucleotide targeted to the translation start region of human STAT3 has been disclosed (Grandis, J. R., et al., *J. Clin. Invest.*, 1998, 102, 1385-1392). In this report, a phosphorothioate oligodeoxynucleotide complementary to the translation start region of STAT3 inhibited TGF-β stimulated cell growth mediated by the epidermal growth factor receptor (EGFR).

There remains an unmet need for therapeutic compositions and methods targeting expression of STAT3, and disease processes associated therewith.

SUMMARY OF THE INVENTION

The present invention provides oligonucleotides which are targeted to nucleic acids encoding STAT3 and are capable of modulating STAT3 expression. The present invention also provides chimeric oligonucleotides targeted to nucleic acids encoding human STAT3. The oligonucleotides of the invention are believed to be useful both diagnostically and therapeutically, and are believed to be particularly useful in the methods of the present invention.

The present invention also comprises methods of modulating the expression of human STAT3, in cells and tissues, using the oligonucleotides of the invention. Methods of inhibiting STAT3 expression are provided; these methods are believed to be useful both therapeutically and diagnostically. These methods are also useful as tools, for example, for detecting and determining the role of STAT3 in various cell functions and physiological processes and conditions and for diagnosing conditions associated with expression of STAT3.

The present invention also comprises methods for diagnosing and treating inflammatory diseases, particularly rheumatoid arthritis, and cancers, including those of the breast, prostate, head and neck, and brain, myelomas and melanomas and leukemias and lymphomas. These methods are believed to be useful, for example, in diagnosing STAT3-associated disease progression. These methods employ the oligonucleotides of the invention. These methods are believed to be useful both therapeutically, including prophylactically, and as clinical research and diagnostic tools.

DETAILED DESCRIPTION OF THE INVENTION

STAT3 plays an important role in cytokine signal transduction. Overexpression and/or constitutive activation of STAT3 is associated with a number of inflammatory diseases and cancers. As such, this DNA-binding protein represents an attractive target for treatment of such diseases. In particular, modulation of the expression of STAT3 may be useful for the treatment of diseases such as rheumatoid arthritis, breast cancer, prostate cancer, brain cancer, head and neck cancer, myelomas, melanomas, leukemias and lymphomas.

The present invention employs antisense compounds, particularly oligonucleotides, for use in modulating the function of nucleic acid molecules encoding STAT3, ultimately modulating the amount of STAT3 produced. This is accomplished by providing oligonucleotides which specifically hybridize with nucleic acids, preferably mRNA, encoding STAT3.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding STAT3; in other words, a gene encoding STAT3, or mRNA expressed from the STAT3 gene. mRNA which encodes STAT3 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding STAT3, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of STAT3. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

In addition to the well known antisense effects of oligonucleotides, it has also been found that oligonucleotide analogs having at least one phosphorothioate bond can induce stimulation of a local immune response. This is described in U.S. Pat. No. 5,663,153 which is commonly assigned to the assignee of the present invention and is herein incorporated by reference in its entirety. This immunostimulatory effect does not appear to be related to any antisense effect which these oligonucleotide analogs may or may not possess. These oligonucleotide analogs are useful as immunopotentiators, either alone or in combination with other therapeutic modalities, such as drugs, particularly antiinfective and anticancer drugs, and surgical procedures to increase efficacy. In addition, the antiinfective and anticancer effects already possessed by certain antisense oligonucleotide analogs are enhanced through such immune stimulation.

It has also been found that oligonucleotide analogs having at least one phosphorothioate bond can be used to induce stimulation of a systemic or humoral immune response. Thus, these oligonucleotides are also useful as immunopotentiators of an antibody response, either alone or in combination with other therapeutic modalities. U.S. Pat. No. 5,663,153.

It is presently believed, therefore, that, in addition to the antisense effects of oligonucleotides targeted to STAT3, oligonucleotides containing at least one phosphorothioate backbone linkage may be useful in eliciting an immune response which may add to the antitumor "bystander effect" already observed with dominant negative inhibitors of STAT3 signaling. Niu et al., *Cancer Res.,* 1999, 59, 5059-5063. This effect is believed to be related to tumor infiltration by acute and chronic inflammatory cells which may participate in killing of residual tumor cells. Thus the therapeutic effects of antisense oligonucleotides targeted to STAT3 may be potentiated by the immunostimulatory properties of the oligonucleotides themselves. Alternatively, oligonucleotides which may not be targeted to STAT3 but which contain at least one phosphorothioate backbone linkage may be used as adjuvants in combination with antisense or other inhibitors of STAT3.

The oligonucleotides of this invention can be used in diagnostics, therapeutics, prophylaxis, and as research reagents and in kits. Since the oligonucleotides of this invention hybridize to nucleic acids encoding STAT3, sandwich, colorimetric and other assays can easily be constructed to exploit this fact. Provision of means for detecting hybridization of oligonucleotide with the STAT3 gene or mRNA can routinely be accomplished. Such provision may include enzyme conjugation, radiolabelling or any other suitable detection systems. Kits for detecting the presence or absence of STAT3 may also be prepared.

The present invention is also suitable for diagnosing abnormal inflammatory states or certain cancers in tissue or other samples from patients suspected of having an inflammatory disease such as rheumatoid arthritis or cancers such as breast, brain, or head and neck cancer, melanomas, myelomas, leukemias and lymphomas. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3= or 5=hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3= to 5=phosphodiester linkage.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620). Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, it has been shown that it is, in fact, the single-stranded RNA oligomers of antisense polarity of the dsRNAs which are the potent inducers of RNAi (Tijsterman et al., *Science,* 2002, 295, 694-697). The use of these double stranded RNA molecules (short interfering RNA or siRNA) for targeting and inhibiting the expression of STAT3 mRNA is also contemplated. These double stranded RNA molecules target regions similar to those targeted by antisense oligocleotides and have similar effects. These double stranded RNA molecules are generally 19-21 base pairs in length, but may range between 8 and 50 nucleobases. The production of siRNA molecules is described in a general sense in the examples provided below, but it will be appreciated that any desired siRNA targeted to STAT3 may be synthesized by conventional oligonucleotide synthesis techniques. Once the sequence of the antisense strand is known, the complementary sense strand is synthesized based on base pairing. The sense and antisense strands are then combined to form the siRNA.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

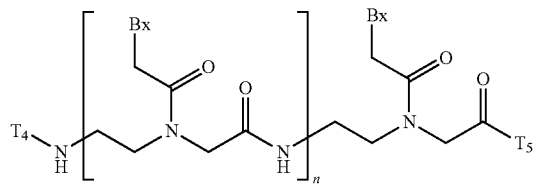

wherein

Bx is a heterocyclic base moiety;

$T_4$ is hydrogen, an amino protecting group, —C(O)R$_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)Z$_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

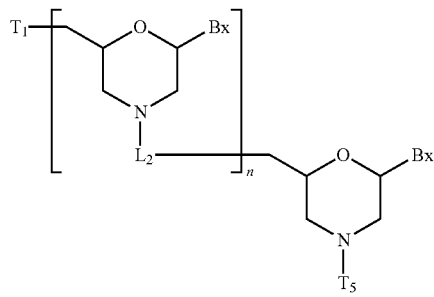

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. Coli RNase resulting in cleavage of the target RNA strand.

The general formula of CeNA is shown below:

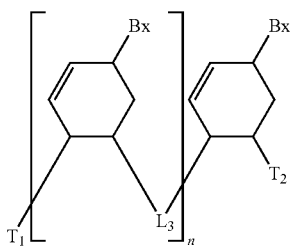

wherein each Bx is a heterocyclic base moiety;

$T_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, Bioorg. Med. Chem. Lett., 1999, 9, 1563-1566) and would have the general formula:

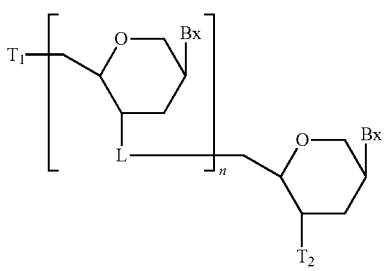

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($-CH_2-$)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

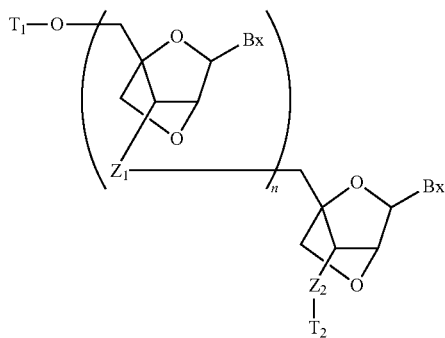

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

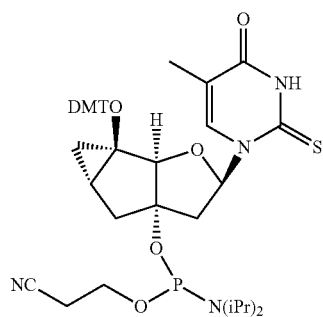

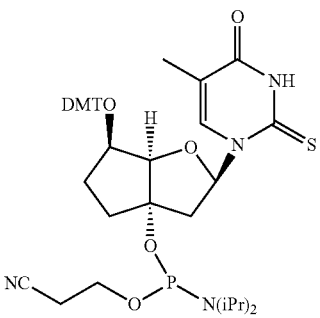

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

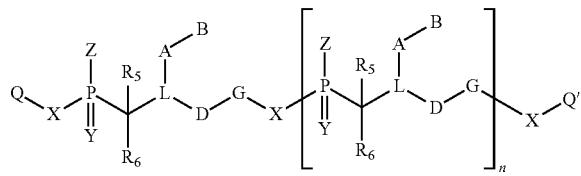

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—N($CH_3$)$_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

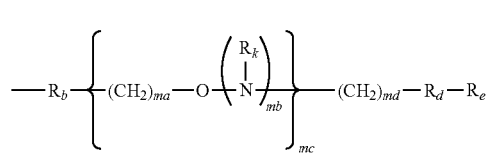

Ia

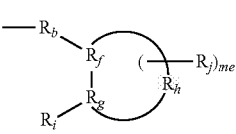

IIa wherein:

$R_b$ is O, S or NH;

$R_d$ is a single bond, O, S or C(=O);

$R_e$ is $C_1$-$C_{10}$ alkyl, N($R_k$)($R_m$), N($R_k$)($R_n$), N=C($R_p$)($R_q$), N=C($R_p$)($R_r$) or has formula $III_a$;

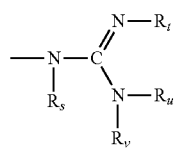

IIIa $R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$—$R_y$;
$R_p$ is hydrogen, a nitrogen protecting group or —$R_x$—$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;
each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)nCH_3)]_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxy-ethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

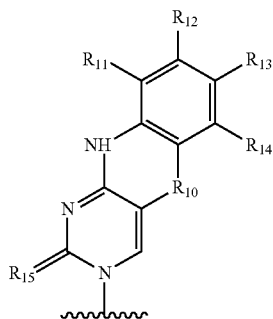

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., Nucleosides and Nucleotides, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5_{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocycicic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., dihexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013, 830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Scheme 1

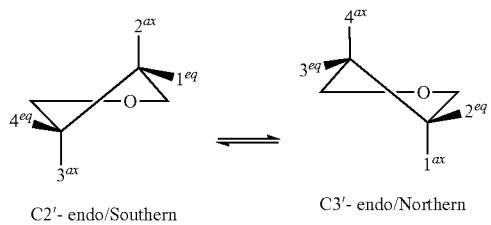

C2'- endo/Southern    C3'- endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

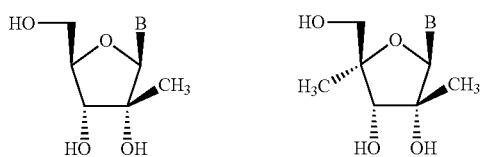

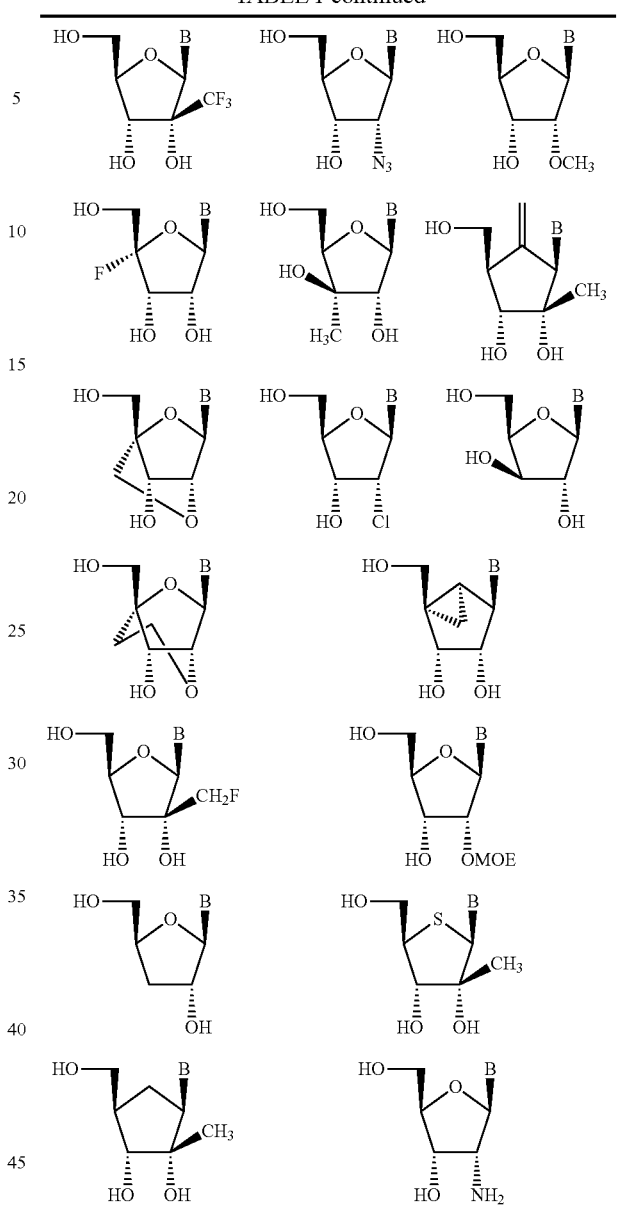

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH2CH2OCH3) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

The oligonucleotides in accordance with this invention (single stranded or double stranded) preferably comprise from about 8 to about 80 nucleotides, more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of STAT3 mRNA.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. A Pharmaceutically acceptable salts@ are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a Aprodrug@ form. The term Aprodrug@ indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91-192; Muranishi, *Critical Reviews in Therapeutic Drug Carrier Systems* 1990, 7, 1-33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651-654).

The physiological roles of bile include the facilitation of dispersion and absorption of lipids and fat-soluble vitamins (Brunton, Chapter 38 *In: Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1-33; Buur et al., *J. Control Rel.* 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Pharmacol.* 1988, 40, 252-257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621-626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698-708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin, gemcitabine and diethylstilbestrol (DES). See, generally, *The Merck Manual of Diagnosis and Therapy*, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.).

For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (J. Med. Chem. 1993, 36, 831-841). Briefly, the protected nucleoside N6-benzoyl-2'-deoxy-2'-fluoroadenosine is synthesized utilizing commercially available 9-β-D-arabinofuranosyladenine as starting material and by modifying literature procedures whereby the 2'-a-fluoro atom is introduced by a SN2-displacement of a 2'-β-O-trifyl group. Thus N6-benzoyl-9-β-D-arabinofuranosyladenine is selectively protected in moderate yield as the 3',5'-ditetrahydropyranyl (THP) intermediate. Deprotection of the THP and N6-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group is followed by protection of the hydroxyl group with THP to give diisobutyryl di-THP protected arabinofuranosylguanine Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3' phosphoramidites.

2'-deoxy-2'-fluorocytidine is synthesized via amination of 2'-deoxy-2'-fluorouridine, followed by selective protection to give N$^4$-benzoyl-2'-deoxy-2'-fluorocytidine. Standard procedures are used to obtain the 5'-DMT and 5'-DMT-3' phosphoramidites.

2'-(2-methoxyethyl)-modified amidites were synthesized according to Martin, P. (Helv. Chim. Acta 1995, 78, 486-506). For ease of synthesis, the last nucleotide may be a deoxynucleotide. 2'-O—CH$_2$CH$_2$OCH$_3$-cytosines may be 5-methyl cytosines.

Synthesis of 5-Methyl Cytosine Monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-β-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0-10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197-3203) using commercially available phosphoramidites (Glen Research, Sterling Va. or ChemGenes, Needham Mass.).

2-O-(dimethylaminooxyethyl) nucleoside amidites

2'-(Dimethylaminooxyethoxy) nucleoside amidites [also known in the art as 2'-β-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate)

indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy) ethyl]-5-methyluridine as white foam (1.95, 78%).

5'-O-tert-Butyldiphenylsilyl-2'-O—[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous NaHCO₃ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO₃ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-β-tert-butyldiphenylsilyl-2'-O—[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N¹,N¹-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO₃ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366-374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497-1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Alternatively, oligonucleotides were synthesized in 96 well plate format via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites were purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 2

Human STAT3 Oligodeoxynucleotide Sequences

Antisense oligonucleotides were designed to target human STAT3. Target sequence data are from the APRF cDNA sequence published by Akira, S. et al. (*Cell*, 1994, 77, 63-71); Genbank accession number L29277, provided herein as SEQ ID NO: 1. A set of oligodeoxynucleotides were synthesized with phosphorothioate linkages. 2'-deoxy cytosines were 5-methyl cytosines. These oligonucleotide sequences are shown in Table 1. An additional set of oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 2.

An appropriate cell line, typically expressing high levels of STAT3, is chosen for in vitro studies. Cell culture conditions are those standard for that particular cell line. Oligonucleotide treatment is for four hours and mRNA usually isolated 24 to 48 hours following initial treatment. mRNA is isolated using the RNAEASY7 kit (Qiagen, Santa Clarita, Calif.).

TABLE 1

Nucleotide Sequences of Human STAT3 Phosphorothioate Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106691 | GTCTGCGCCGCCGCCCCGAA | 2 | 0010-0029 | 5'-UTR |
| 106692 | GGCCGAAGGGCCTCTCCGAG | 3 | 0130-0149 | 5'-UTR |
| 106693 | TCCTGTTTCTCCGGCAGAGG | 4 | 0202-0221 | AUG |
| 106694 | CATCCTGTTTCTCCGGCAGA | 5 | 0204-0223 | AUG |
| 106695 | GCCATCCTGTTTCTCCGGCA | 6 | 0206-0225 | AUG |
| 106696 | GGGCCATCCTGTTTCTCCGG | 7 | 0208-0227 | AUG |
| 106697 | TTGGGCCATCCTGTTTCTCC | 8 | 0210-0229 | AUG |
| 106698 | CATTGGGCCATCCTGTTTCT | 9 | 0212-0231 | AUG |
| 106699 | TCCATTGGGCCATCCTGTTT | 10 | 0214-0233 | AUG |
| 106700 | ATTCCATTGGGCCATCCTGT | 11 | 0216-0235 | AUG |
| 106701 | TGATTCCATTGGGCCATCCT | 12 | 0218-0237 | AUG |
| 106702 | GCTGATTCCATTGGGCCATC | 13 | 0220-0239 | AUG |
| 106703 | TAGCTGATTCCATTGGGCCA | 14 | 0222-0241 | AUG |
| 106704 | TGTAGCTGATTCCATTGGGC | 15 | 0224-0243 | coding |
| 106705 | CTGTAGAGCTGATGGAGCTG | 16 | 0269-0288 | coding |
| 106706 | CCCAATCTTGACTCTCAATC | 17 | 0331-0350 | coding |
| 106707 | CCCAGGAGATTATGAAACAC | 18 | 0386-0405 | coding |
| 106708 | ACATTCGACTCTTGCAGGAA | 19 | 0431-0450 | coding |
| 106709 | TCTGAAGAAACTGCTTGATT | 20 | 0475-0494 | coding |
| 106710 | GGCCACAATCCGGGCAATCT | 21 | 0519-0538 | coding |
| 106711 | TGGCTGCAGTCTGTAGAAGG | 22 | 0562-0581 | coding |
| 106712 | CTGCTCCAGCATCTGCTGCT | 23 | 0639-0658 | coding |

TABLE 1-continued

Nucleotide Sequences of Human STAT3 Phosphorothioate Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106713 | TTTCTGTTCTAGATCCTGCA | 24 | 0684-0703 | coding |
| 106714 | TAGTTGAAATCAAAGTCATC | 25 | 0728-0747 | coding |
| 106715 | TTCCATTCAGATCTTGCATG | 26 | 0772-0791 | coding |
| 106716 | TCTGTTCCAGCTGCTGCATC | 27 | 0817-0836 | coding |
| 106717 | TCACTCACGATGCTTCTCCG | 28 | 0860-0879 | coding |
| 106718 | GAGTTTTCTGCACGTACTCC | 29 | 0904-0923 | coding |
| 106719 | ATCTGTTGCCGCCTCTTCCA | 30 | 0947-0968 | coding |
| 106720 | CTAGCCGATCTAGGCAGATG | 31 | 0991-1010 | coding |
| 106721 | CGGGTCTGAAGTTGAGATTC | 32 | 1034-1053 | coding |
| 106722 | CGGCCGGTGCTGTACAATGG | 33 | 1110-1129 | coding |
| 106723 | TTTCATTAAGTTTCTGAACA | 34 | 1155-1174 | coding |
| 106724 | AGGATGCATGGGCATGCAGG | 35 | 1200-1219 | coding |
| 106725 | GACCAGCAACCTGACTTTAG | 36 | 1260-1279 | coding |
| 106726 | ATGCACACTTTAATTTTAAG | 37 | 1304-1323 | coding |
| 106727 | TTCCGGGATCCTCTGAGAGC | 38 | 1349-1368 | coding |
| 106728 | TTCCATGTTCATCACTTTTG | 39 | 1392-1411 | coding |
| 106729 | GTCAAGTGTTTGAATTCTGC | 40 | 1436-1455 | coding |
| 106730 | CAATCAGGGAAGCATCACAA | 41 | 1495-1514 | coding |
| 106731 | TACACCTCGGTCTCAAAGGT | 42 | 1538-1557 | coding |
| 106732 | TGACAAGGAGTGGGTCTCTA | 43 | 1581-1600 | coding |
| 106733 | CGCCCAGGCATTTGGCATCT | 44 | 1626-1645 | coding |
| 106734 | CATTCTTGGGATTGTTGGTC | 45 | 1669-1688 | coding |
| 106735 | CACTTGGTCCCAGGTTCCAA | 46 | 1713-1732 | coding |
| 106736 | CCCGCTTGGTGGTGGACGAG | 47 | 1756-1775 | coding |
| 106737 | AGTTCACACCAGGCCCTAGG | 48 | 1816-1835 | coding |
| 106738 | GTTTTCTTTGCAGAAGTTAG | 49 | 1860-1879 | coding |
| 106739 | ATATTGTCTAGCCAGACCCA | 50 | 1904-1923 | coding |
| 106740 | AACCCATGATGTACCCTTCA | 51 | 1963-1982 | coding |
| 106741 | GCTTAGTGCTCAAGATGGCC | 52 | 2005-2024 | coding |
| 106742 | GCTGCTTTCACTGAAGCGCA | 53 | 2043-2062 | coding |
| 106743 | GTGAAAGTGACGCCTCCTTC | 54 | 2066-2085 | coding |
| 106744 | CTGATGTCCTTCTCCACCCA | 55 | 2087-2106 | coding |
| 106745 | ACTGGATCTGGGTCTTACCG | 56 | 2107-2126 | coding |
| 106746 | AAATGACATGTTGTTCAGCT | 57 | 2151-2170 | coding |
| 106747 | GCCCATGATGATTTCAGCAA | 58 | 2169-2188 | coding |
| 106748 | TATTGGTAGCATCCATGATC | 59 | 2194-2213 | coding |
| 106749 | ATAGACAAGTGGAGACAACA | 60 | 2217-2236 | coding |
| 106750 | TTGGGAATGTCAGGATAGAG | 61 | 2237-2256 | coding |
| 106751 | CTCCTGGCTCTCTGGCCGAC | 62 | 2280-2299 | coding |
| 106752 | ACCTGGGTCAGCTTCAGGAT | 63 | 2301-2320 | coding |
| 106753 | CACAGATAAACTTGGTCTTC | 64 | 2338-2357 | coding |
| 106754 | ATCGGCAGGTCAATGGTATT | 65 | 2378-2397 | coding |
| 106755 | CCAAACTGCATCAATGAATC | 66 | 2414-2433 | coding |
| 106756 | GGTTCAGCACCTTCACCATT | 67 | 2438-2457 | coding |
| 106757 | GAGGGACTCAAACTGCCCTC | 68 | 2466-2485 | coding |
| 106758 | CAACTCCATGTCAAAGGTGA | 69 | 2484-2503 | coding |
| 106759 | TTCTCAGCTCCTCACATGGG | 70 | 2525-2544 | STOP |
| 106760 | CGTTCTCAGCTCCTCACATG | 71 | 2527-2546 | STOP |
| 106761 | TCCGTTCTCAGCTCCTCACA | 72 | 2529-2548 | STOP |
| 106762 | CTTCCGTTCTCAGCTCCTCA | 73 | 2531-2550 | STOP |
| 106763 | AGCTTCCGTTCTCAGCTCCT | 74 | 2533-2552 | STOP |
| 106764 | AGAATGCAGGTAGGCGCCTC | 75 | 2569-2588 | 3'-UTR |
| 106765 | ACCACAAAGTTAGTAGTTTC | 76 | 2623-2642 | 3'-UTR |
| 106766 | TGCTCAAAGATAGCAGAAGT | 77 | 2665-2684 | 3'-UTR |
| 106767 | ATTCACTCATTTCTCTATTT | 78 | 2701-2720 | 3'-UTR |
| 106768 | CATTTAGATAAAAGCAGATC | 79 | 2727-2746 | 3'-UTR |
| 106769 | ACATCCTTATTTGCATTTAG | 80 | 2740-2759 | 3'-UTR |
| 106770 | GATCATGGGTCTCAGAGAAC | 81 | 2760-2779 | 3'-UTR |

[1] "C" residues are 5-methyl-cytosines; all linkages are phosphorothioate linkages.
[2] Coordinates from Genbank Accession No. L29277, locus name "HUMAPRF", SEQ ID NO. 1.

TABLE 2

Nucleotide Sequences of Human STAT3 Chimeric (deoxy gapped) Phosphorothioate Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106771 | GTCTGCGCCGCCGCCCCGAA | 2 | 0010-0029 | 5'-UTR |
| 106772 | GGCCGAAGGGCCTCTCCGAG | 3 | 0130-0149 | 5'-UTR |
| 106773 | TCCTGTTTCTCCGGCAGAGG | 4 | 0202-0221 | AUG |
| 106774 | CATCCTGTTTCTCCGGCAGA | 5 | 0204-0223 | AUG |
| 106775 | GCCATCCTGTTTCTCCGGCA | 6 | 0206-0225 | AUG |
| 106776 | GGGCCATCCTGTTTCTCCGG | 7 | 0208-0227 | AUG |

TABLE 2-continued

Nucleotide Sequences of Human STAT3 Chimeric (deoxy gapped) Phosphorothioate Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106777 | TTGGGCCATCCTGTTTCTCC | 8 | 0210-0229 | AUG |
| 106778 | CATTGGGCCATCCTGTTTCT | 9 | 0212-0231 | AUG |
| 106779 | TCCATTGGGCCATCCTGTTT | 10 | 0214-0233 | AUG |
| 106780 | ATTCCATTGGGCCATCCTGT | 11 | 0216-0235 | AUG |
| 106781 | TGATTCCATTGGGCCATCCT | 12 | 0218-0237 | AUG |
| 106782 | GCTGATTCCATTGGGCCATC | 13 | 0220-0239 | AUG |
| 106783 | TAGCTGATTCCATTGGGCCA | 14 | 0222-0241 | AUG |
| 106784 | TGTAGCTGATTCCATTGGGC | 15 | 0224-0243 | coding |
| 106785 | CTGTAGAGCTGATGGAGCTG | 16 | 0269-0288 | coding |
| 106786 | CCCAATCTTGACTCTCAATC | 17 | 0331-0350 | coding |
| 106787 | CCCAGGAGATTATGAAACAC | 18 | 0386-0405 | coding |
| 106788 | ACATTCGACTCTTGCAGGAA | 19 | 0431-0450 | coding |
| 106789 | TCTGAAGAAACTGCTTGATT | 20 | 0475-0494 | coding |
| 106790 | GGCCACAATCCGGGCAATCT | 21 | 0519-0538 | coding |
| 106791 | TGGCTGCAGTCTGTAGAAGG | 22 | 0562-0581 | coding |
| 106792 | CTGCTCCAGCATCTGCTGCT | 23 | 0639-0658 | coding |
| 106793 | TTTCTGTTCTAGATCCTGCA | 24 | 0684-0703 | coding |
| 106794 | TAGTTGAAATCAAAGTCATC | 25 | 0728-0747 | coding |
| 106795 | TTCCATTCAGATCTTGCATG | 26 | 0772-0791 | coding |
| 106796 | TCTGTTCCAGCTGCTGCATC | 27 | 0817-0836 | coding |
| 106797 | TCACTCACGATGCTTCTCCG | 28 | 0860-0879 | coding |
| 106798 | GAGTTTTCTGCACGTACTCC | 29 | 0904-0923 | coding |
| 106799 | ATCTGTTGCCGCCTCTTCCA | 30 | 0947-0968 | coding |
| 106800 | CTAGCCGATCTAGGCAGATG | 31 | 0991-1010 | coding |
| 106801 | CGGGTCTGAAGTTGAGATTC | 32 | 1034-1053 | coding |
| 106802 | CGGCCGGTGCTGTACAATGG | 33 | 1110-1129 | coding |
| 106803 | TTTCATTAAGTTTCTGAACA | 34 | 1155-1174 | coding |
| 106804 | AGGATGCATGGGCATGCAGG | 35 | 1200-1219 | coding |
| 106805 | GACCAGCAACCTGACTTTAG | 36 | 1260-1279 | coding |
| 106806 | ATGCACACTTTAATTTTAAG | 37 | 1304-1323 | coding |
| 106807 | TTCCGGGATCCTCTGAGAGC | 38 | 1349-1368 | coding |
| 106808 | TTCCATGTTCATCACTTTTG | 39 | 1392-1411 | coding |
| 106809 | GTCAGTGTTTGAATTCTGC | 40 | 1436-1455 | coding |
| 106810 | CAATCAGGGAAGCATCACAA | 41 | 1495-1514 | coding |
| 106811 | TACACCTCGGTCTCAAAGGT | 42 | 1538-1557 | coding |
| 106812 | TGACAAGGAGTGGGTCTCTA | 43 | 1581-1600 | coding |
| 106813 | CGCCCAGGCATTTGGCATCT | 44 | 1626-1645 | coding |
| 106814 | CATTCTTGGGATTGTTGGTC | 45 | 1669-1688 | coding |
| 106815 | CACTTGGTCCCAGGTTCCAA | 46 | 1713-1732 | coding |
| 106816 | CCCGCTTGGTGGTGGACGAG | 47 | 1756-1775 | coding |
| 106817 | AGTTCACACCAGGCCCTAGG | 48 | 1816-1835 | coding |
| 106818 | GTTTTCTTTGCAGAAGTTAG | 49 | 1860-1879 | coding |
| 106819 | ATATTGTCTAGCCAGACCCA | 50 | 1904-1923 | coding |
| 106820 | AACCCATGATGTACCCTTCA | 51 | 1963-1982 | coding |
| 106821 | GCTTAGTGCTCAAGATGGCC | 52 | 2005-2024 | coding |
| 106822 | GCTGCTTTCACTGAAGCGCA | 53 | 2043-2062 | coding |
| 106823 | GTGAAAGTGACGCCTCCTTC | 54 | 2066-2085 | coding |
| 106824 | CTGATGTCCTTCTCCACCCA | 55 | 2087-2106 | coding |
| 106825 | ACTGGATCTGGGTCTTACCG | 56 | 2107-2126 | coding |
| 106826 | AAATGACATGTTGTTCAGCT | 57 | 2151-2170 | coding |
| 106827 | GCCCATGATGATTTCAGCAA | 58 | 2169-2188 | coding |
| 106828 | TATTGGTAGCATCCATGATC | 59 | 2194-2213 | coding |
| 106829 | ATAGACAAGTGGAGACAACA | 60 | 2217-2236 | coding |
| 106830 | TTGGGAATGTCAGGATAGAG | 61 | 2237-2256 | coding |
| 106831 | CTCCTGGCTCTCTGGCCGAC | 62 | 2280-2299 | coding |
| 106832 | ACCTGGGTCAGCTTCAGGAT | 63 | 2301-2320 | coding |
| 106833 | CACAGATAAACTTGGTCTTC | 64 | 2338-2357 | coding |
| 106834 | ATCGGCAGGTCAATGGTATT | 65 | 2378-2397 | coding |
| 106835 | CCAAACTGCATCAATGAATC | 66 | 2414-2433 | coding |
| 106836 | GGTTCAGCACCTTCACCATT | 67 | 2438-2457 | coding |
| 106837 | GAGGGACTCAAACTGCCCTC | 68 | 2466-2485 | coding |
| 106838 | CAACTCCATGTCAAAGGTGA | 69 | 2484-2503 | coding |
| 106839 | TTCTCAGCTCCTCACATGGG | 70 | 2525-2544 | STOP |
| 106840 | CGTTCTCAGCTCCTCACATG | 71 | 2527-2546 | STOP |
| 106841 | TCCGTTCTCAGCTCCTCACA | 72 | 2529-2548 | STOP |
| 106842 | CTTCCGTTCTCAGCTCCTCA | 73 | 2531-2550 | STOP |
| 106843 | AGCTTCCGTTCTCAGCTCCT | 74 | 2533-2552 | STOP |
| 106844 | AGAATGCAGGTAGGCGCCTC | 75 | 2569-2588 | 3'-UTR |
| 106845 | ACCACAAAGTTAGTAGTTTC | 76 | 2623-2642 | 3'-UTR |
| 106846 | TGCTCAAAGATAGCAGAAGT | 77 | 2665-2684 | 3'-UTR |
| 106847 | ATTCACTCATTTCTCTATTT | 78 | 2701-2720 | 3'-UTR |

TABLE 2-continued

Nucleotide Sequences of Human STAT3 Chimeric (deoxy gapped) Phosphorothioate Oligonucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106848 | CATTTAGATAAAAGCAGATC | 79 | 2727-2746 | 3'-UTR |
| 106849 | ACATCCTTATTTGCATTTAG | 80 | 2740-2759 | 3'-UTR |
| 106850 | GATCATGGGTCTCAGAGAAC | 81 | 2760-2779 | 3'-UTR |

[1]Emboldened residues are 2'-methoxyethoxy residues, 2'-methoxyethoxy cytosine residues and 2'-OH cytosine residues are 5-methyl-cytosines; all linkages are phosphorothioate linkages.
[2]Coordinates from Genbank Accession No. L29277, locus name "HUMAPRF", SEQ ID NO. 1.

Oligonucleotide activity is assayed by quantitation of STAT3 mRNA levels by real-time PCR(RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents are obtained from PE-Applied Biosystems, Foster City, Calif. RT-PCR reactions are carried out by adding 25 μl PCR cocktail (1× TAQMAN7 buffer A, 5.5 mM MgCl$_2$, 300 μM each of dATP, dCTP and dGTP, 600 μM of dUTP, 100 nM each of forward primer, reverse primer, and probe, 20 U RNAse inhibitor, 1.25 units AMPLITAQ GOLD7, and 12.5 U MuLV reverse transcriptase) to 96 well plates containing μl poly(A) mRNA solution. The RT reaction is carried out by incubation for 30 minutes at 48° C. following a 10 minute incubation at 95° C. to activate the AMPLITAQ GOLD7, 40 cycles of a two-step PCR protocol are carried out: 95° C. for 15 seconds (denaturation) followed by 60° C. for 1.5 minutes (annealing/extension).

STAT3 PCR primers and a probe can be designed using commercial software (e.g. Oligo 5.0).

Example 3

Mouse STAT3 Oligonucleotide Sequences

Antisense oligonucleotides were designed to target mouse STAT3. Target sequence data are from the STAT3 cDNA sequence submitted by Zhong, Z.; Genbank accession number U06922, provided herein as SEQ ID NO: 82. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines were 5-methyl-cytosines. Oligonucleotide sequences are shown in Table 3.

The B lymphoma cell line, BCL1 was obtained from ATCC (Rockville, Md.). BCL1 cells were cultured in RPMI 1640 medium.

BCL1 cells (5×10$^6$ cells in PBS) were transfected with oligonucleotides by electroporation, at 200V, 1000° F. using a BTX Electro Cell Manipulator 600 (Genetronics, San Diego, Calif.). For an initial screen, BCL1 were electroporated with 10 μM oligonucleotide and RNA collected 24 hours later. Controls without oligonucleotide were subjected to the same electroporation conditions.

Total cellular RNA was isolated using the RNEASY7 kit (Qiagen, Santa Clarita, Calif.). RNAse protection experiments were conducted using RIBOQUANT™ kits and template sets according to the manufacturer's instructions (Pharmingen, San Diego, Calif.). Northern blotting was performed as described in Chiang, M-Y. et al. (J. Biol. Chem., 1991, 266, 18162-18171), using a rat cDNA probe prepared by Xho I/Sal I restriction digest of psysport-1 plasmid (ATCC, Rockville, Md.). mRNA levels were quantitated using a PhosphorImager (Molecular Dynamics, Sunnyvale, Calif.).

TABLE 3

Nucleotide Sequences of Mouse STAT3 Chimeric (deoxy gapped) Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17136 | GTTCCACTGAGCCATCCTGC | 83 | 0064-0083 | AUG |
| 17137 | TTCAGGTAGCGTGTGTCCAG | 84 | 0096-0115 | coding |
| 17138 | ATGTGACTCTTTGCTGGCTG | 85 | 0205-0224 | coding |
| 17139 | CCAAGAGATTATGAAACACC | 86 | 0233-0252 | coding |
| 17140 | GCTCCAACATCTGCTGCTTC | 87 | 0485-0504 | coding |
| 17141 | GCTCTTCATCAGTCAGTGTC | 88 | 0767-0786 | coding |
| 17142 | ATCTGACACCCTGAGTAGTT | 89 | 1680-1699 | coding |
| 17143 | GCCAGACCCAGAAGGAGAAG | 90 | 1742-1761 | coding |
| 17144 | CGCTCCTTGCTGATGAAACC | 91 | 1827-1846 | coding |
| 17145 | AACTTGGTCTTCAGGTACGG | 92 | 2178-2197 | coding |

TABLE 3-continued

Nucleotide Sequences of Mouse STAT3 Chimeric (deoxy gapped) Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17146 | ATCAATGAATCTAAAGTGCG | 93 | 2253-2272 | coding |
| 17147 | TCAGCACCTTCACCGTTATT | 94 | 2283-2302 | coding |
| 17148 | ACTCAAACTGCCCTCCTGCT | 95 | 2309-2328 | coding |
| 17149 | GGTTTCAGCTCCTCACATGG | 96 | 2374-2393 | STOP |
| 17150 | TAAAAAAAAAATCTGGAAC | 97 | 2485-2504 | 3'-UTR |
| 17151 | AAGATAGCAGAAGTAGGAAA | 98 | 2506-2525 | 3'-UTR |
| 17152 | AAAAAGTGCCCAGATTGCCC | 99 | 2527-2546 | 3'-UTR |
| 17153 | ATCACCCACACTCACTCATT | 100 | 2557-2645 | 3'-UTR |
| 17154 | CCTTTGCCTCCCTTCTGCTC | 101 | 2626-2645 | 3'-UTR |
| 17155 | TGAAAAGGAGGGCAGGCGG | 102 | 2665-2684 | 3'-UTR |
| 17156 | CACCAGGAGGCACTTGTCTA | 103 | 2705-2724 | 3'-UTR |
| 17157 | AACCTCCTGGGCTTAGTCCT | 104 | 2822-2841 | 3'-UTR |
| 23176 | AAAAAGTGCGCAGATTGCCC | 1051 | base mismatch control | |
| 23177 | AAAAAGTCCGCTGATTGCCC | 1063 | base mismatch control | |
| 23178 | AAAAACTCCGCTGAATGCCC | 1075 | base mismatch control | |

[1]All 2'-MOE cytosine residues are 5-methyl-cytosines; all linkages are phosphorothioate linkages.
[2]Co-ordinates from Genbank Accession No. U06922, locus name "MMU06922", SEQ ID NO. 82.

Results are shown in Table 4. Oligonucleotides 17138 (SEQ ID NO. 85), 17139 (SEQ ID NO. 86), 17140 (SEQ ID NO. 87), 17143 (SEQ ID NO. 90), 17144 (SEQ ID NO. 91), 17152 (SEQ ID NO. 99), 17153 (SEQ ID NO. 100), 17156 (SEQ ID NO. 103), and 17157 (SEQ ID NO. 104) gave better than 45% inhibition in this assay.

TABLE 4

Inhibition of Mouse STAT3 mRNA expression in BCL1 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 17136 | 83 | AUG | 75% | 25% |
| 17137 | 84 | coding | 75% | 25% |
| 17138 | 85 | coding | 37% | 63% |
| 17139 | 86 | coding | 41% | 59% |
| 17140 | 87 | coding | 40% | 60% |
| 17141 | 88 | coding | 62% | 38% |
| 17142 | 89 | coding | 70% | 30% |
| 17143 | 90 | coding | 42% | 58% |
| 17144 | 91 | coding | 55% | 45% |
| 17145 | 92 | coding | 89% | 11% |
| 17146 | 93 | coding | 91% | 9% |
| 17147 | 94 | coding | 70% | 30% |
| 17148 | 95 | coding | 69% | 31% |
| 17149 | 96 | STOP | 70% | 30% |
| 17150 | 97 | 3'-UTR | 95% | 5% |
| 17151 | 98 | 3'-UTR | 92% | 8% |
| 17152 | 99 | 3'-UTR | 25% | 75% |
| 17153 | 100 | 3'-UTR | 44% | 56% |
| 17154 | 101 | 3'-UTR | 80% | 20% |
| 17155 | 102 | 3'-UTR | 78% | 22% |
| 17156 | 103 | 3'-UTR | 40% | 60% |
| 17157 | 104 | 3'-UTR | 53% | 47% |

Example 4

Dose Response of Antisense Chimeric (Deoxy Gapped) Phosphorothioate Oligonucleotide Effects on Mouse STAT3 Protein Levels in BCL1 Cells ISIS 17152 (SEQ ID. NO. 99) was chosen for further study. The effect of this oligonucleotide on protein levels was determined by Western blot. ISIS 23177 (SEQ ID NO. 106), a 3 base mismatch, was used as a control. BCL1 cells were grown, treated and processed as described in Example 2.

Nuclear extracts from primary B cells and B lymphoma cell lines were prepared as described in Karras, J. G., et al. (*J. Exp. Med.*, 1997, 185, 1035-1042).

Western blotting was performed as described in Karras, J. G. et al. (*J. Immunol.*, 1996, 157, 2299). STAT1 and STAT3 antibodies were obtained from UBI (Lake Placid, N.Y.).

Results are shown in Table 5. ISIS 17152 (SEQ ID NO. 99) was significantly better at reducing STAT3 protein levels than the mismatch control.

TABLE 5

Dose Response of BCL1 cells to STAT3 Chimeric (deoxy gapped) Phosphorothioate Oligonucleotides

| ISIS # | SEQ ID NO: | ASO Gene Target | Dose | % protein Expression | % protein Inhibition |
|---|---|---|---|---|---|
| control | — | — | — | 100% | — |
| 17152 | 99 | 3'-UTR | 10 nM | 41.7% | 58.3% |
| " | " | " | 15 nM | 42.5% | 57.5% |
| " | " | " | 20 nM | 26.5% | 73.5% |
| 23177 | 106 | control | 10 nM | 75.1% | 24.9% |
| " | " | " | 15 nM | 67.6% | 32.4% |
| " | " | " | 20 nM | 62.6% | 37.4% |

Example 5

Inhibition of BCL1 Proliferation by STAT3 Antisense Chimeric (Deoxy Gapped) Phosphorothioate Oligonucleotide The effect of ISIS 17152 (SEQ ID NO. 99) on BCL1 proliferation was determined BCL1 cells contain constitutively active STAT3 which is thought to be responsible for their proliferation. BCL1 cells were grown, treated and processed as described in Example 2.

$1\times10^5$ BCL1 cells were incubated in 96-well plates in 200 μL complete RPMI following electroporation. Cultures were pulsed with 1 μCi of [$^3$H]-thymidine for the last 8 hours of culture and cells were harvested and analyzed for thymidine incorporation as described in Francis, D. A. et al. (*Int. Immunol.*, 1995, 7, 151-161) 48 hours after electroporation.

Results are shown in Table 6. ISIS 17152 (SEQ ID NO. 99) was able to reduce BCL1 cell proliferation by approximately 50% whereas the mismatch control had no effect.

TABLE 6

Inhibition of BCL1 Cell Proliferation with STAT3 Chimeric (deoxy gapped) Phosphorothioate Oligonucleotides

| ISIS # | SEQ ID NO: | ASO Gene Target | Dose | % Cell Proliferation | % Cell Inhibition |
|---|---|---|---|---|---|
| control | — | — | — | 100% | — |
| 17152 | 99 | 3'-UTR | 10 nM | 78.5% | 21.5% |
| " | " | " | 15 nM | 54.4% | 45.6% |
| " | " | " | 20 nM | 50.2% | 49.8% |
| 23177 | 106 | control | 10 nM | 117.0% | — |
| " | " | " | 15 nM | 99.7% | 0.3% |
| " | " | " | 20 nM | 107.0% | — |

Example 6

Inhibition of BCL1 IgM Secretion by STAT3 Antisense Chimeric (Deoxy Gapped) Phosphorothioate Oligonucleotides The effect of ISIS 17152 (SEQ ID. NO. 99) on IgM secretion levels was determined STAT3 has been implicated in regulation of IgM expression (Faris, M., et al., *Immunology*, 1997, 90, 350-357). BCL1 cells were grown, treated and processed as described in Example 2.

1×10⁶ BCL1 cells were incubated in 12-well plates in 2 mL complete RPMI following electroporation. Supernatant was replaced at 24 hour post electroporation with fresh medium. 48 hours later, supernatants were harvested, centrifuged to remove cells, and assayed for IgM content using the OPT-EIA™ ELISA kit (Pharmingen, San Diego, Calif.) and capture and detecting antibodies for mouse IgM (Southern Biotechnology, Birmingham, Ala.).

Results are shown in Table 7. ISIS 17152 (SEQ ID NO. 99) was significantly better at reducing IgM secretion than the mismatch control.

TABLE 7

Inhibition of BCL1 IgM secretion by STAT3 Chimeric (deoxy gapped) Phosphorothioate Oligonucleotides

| ISIS # | SEQ ID NO: | ASO Gene Target | Dose | % IgM Expression | % IgM Inhibition |
|---|---|---|---|---|---|
| control | — | — | — | 100% | — |
| 17152 | 99 | 3'-UTR | 5 nM | 34.2% | 65.8% |
| " | " | " | 15 nM | 23.1% | 76.9% |
| 23177 | 106 | control | 5 nM | 110.0% | — |
| " | " | " | 15 nM | 80.8% | 19.2% |

Example 7

Induction of Chemokines in BCL1 Cells Following Treatment with STAT3 Antisense Chimeric (Deoxy Gapped) Phosphorothioate Oligonucleotide The effect of ISIS 17152 (SEQ ID. NO. 99) on chemokine levels was determined. BCL1 cells were grown, treated and processed as described in Example 2. Chemokine gene expression was induced in BCL1 cells by addition of 10 μM of a CpG-containing oligonucleotide to the media 16 hours following antisense oligonucleotide electroporation. CpG-containing oligonucleotides are immune-stimulatory (Krieg, A. M., et al., *Nature*, 1995, 374, 546-549). The levels of chemokines were measured eight hours later using RNase protection assay as described in Example 2 with a mouse chemokine template set, Mck-5 (Pharmingen, San Diego, Calif.).

Results are shown in Table 8. ISIS 17152 (SEQ ID. NO. 99) was able to induce the expression of the chemokines, RANTES, MIP-1α and MIP-1β whereas the mismatch control had minimal effect.

TABLE 8

Induction of Chemokines in BCL1 Cells Following Treatment with STAT3 Chimeric (deoxy gapped) Phosphorothioate Oligonucleotides

| ISIS # | SEQ ID NO: | ASO Gene Target | Dose | % RANTES mRNA | % MIP1a mRNA | % MIP1b mRNA |
|---|---|---|---|---|---|---|
| control | — | — | — | 100% | 100% | 100% |
| 17152 | 99 | 3'-UTR | 5 nM | 236% | 201% | 133% |
| " | " | " | 10 nM | 266% | 258% | 150% |
| " | " | " | 20 nM | 257% | 254% | 159% |
| 23178 | 107 | control | 5 nM | 96% | 123% | 96.5% |
| " | " | " | 10 nM | 70.2% | 116% | 87.1% |
| " | " | " | 20 nM | 56% | 106% | 73.3% |

Example 8

Effect of STAT3 Antisense Oligonucleotides in a Murine Model for Rheumatoid Arthritis Collagen-induced arthritis (CIA) is used as a murine model for arthritis (Mussener, A., et al., *Clin. Exp. Immunol.*, 1997, 107, 485-493). Female DBA/1LacJ mice (Jackson Laboratories, Bar Harbor, Me.) between the ages of 6 and 8 weeks are used to assess the activity of STAT3 antisense oligonucleotides.

On day 0, the mice are immunized at the base of the tail with 100 μg of bovine type II collagen which is emulsified in Complete Freund's Adjuvant (CFA). On day 7, a second booster dose of collagen is administered by the same route. On day 14, the mice are injected subcutaneously with 100 μg of LPS. Oligonucleotide is administered intraperitoneally daily (10 mg/kg bolus) starting on day-3 and continuing for the duration of the study.

Weights are recorded weekly. Mice are inspected daily for the onset of CIA. Paw widths are rear ankle widths of affected and unaffected joints and are measured three times a week using a constant tension caliper. Limbs are clinically evaluated and graded on a scale from 0-4 (with 4 being the highest).

Example 9

Effect of STAT3 Antisense Oligonucleotides on Growth of Human MDA-MB231 Tumors in Nude Mice MDA-MB231 human breast carcinoma cells are obtained from the American Type Culture Collection (Bethesda, Md.). Serially transplanted MDA-MB231 tumors are established subcutaneously in nude mice. Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligonucleotides at 6 mg/kg and 0.6 mg/kg.

Example 10

Effect of STAT3 Antisense Oligonucleotides on U-87 Human Glioblastoma Cells Following Subcutaneous Xenografts into Nude Mice The U-87 human glioblastoma cell line is obtained from the ATCC (Rockville Md.) and maintained in Iscove's DMEM medium supplemented with heat-inactivated 10% fetal calf serum. Nude mice are injected subcutaneously with $2 \times 10^7$ cells. Mice are injected intraperitoneally with STAT3 antisense oligonucleotides at dosages of either 2 mg/kg or 20 mg/kg for 21 consecutive days beginning 7 days after xenografts are implanted. Tumor volumes are measured on days 14, 21, 24, 31 and 35. Activity is measured by reduced tumor volume compared to saline or sense oligonucleotide control.

Example 11

Effect of STAT3 Antisense Oligonucleotides on Intracerebral U-87 Glioblastoma Xenografts into Nude Mice U-87 cells are implanted in the brains of nude mice. Mice are treated via continuous intraperitoneal administration of STAT3 antisense oligonucleotides at 20 mg/kg, control sense oligonucleotide (20 mg/kg) or saline beginning on day 7 after xenograft implantation. Activity of the STAT3 antisense oligonucleotides is measured by an increase in survival time compared to controls.

Example 12

Additional Antisense Oligonucleotides Targeted to Human STAT3

An additional set of oligonucleotides targeted to SEQ ID NO: 1 was designed and synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides (shown in bold). The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 9.

TABLE 9

Nucleotide Sequences of Additional Chimeric (deoxy gapped) Phosphorothioate Oligonucleotides targeted to Human STAT3

| ISIS NO. | NUCLEOTIDE SEQUENCE[1] (5' -> 3') | TARGET GENE NUCLEOTIDE CO-ORDINATES[2] | GENE TARGET REGION | SEQ ID NO: |
|---|---|---|---|---|
| 113169 | ATGTGATTCTTTGCTGGCCG | 357 | 5' UTR | 108 |
| 113170 | AGCTGATTCCATTGGGCCAT | 221 | AUG | 109 |
| 113171 | CCAGGAGATTATGAAACACC | 385 | Coding | 110 |

TABLE 9-continued

Nucleotide Sequences of Additional Chimeric (deoxy gapped) Phosphorothioate Oligonucleotides targeted to Human STAT3

| ISIS NO. | NUCLEOTIDE SEQUENCE[1] (5' -> 3') | TARGET GENE NUCLEOTIDE CO-ORDINATES[2] | GENE TARGET REGION | SEQ ID NO: |
|---|---|---|---|---|
| 113172 | ACCGTGTGTCAAGCTGCTGT | 241 | Coding | 111 |
| 113173 | CCATTGGGAAGCTGTCACTG | 286 | Coding | 112 |
| 113174 | TGTGATTCTTTGCTGGCCGC | 356 | Coding | 113 |
| 113175 | GCGGCTATACTGCTGGTCAA | 411 | Coding | 114 |
| 113176 | GCTCCAGCATCTGCTGCTTC | 637 | Coding | 115 |
| 113177 | GATTCTTCCCACAGGCACCG | 539 | Coding | 116 |
| 113178 | TGATTCTTCCCACAGGCACC | 540 | Coding | 117 |
| 113179 | ATCCTGAAGGTGCTGCTCCA | 651 | Coding | 118 |
| 113180 | CGGACATCCTGAAGGTGCTG | 656 | Coding | 119 |
| 113181 | CCCGCCAGCTCACTCACGAT | 869 | Coding | 120 |
| 113182 | AGTCAGCCAGCTCCTCGTCC | 928 | Coding | 121 |
| 113183 | CCAGTCAGCCAGCTCCTCGT | 930 | Coding | 122 |
| 113184 | CGCCTCTTCCAGTCAGCCAG | 938 | Coding | 123 |
| 113185 | GGCCGGTGCTGTACAATGGG | 1109 | Coding | 124 |
| 113186 | ATCCTCTCCTCCAGCATCGG | 1127 | Coding | 125 |
| 113187 | CCGCTCCACCACAAAGGCAC | 1176 | Coding | 126 |
| 113188 | CGTCCCCAGAGTCTTTGTCA | 1324 | Coding | 127 |
| 113189 | TTGTGTTTGTGCCCAGAATG | 1375 | Coding | 128 |
| 113190 | GCTCGGCCCCCATTCCCACA | 1472 | Coding | 129 |
| 113191 | AGGCATTTGGCATCTGACAG | 1621 | Coding | 130 |
| 113192 | CTTGGGATTGTTGGTCAGCA | 1665 | Coding | 131 |
| 113193 | CTCGGCCACTTGGTCCCAGG | 1719 | Coding | 132 |
| 113194 | CCCCGCTTGGTGGTGGACGA | 1757 | Coding | 133 |
| 113195 | CCCCCGCTTGGTGGTGGACG | 1758 | Coding | 134 |
| 113196 | GGAGAAGCCCTTGCCAGCCA | 1881 | Coding | 135 |
| 113197 | TTCATTCCAAAGGGCCAAGA | 1947 | Coding | 136 |
| 113198 | CCCGCTCCTTGCTGATGAAA | 1981 | Coding | 137 |
| 113199 | GTGCTCAAGATGGCCCGCTC | 2000 | Coding | 138 |
| 113200 | CCAAGTGAAAGTGACGCCT | 2071 | Coding | 139 |
| 113201 | ACCCAAGTGAAAGTGACGCC | 2072 | Coding | 140 |
| 113202 | CCGAATGCCTCCTCCTTGGG | 2252 | Coding | 141 |
| 113203 | GCCGACAATACTTCCCGAAT | 2266 | Coding | 142 |
| 113204 | GATGCTCCTGGCTCTCTGGC | 2284 | Coding | 143 |
| 113205 | TCAATGAATCTAAAGCGCGG | 2404 | Coding | 144 |
| 113206 | GACTCAAACTGCCCTCCTGC atcacccaca ttcactcatt | 2462 | Coding | 145 |

TABLE 9-continued

Nucleotide Sequences of Additional Chimeric (deoxy gapped) Phosphorothioate Oligonucleotides targeted to Human STAT3

| ISIS NUCLEOTIDE NO. | SEQUENCE[1] (5' -> 3') | TARGET GENE NUCLEOTIDE CO-ORDINATES[2] | GENE TARGET REGION | SEQ ID NO: |
|---|---|---|---|---|
| 113207 | ATCACCCACATTCACTCATT | 2710 | 3' UTR | 146 |
| 113208 | AAAAGTGCCCAGATTGC | 2682 | 3' UTR | 147 |
| 113209 | AAAAGTGCCCAGATTGCTCA | 2679 | 3' UTR | 148 |
| 113210 | TAAAAGTGCCCAGATTGCTC | 2680 | 3' UTR | 149 |
| 113211 | AAGCAGATCACCCACATTCA | 2716 | 3' UTR | 150 |

These oligonucleotides were screened by Northern blot analysis in U266 cells at an oligonucleotide concentration of 2.5 μM. U266 human myeloma cell lines (originally obtained from American Type Culture Collection) were maintained in RPMI 1640 medium supplemented with 10% fetal calf serum. Cells (15×106 cells in PBS) were transfected with oligonucleotides at 200V with a single 6-millisecond pulse using a BTX Electro Square Porator T820 (Genetronics, San Diego Calif.). The cells were incubated for 24 hours before RNA extraction.

Total cellular RNA was isolated using the Rneasy kit (Qiagen, Santa Clarita, Calif.). Northern blotting was performed on 15 μg of RNA using a cDNA probe prepared from MB-MDA 468 RNA by standard RT-PCR followed by a nested primer reaction. Signals were quantitated using a Molecular Dynamics Phosphorimager.

Results for selected compounds (expressed as percent of control mRNA expression and percent inhibition of mRNA expression) are shown in Table 10.

TABLE 10

Inhibition of Human STAT3 mRNA expression in U266 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| None | — | — | 100 | — |
| 17148 | 95 | Coding | 95.1 | 4.9 |
| 17152 | 99 | 3'UTR | 82.5 | 17.5 |
| 113170 | 109 | AUG | 89.6 | 10.4 |
| 113171 | 110 | Coding | 110.2 | — |
| 113172 | 111 | Coding | 96.1 | 3.9 |
| 113173 | 112 | Coding | 119 | — |
| 113175 | 114 | Coding | 75.8 | 24.2 |
| 113176 | 115 | Coding | 72.3 | 27.7 |
| 113178 | 117 | Coding | 143.9 | — |
| 113181 | 120 | Coding | 105.4 | — |
| 113184 | 123 | Coding | 104.3 | — |
| 113187 | 126 | Coding | 55.9 | 44.1 |
| 113189 | 128 | Coding | 163.9 | — |
| 113199 | 139 | Coding | 64.4 | 35.6 |
| 113207 | 146 | 3'UTR | 123.6 | — |
| 113209 | 148 | 3'UTR | 71.4 | 28.6 |
| 113210 | 149 | 3'UTR | 72.2 | 27.8 |
| 113211 | 150 | 3'UTR | 116.5 | — |

Dose-response experiments were conducted for ISIS 113176, 129987, 113187, 129991, 113209, 129995, 113210 and 129999 as well as ISIS 17148 and the mouse STAT3 oligo ISIS 114054. Results are shown in Table 11.

TABLE 11

Percent inhibition of human STAT3 mRNA expression with antisense oligonucleotides-dose response

| | | Percent inhibition of STAT3 expression | | |
|---|---|---|---|---|
| | SEQ ID | Oligo concentration | | |
| ISIS # | NO: | 2.5 μM | 5 μM | 10 μM |
| 17148 | 95 | 8 | 54 | 60 |
| 114054 | | 4 | 17 | 15 |
| 113176 | | 33 | 67 | 79 |
| 129987 | | 5 | 5 | 29 |
| 113187 | | 44 | 56 | 75 |
| 129991 | | 21 | 22 | 26 |
| 113209 | | 43 | 54 | 73 |
| 129995 | | 5 | 32 | 25 |
| 113210 | | 36 | 50 | 76 |
| 129999 | | 31 | 8 | — |

ISIS 17148, 113176, 113187, 113209 and 113210 were shown to reduce STAT3 expression by over 50% at one or more oligonucleotide concentrations. These compounds are therefore preferred.

Example 13

Antisense Inhibition of STAT3 Causes Apoptotic Cell Death in Mouse Melanoma Cells Mouse B16 melanoma cells were grown in RPMI 1640 (Life Technologies, Inc., Grand Island, N.Y.) medium supplemented with 10% fetal bovine serum, 2 mM L-glutamine, 1 mM sodium pyruvate, 1% MEM nonessential amino acids and 100 IU/ml penicillin/streptomycin.

Cells were treated with ISIS 17152, targeted to mouse STAT3, or the 3-base mismatch control, ISIS 28084 (AAAAAGAGGCCTGATTGCCC; SEQ ID NO: 151). Cells were transfected with oligonucleotide using LipofectAMINE PLUSJ reagent (GibcoBRL). Oligonucleotide was pre-complexed with LipofectAMINE PLUSJ by adding the oligonucleotide to 100 μl serum-free RPMI 1640 medium, then 6 μl LipofectAMINE PLUSJ reagent was added, the sample was mixed well and incubated for 15 minutes at room temperature. An additional 4 μl of LipofectAMINE PLUSJ reagent was diluted to 100 μl in serum-free RPMI. This diluted LipofectAMINE PLUSJ was mixed with the pre-complexed oligonucleotide/LipofectAMINE PLUSJ mixture and incubated for 15 minutes at room temperature. 800 μl of serum-free RPMI 1640 was added, and the resulting oligonucleotide-LipofectAMINE PLUSJ-medium mixture (approximately 1 ml) was added to cells in a 6-well plate. After 3 hours incubation, 1 ml of RPMI 1640 supplemented with 20% fetal bovine serum was added. Oligonucleotide concentrations were 200 nM or 300 nM.

24 hours after transfection, cells were counted to determine the effect of antisense treatment on cell death. Cells were harvested at 24 hours post transfection for western blot analysis and at 48 hours post-transfection for Annexin-V staining for apoptosis.

Effects of oligonucleotide on cell number are shown in Table 12.

TABLE 12

Effect of antisense inhibition of STAT3 on cell number

| | 200 nM | | 300 nM | |
|---|---|---|---|---|
| Expt | ISIS 28084 (3 mismatch) | ISIS 17152 | ISIS 28084 (3 mismatch) | ISIS 17152 |
| 1 | $10.2 \times 10^5$ | $3.8 \times 10^5$ | | |
| 2 | $5.0 \times 10^5$ | $6.8 \times 10^5$ | $9.1 \times 10^5$ | $3.5 \times 10^5$ |
| 3 | $3.5 \times 10^5$ | $1.8 \times 10^5$ | $3.3 \times 10^5$ | $2.2 \times 10^5$ |

Thus treatment with STAT3 antisense oligonucleotide increased cell death (decreased cell number).

Apoptosis in B16 cells was measured by staining with Annexin V-PE (Clontech) and flow cytometry analysis 48 hours after antisense treatment. Positive staining for Annexin-V indicates apoptosis is occurring. Mock-transfected cells and control oligonucleotide-treated cell cultures had 11.37% and 10.15% of cells staining positive for Annexin-V. In contrast, ISIS 17152-treated cells were 29.84% positive for Annexin-V, indicating a nearly threefold increase in apoptotic cells. It should be noted that in general, the percent of apoptosis in B16 cells is likely to have been underestimated since detached dead cells are washed off in processing.

Western blot analysis was done on cells 24 hours after antisense treatment, using an anti-STAT3 antibody (K15, Santa Cruz Biotechnology, Santa Cruz, Calif.). ISIS 17152 at 200 nM or 300 nM significantly reduced STAT3 protein production in B16 cells.

Example 14

Effect of STAT3 Antisense Oligonucleotides on Melanoma Tumors

Six-week-old female C57BL mice were purchased from the National Cancer Center (Frederick Md.) and maintained under approved conditions. Mice were shaved in the left flank area and injected subcutaneously with $2 \times 10^5$ B16 melanoma cells in 100 µl of PBS. After 7-10 days, B16 tumors with a diameter of 3-6 mm were established. Tumor volume was calculated according to the formula $V=0.52 \times a^2 \times b$ (a, smallest superficial diameter; b, largest superficial diameter).

Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligonucleotides at 6 mg/kg and 0.6 mg/kg.

Example 15

Effect of STAT3 Antisense Oligonucleotides on Leukemic Large Granular Lymphocytes (LGL)

LGL leukemia is a lymphoproliferative disease with autoimmune features and LGL cells are known to be insensitive to Fas-dependent cell death despite high levels of Fas and FasL expression. (Lamy et al., *Blood*, 1998, 92, 4771-7). STAT3 antisense oligonucleotides were tested for their ability to sensitize LGL cells to the apoptotic signal in these cells.

LGL leukemic cells were obtained from patients who met the clinical criteria of T cell (CD3+) LGL leukemia with increased LGL counts and clonal TCR gene rearrangements. All patients had chronic disease not requiring treatment at the time of analysis. Purified leukemic LGL cells were placed in 24-well plates at a concentration of $2 \times 10^6/0.5$ mL of complete medium (RPMI-1640 medium supplemented with 10% fetal bovine serum, 2 mM L-glutamine, 10 U/mL penicillin, and 100 ug/mL streptomycin, all from Gibco Life Technologies, Gaithersburg, Md.). Cells were incubated with either ISIS 17148 antisense oligonucleotide (SEQ ID NO: 95) or the control, ISIS 16094 (SEQ ID NO: 152). Antisense oligonucleotide delivery to LGL leukemic cells was by passive uptake and no transfection reagents were included in the reaction.

Both ISIS 17148 and ISIS 16094 are 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines.

Extracts of LGL cells treated with antisense oligonucleotides (1 uM dosing for ISIS 17148 and the control) from three patients were obtained and assayed for STAT3 protein levels by Western blot. Sensitization of the LGL cells to Fas-mediated apoptosis was also measured by flow cytometry in cells treated with antisense oligonucleotides at doses of 1, 2 and 5 uM. By Western analysis, a reduction in STAT3 protein levels ranged from 25 to 45%. Sensitivity to Fas-mediated apoptosis was also significantly increased in the antisense treated cells and was dose dependent. Measurements of percent specific apoptosis in duplicate reactions revealed an increase in apoptosis from 5% in untreated cells to levels of 6, 17 and 24% in antisense-treated cells at 1, 2, and 5 uM, respectively. Levels of apoptosis in control oligonucleotide treated cells remained at 6% at all doses.

Example 16

Induction of Apoptosis in the Human Myeloma Cell Line U266 Following Stat3 Antisense Oligonucleotide Treatment Methods Cell Culture U266 cells (ATCC, Bethesda, Md.) were cultured in RPMI 1640 medium supplemented with 10% heat-inactivated fetal bovine serum (Sigma Chemical Company, St. Louis, Mo.), 10 mM Hepes, pH 7.2, 50 µM 2-ME, 2 mM L-glutamine, 100 U/ml penicillin, and 100 µg/ml streptomycin (Gibco, Grand Island, N.Y.).

Oligonucleotide Synthesis and Transfection of U266 Cells

2'-O-methoxyethylribose modified phosphorothioate oligonucleotides were synthesized on an automated DNA synthesizer (Applied Biosystems model 380B), as described above. Chimeric oligonucleotides were employed in these studies; the chimeric oligonucleotides contain 2'-O-methoxyethyl modified residues flanking a 2'-deoxynucleotide/phosphorothioate region (gap) that supports RNase H activation. Oligonucleotides were analyzed by capillary gel electrophoresis and judged to be at least 85% full-length material. U266 ($1 \times 10^7$ cells in PBS) were transfected with oligonucleotides by electroporation, at 175V, 1000 μF using a BTX Electro Cell Manipulator 600 (Genetronics, San Diego, Calif.).

Flow Cytometric Analysis of Apoptosis

10×10⁶ U266 cells were electroporated with oligonucleotides and cultured for 48 hours before analysis of phosphatidylserine expression was performed as a measure of apoptosis using the Annexin-V staining kit (Clontech, Palo Alto, Calif.) according to the manufacturer's instructions. Briefly, the cells were resuspended in 0.2 mL of staining buffer (10 mM HEPES, pH 7.4, 140 mM NaCl, 5 mM CaCl₂) and 10 μL of propidium iodide (50 μg/ml) and 5 μL of Annexin V reagent were added at 4° C. for 10 minutes. The samples were then diluted with FacsFlow buffer and analyzed on a Becton Dickinson FACScan (Mountain View, Calif.).

Results

Antisense Inhibition of STAT3 Induces Apoptosis of U266 Multiple Myeloma Cells.

In order to examine the importance of STAT3 expression in multiple myeloma cells, a series of 20mer STAT3 antisense oligonucleotides were designed and synthesized, using phosphorothioate chemistry and incorporating 2'-O-methoxyethyl modifications to improve hybridization affinity and nuclease resistance. Screens performed in U266 MM cells identified several sequences that optimally inhibited STAT3 mRNA expression, as determined by Northern blotting. Two antisense oligonucleotides, ISIS 17148 (SEQ ID NO: 95) and ISIS 113176 (SEQ ID NO: 115) were found to potently inhibit STAT3 mRNA expression in U266 cells following electroporation in a dose-dependent fashion. Control oligonucleotide containing 5 mismatched bases within the 2'-deoxyphosphorothioate central gap region failed to inhibit STAT3 mRNA expression, demonstrating a hybridization-dependent mechanism of target reduction.

Further characterization of the STAT3 antisense oligonucleotides was performed, using Western blotting of nuclear extracts from U266 cells to evaluate STAT3 protein reduction following oligonucleotide transfection. The STAT3 antisense oligonucleotides were found to dose-dependently inhibit STAT3 protein expression in a manner that correlated well with the mRNA inhibition, when evaluated 48 hours after transfection. The five base mismatch control oligonucleotide at the highest dose did not show any effect, further suggesting an antisense mechanism of action.

Previously published data using a dominant negative expression vector encoding STAT3 lacking an intact transactivation domain suggested that STAT3 was a survival factor for MM cells (Catlett-Falcone et al., Immunity 10: 105, 1999). Changes in the proliferative index of STAT3 antisense transfected U266 cells as well as reduced viability in culture following STAT3 antisense transfection led us to determine whether reduction of wild type STAT3 protein would also induce an apoptotic response. Transfection of U266 cells with either ISIS 17148 or 113176 was found to result in increased levels of annexin V staining as assessed by flow cytometry. This effect contrasted to that of control oligonucleotides, either an antisense oligonucleotide targeted to a gene not expressed by U266 cells or the 5 base mismatch control oligonucleotide. These data further support an anti-apoptotic role for STAT3 in multiple myeloma.

Example 17

Design of Phenotypic Assays and In Vivo Studies for the Use of STAT3 Inhibitors

Phenotypic Assays

Once STAT3 inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of STAT3 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with STAT3 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest. Analysis of the genotype of the cell (measurement of the expression of one or more of the genes of the cell) after treatment is also used as an indicator of the efficacy or potency of STAT3 inhibitors. Hallmark genes, or those genes suspected to be associated with a specific disease state, condition, or phenotype, are measured in both treated and untreated cells.

Example 18

Antisense Inhibition of Human STAT3 by Chimeric Phosphorothioate Oligonucleotides Having 2'-MOE Wings and a Deoxy Gap In accordance with the present invention, an additional series of oligonucleotides was designed to target different regions of the human STAT 3, using published sequences (GenBank accession number $L_{29277}$, incorporated herein as SEQ ID NO: 1, the complement of nucleotides 4189213 to 4263636 of the sequence with the GenBank accession number NT_010755.13, incorporated herein as SEQ ID NO: 153 and GenBank accession number NM_139276.1, incorporated herein as SEQ ID NO: 154). The oligonucleotides are shown in Table 13. "Target site" indicates the first (5'-most) nucleotide number on the particular target sequence to which the oligonucleotide binds. All compounds in Table 13 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on STAT3 mRNA levels in A549 cells. The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), 100 units/mL penicillin, and 100 ug/mL streptomycin (Invitrogen Corporation, Carlsbad, Calif.). Cells were routinely passaged by trypsinization and dilution when they reached 90% confluence.

ISIS 18078 was used as a control oligonucleotide and was used at 75 nM. ISIS 18078 (GTGCGCGCGAGCCCGAAATC, SEQ ID NO: 155) is an chimeric oligonucleotide ("gapmers") 20 nucleotides in length, composed of a central "gap" region consisting of nine 2'-deoxynucleotides, which is flanked on both sides (5' and 3' directions) by five-nucleotide and six-nucleotide "wings", respectively. The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

When cells reached 65-75% confluency, they were treated with oligonucleotide. For cells grown in 96-well plates, wells were washed once with 100 L OPTI-MEM-1 reduced-serum medium (Invitrogen Corporation, Carlsbad, Calif.) and then treated with 130 L of OPTI-MEM-1 containing 3.75 g/mL LIPOFECTIN (Invitrogen Corporation, Carlsbad, Calif.) and 75 nM of the compounds in Table 13. Cells were treated and data were obtained in duplicate. Untreated cells served as controls. After 4-7 hours of treatment at 37° C., the medium was replaced with fresh medium. Cells were harvested 16-24 hours after oligonucleotide treatment. STAT3 mRNA levels in A549 cells were quantitated by real-time PCR as described by other methods herein.

Probes and primers to human STAT3 were designed to hybridize to a human STAT3 sequence, using published sequence information (incorporated herein as SEQ ID NO: 1). For STAT 3 the PCR primers were:
forward primer: ACATGCCACTTTGGTGTTTCATAA (SEQ ID NO: 156) reverse primer: TCTTCGTAGATTGTGCTGATAGAGAAC (SEQ ID NO: 157) and the PCR probe was: FAM-CAGTATAGCCGCTTCCTGCAAGAGTC-GAA-TAMRA (SEQ ID NO: 158) where FAM is the fluorescent reporter dye and TAMRA is the quencher dye. This primer probe set is referred to as PPS 199. Gene target quantities obtained by real time RT-PCR are normalized by quantifying total RNA using RiboGreen™ (Molecular Probes, Inc. Eugene, Oreg.). In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

The results of the antisense oligonucleotide treatments are the average of 2 experiments and are shown in Table 13. Data are expressed as percent inhibition relative to untreated control cells.

TABLE 13

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337245 | intron | 153 | 6814 | AGCCTCTGCACCCTCATGTT | 77 | 159 |
| 337246 | intron | 153 | 6868 | CTCCTAAATTAAGAACTTCT | 37 | 160 |
| 337247 | intron | 153 | 14801 | TTTTGCATGATGTAACCACT | 87 | 161 |
| 337248 | intron | 153 | 34820 | TATTGAAAATTATCTAATTC | 0 | 162 |
| 337249 | coding | 153 | 40369 | TTGGGCCATCCTGCTAAAAT | 48 | 163 |
| 337250 | exon:intron | 153 | 50156 | ATTCACTTGCCTCCTTGACT | 51 | 164 |
| 337251 | intron:exon | 153 | 51124 | ATGCCCTTACTCTCCGCATC | 74 | 165 |
| 337252 | exon:intron | 153 | 59140 | CTGAACTTACCCTCTGAGAG | 60 | 166 |
| 337253 | exon:intron | 153 | 64176 | AAATGCGGACCCAAGAGTTT | 49 | 167 |
| 337254 | 5'UTR | 1 | 56 | CTTGTTCCCTCGGCTGCGAC | 57 | 168 |
| 337255 | 5'UTR | 1 | 79 | GCCTGTCCAGGATCCGGTTG | 75 | 169 |
| 337256 | 5'UTR | 1 | 126 | GAAGGGCCTCTCCGAGCCGA | 67 | 170 |
| 337257 | 5'UTR | 1 | 148 | GGCGGCGAGGCTCCCTCAGG | 80 | 171 |
| 337258 | 5'UTR | 1 | 193 | TCCGGCAGAGGCCGAGAGGC | 56 | 172 |
| 337259 | 5'UTR | 154 | 225 | CCATCCTGCTAAAATCAGGG | 58 | 173 |
| 337260 | 5'UTR | 154 | 233 | CCATTGGGCCATCCTGCTAA | 62 | 174 |

TABLE 13-continued

Inhibition of human STAT 3 mRNA levels
by chimeric phosphorothioate oligonucleotides
having 2'-MOE wings and a deoxy gap

| Isis # | Region | Target Seq ID No | Target Site | Sequence | % Inhib | Seq ID No |
|---|---|---|---|---|---|---|
| 337261 | coding | 1 | 235 | TGTCAAGCTGCTGTAGCTGA | 79 | 175 |
| 337262 | coding | 1 | 299 | AACTGCCGCAGCTCCATTGG | 74 | 176 |
| 337263 | coding | 1 | 326 | TCTTGACTCTCAATCCAAGG | 79 | 177 |
| 337264 | coding | 1 | 339 | CGCATATGCCCAATCTTGAC | 81 | 178 |
| 337265 | coding | 1 | 426 | CGACTCTTGCAGGAAGCGGC | 92 | 179 |
| 337266 | coding | 1 | 453 | TCGTAGATTGTGCTGATAGA | 61 | 180 |
| 337267 | coding | 1 | 470 | AGAAACTGCTTGATTCTTCG | 62 | 181 |
| 337268 | coding | 1 | 484 | GATACCTGCTCTGAAGAAAC | 75 | 182 |
| 337269 | coding | 1 | 491 | TTCTCAAGATACCTGCTCTG | 74 | 183 |
| 337270 | coding | 1 | 496 | TTGGCTTCTCAAGATACCTG | 89 | 184 |
| 337271 | coding | 1 | 541 | GTGATTCTTCCCACAGGCAC | 85 | 185 |
| 337272 | coding | 1 | 629 | ATCTGCTGCTTCTCCGTCAC | 74 | 186 |
| 337273 | coding | 1 | 634 | CCAGCATCTGCTGCTTCTCC | 73 | 187 |
| 337274 | coding | 1 | 647 | TGAAGGTGCTGCTCCAGCAT | 74 | 188 |
| 337275 | coding | 1 | 683 | TTCTGTTCTAGATCCTGCAC | 82 | 189 |
| 337276 | coding | 1 | 708 | CTGGAGATTCTCTACCACTT | 91 | 190 |
| 337277 | coding | 1 | 716 | AAGTCATCCTGGAGATTCTC | 79 | 191 |
| 337278 | coding | 1 | 721 | AATCAAAGTCATCCTGGAGA | 69 | 192 |
| 337279 | coding | 1 | 726 | GTTGAAATCAAAGTCATCCT | 78 | 193 |
| 337280 | coding | 1 | 731 | TTATAGTTGAAATCAAAGTC | 45 | 194 |
| 337281 | coding | 1 | 736 | GGGTTTTATAGTTGAAATCA | 16 | 195 |
| 337282 | coding | 1 | 741 | CTTGAGGGTTTTATAGTTGA | 58 | 196 |
| 337283 | coding | 1 | 746 | TGACTCTTGAGGGTTTTATA | 71 | 197 |
| 337284 | coding | 1 | 751 | CTCCTTGACTCTTGAGGGTT | 91 | 198 |
| 337285 | coding | 1 | 756 | CATGTCTCCTTGACTCTTGA | 78 | 199 |
| 337286 | coding | 1 | 768 | ATTCAGATCTTGCATGTCTC | 77 | 200 |
| 337287 | coding | 1 | 779 | TGGTTGTTTCCATTCAGATC | 82 | 201 |
| 337288 | coding | 1 | 790 | TGGTCACTGACTGGTTGTTT | 84 | 202 |
| 337289 | coding | 1 | 812 | TCCAGCTGCTGCATCTTCTG | 83 | 203 |
| 337290 | coding | 1 | 822 | GAGCATCTGTTCCAGCTGCT | 80 | 204 |
| 337291 | coding | 1 | 848 | CTTCTCCGCATCTGGTCCAG | 66 | 205 |
| 337292 | coding | 1 | 899 | TTCTGCACGTACTCCATCGC | 81 | 206 |
| 337293 | coding | 1 | 925 | CAGCCAGCTCCTCGTCCGTG | 92 | 207 |
| 337294 | coding | 1 | 935 | CTCTTCCAGTCAGCCAGCTC | 75 | 208 |
| 337295 | coding | 1 | 941 | TGCCGCCTCTTCCAGTCAGC | 82 | 209 |
| 337296 | coding | 1 | 999 | CCAGTTTTCTAGCCGATCTA | 80 | 210 |

TABLE 13-continued

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337297 | coding | 1 | 1006 | ACGTTATCCAGTTTTCTAGC | 72 | 211 |
| 337298 | coding | 1 | 1025 | AGTTGAGATTCTGCTAATGA | 74 | 212 |
| 337299 | coding | 1 | 1030 | TCTGAAGTTGAGATTCTGCT | 80 | 213 |
| 337300 | coding | 1 | 1085 | CCTTTGTAGGAAACTTTTTG | 23 | 214 |
| 337301 | coding | 1 | 1162 | AGGCACTTTTCATTAAGTTT | 73 | 215 |
| 337302 | coding | 1 | 1262 | TTGACCAGCAACCTGACTTT | 61 | 216 |
| 337303 | coding | 1 | 1286 | AGCTGATAATTCAACTCAGG | 85 | 217 |
| 337304 | coding | 1 | 1291 | TTTTAAGCTGATAATTCAAC | 15 | 218 |
| 337305 | coding | 1 | 1297 | CTTTAATTTTAAGCTGATAA | 25 | 219 |
| 337306 | coding | 1 | 1302 | GCACACTTTAATTTTAAGCT | 77 | 220 |
| 337307 | coding | 1 | 1307 | TCAATGCACACTTTAATTTT | 53 | 221 |
| 337308 | coding | 1 | 1364 | CCCAGAATGTTAAATTTCCG | 70 | 222 |
| 337309 | coding | 1 | 1414 | AGAGGCTGCCGTTGTTGGAT | 73 | 223 |
| 337310 | coding | 1 | 1433 | AAGTGTTTGAATTCTGCAGA | 73 | 224 |
| 337311 | coding | 1 | 1452 | TCTCTGCTCCCTCAGGGTCA | 61 | 225 |
| 337312 | coding | 1 | 1517 | ATCAGGTGCAGCTCCTCAGT | 78 | 226 |
| 337313 | coding | 1 | 1522 | AGGTGATCAGGTGCAGCTCC | 61 | 227 |
| 337314 | coding | 1 | 1527 | CTCAAAGGTGATCAGGTGCA | 75 | 228 |
| 337315 | coding | 154 | 1571 | GAGGCCTTGGTGATACACCT | 46 | 229 |
| 337316 | coding | 154 | 1579 | TCAATCTTGAGGCCTTGGTG | 59 | 230 |
| 337317 | coding | 154 | 1584 | CTAGGTCAATCTTGAGGCCT | 55 | 231 |
| 337318 | coding | 1 | 1569 | GGTCTCTAGGTCAATCTTGA | 74 | 232 |
| 337319 | coding | 1 | 1577 | AAGGAGTGGGTCTCTAGGTC | 38 | 233 |
| 337320 | coding | 154 | 1602 | CTGGCAAGGAGTGGGTCTCT | 74 | 234 |
| 337321 | coding | 154 | 1609 | ACCACAACTGGCAAGGAGTG | 80 | 235 |
| 337322 | coding | 1 | 1609 | TCTGACAGATGTTGGAGATC | 69 | 236 |
| 337323 | coding | 1 | 1614 | TGGCATCTGACAGATGTTGG | 79 | 237 |
| 337324 | coding | 1 | 1619 | GCATTTGGCATCTGACAGAT | 79 | 238 |
| 337325 | coding | 1 | 1667 | TTCTTGGGATTGTTGGTCAG | 75 | 239 |
| 337326 | coding | 1 | 1778 | GTCAGCTGCTCGATGCTCAG | 78 | 240 |
| 337327 | coding | 154 | 1823 | TCCCAAGAGTTTCTCTGCCA | 84 | 241 |
| 337328 | coding | 1 | 1838 | CATGTGATCTGACACCCTGA | 85 | 242 |
| 337329 | coding | 1 | 1843 | TAGCCCATGTGATCTGACAC | 88 | 243 |
| 337330 | coding | 154 | 1885 | GCCATGTTTTCTTTGCAAAA | 59 | 244 |
| 337331 | coding | 1 | 1873 | CCTTGCCAGCCATGTTTTCT | 88 | 245 |
| 337332 | coding | 1 | 1878 | GAAGCCCTTGCCAGCCATGT | 91 | 246 |

TABLE 13-continued

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337333 | coding | 154 | 1903 | AAGGAGAAGCCCTTGCCAGC | 90 | 247 |
| 337334 | coding | 154 | 1908 | CCCAGAAGGAGAAGCCCTTG | 85 | 248 |
| 337335 | coding | 154 | 1918 | TCCAGCCAGACCCAGAAGGA | 86 | 249 |
| 337336 | coding | 1 | 2048 | TCTTTGCTGCTTTCACTGAA | 79 | 250 |
| 337337 | coding | 1 | 2144 | ATGTTGTTCAGCTGCTGCTT | 76 | 251 |
| 337338 | coding | 1 | 2149 | ATGACATGTTGTTCAGCTGC | 80 | 252 |
| 337339 | coding | 1 | 2154 | AGCAAATGACATGTTGTTCA | 84 | 253 |
| 337340 | coding | 1 | 2159 | ATTTCAGCAAATGACATGTT | 72 | 254 |
| 337341 | coding | 1 | 2164 | TGATGATTTCAGCAAATGAC | 74 | 255 |
| 337342 | coding | 1 | 2174 | TTATAGCCCATGATGATTTC | 81 | 256 |
| 337343 | coding | 1 | 2179 | TGATCTTATAGCCCATGATG | 84 | 257 |
| 337344 | coding | 1 | 2184 | ATCCATGATCTTATAGCCCA | 90 | 258 |
| 337345 | coding | 1 | 2190 | GGTAGCATCCATGATCTTAT | 86 | 259 |
| 337346 | coding | 1 | 2232 | AATGTCAGGATAGAGATAGA | 55 | 260 |
| 337347 | coding | 1 | 2246 | GCCTCCTCCTTGGGAATGTC | 88 | 261 |
| 337348 | coding | 154 | 2273 | TCCGAATGCCTCCTCCTTGG | 92 | 262 |
| 337349 | coding | 154 | 2278 | TACTTTCCGAATGCCTCCTC | 65 | 263 |
| 337350 | coding | 154 | 2283 | GACAATACTTTCCGAATGCC | 84 | 264 |
| 337351 | coding | 1 | 2303 | CTACCTGGGTCAGCTTCAGG | 74 | 265 |
| 337352 | coding | 1 | 2333 | ATAAACTTGGTCTTCAGGTA | 80 | 266 |
| 337353 | coding | 1 | 2351 | GTCGTTGGTGTCACACAGAT | 81 | 267 |
| 337354 | coding | 1 | 2356 | TGCAGGTCGTTGGTGTCACA | 62 | 268 |
| 337355 | coding | 1 | 2361 | ATTGCTGCAGGTCGTTGGTG | 61 | 269 |
| 337356 | coding | 1 | 2366 | ATGGTATTGCTGCAGGTCGT | 75 | 270 |
| 337357 | coding | 1 | 2371 | GGTCAATGGTATTGCTGCAG | 71 | 271 |
| 337358 | coding | 1 | 2381 | GACATCGGCAGGTCAATGGT | 77 | 272 |
| 337359 | coding | 154 | 2423 | CAATGAATCTAAAGTGCGGG | 57 | 273 |
| 337360 | coding | 154 | 2428 | TGCATCAATGAATCTAAAGT | 71 | 274 |
| 337361 | coding | 1 | 2413 | CAAACTGCATCAATGAATCT | 61 | 275 |
| 337362 | coding | 1 | 2418 | ATTTCCAAACTGCATCAATG | 69 | 276 |
| 337363 | coding | 1 | 2456 | AACTGCCCTCCTGCTGAGGG | 63 | 277 |
| 337364 | coding | 1 | 2469 | GGTGAGGGACTCAAACTGCC | 70 | 278 |
| 337365 | 3'UTR | 1 | 2550 | CAGTCGTATCTTTCTGCAGC | 84 | 279 |
| 337366 | 3'UTR | 1 | 2658 | AGATAGCAGAAGTAGGAGAT | 66 | 280 |
| 337367 | 3'UTR | 1 | 2678 | AAAGTGCCCAGATTGCTCAA | 82 | 281 |
| 337368 | 3'UTR | 1 | 2684 | TTTTTAAAAGTGCCCAGATT | 59 | 282 |

TABLE 13-continued

Inhibition of human STAT 3 mRNA levels by chimeric phosphorothioate oligonucleotides having 2'-MOE wings and a deoxy gap

| Isis # | Region | Target Seq ID No | Target Site | Sequence | % Inhib | Seq ID No |
|---|---|---|---|---|---|---|
| 337369 | 3'UTR | 1 | 2713 | CAGATCACCCACATTCACTC | 88 | 283 |
| 337370 | 3'UTR | 1 | 2729 | TGCATTTAGATAAAAGCAGA | 78 | 284 |
| 337371 | 3'UTR | 1 | 2744 | GAACACATCCTTATTTGCAT | 76 | 285 |
| 337372 | 3'UTR | 1 | 2759 | ATCATGGGTCTCAGAGAACA | 88 | 286 |
| 337373 | 3'UTR | 154 | 2790 | CACATCCCCTGATCATGGGT | 70 | 287 |
| 337374 | 3'UTR | 154 | 2826 | AGACATTTCCTTTTTCTCCC | 67 | 288 |
| 337375 | 3'UTR | 154 | 2908 | ACCAGGAGGCACTTGTCTAA | 89 | 289 |
| 337376 | 3'UTR | 154 | 2914 | GCAGGCACCAGGAGGCACTT | 83 | 290 |
| 337377 | 3'UTR | 154 | 2941 | GCTTACAGAAACAGGCAGAA | 78 | 291 |
| 337378 | 3'UTR | 154 | 2959 | AGGTGGCCTGTGGCATTTGC | 16 | 292 |
| 337379 | 3'UTR | 154 | 2971 | GTATGTAGCTATAGGTGGCC | 71 | 293 |
| 337380 | 3'UTR | 154 | 2983 | GCAATGCCAGGAGTATGTAG | 83 | 294 |
| 337381 | 3'UTR | 154 | 2992 | TTAAAAAGTGCAATGCCAGG | 86 | 295 |
| 337382 | 3'UTR | 154 | 3032 | GGCTTAGATAGTCCTATCTT | 84 | 296 |
| 337383 | 3'UTR | 154 | 3047 | TAAAAAGAAACCTAGGGCTT | 81 | 297 |
| 337384 | 3'UTR | 154 | 3108 | ATACAGAAAGGCTATGCTGA | 89 | 298 |
| 337385 | 3'UTR | 154 | 3121 | TTAAGTTTCTTAAATACAGA | 70 | 299 |

As shown in Table 13, SEQ ID Nos 159, 161, 165, 166, 169, 170, 171, 174, 175, 176, 177, 178, 179, 180, 181, 182, 183, 184, 185, 186, 187, 188, 189, 190, 191, 192, 193, 197, 198, 199, 200, 201, 202, 203, 204, 205, 206, 207, 208, 209, 210, 211, 212, 213, 215, 216, 217, 220, 222, 223, 224, 225, 226, 227, 228, 232, 234, 235, 236, 237, 238, 239, 240, 241, 242, 243, 245, 246, 247, 248, 249, 250, 251, 252, 253, 254, 255, 256, 257, 258, 259, 261, 262, 263, 264, 265, 266, 267, 268, 269, 270, 271, 272, 274, 275, 276, 277, 278, 279, 280, 281, 283, 284, 285, 286, 287, 288, 289, 290, 291, 293, 294, 295, 296, 297, 298 and 299 inhibited human STAT3 expression at least 60%.

Example 19

Chimeric Phosphorothioate Oligonucleotides Targeted to Human STAT3 Having 2'-MOE Wings and a Deoxy Gap In accordance with the present invention, an additional series of oligonucleotides was designed to target different regions of the human STAT 3, using published sequences (GenBank accession number L29277, incorporated herein as SEQ ID NO: 1, GenBank accession number NM_139276.1, incorporated herein as SEQ ID NO: 154). The oligonucleotides are shown in Table 14. "Target site" indicates the first (5'-most) nucleotide number on the particular target sequence to which the oligonucleotide binds. All compounds in Table 14 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 14

Chimeric phosphorothioate oligonucleotides targeted to human STAT3 having 2'-MOE wings and a deoxy gap

| Isis # | Region | Target Seq ID No | Target Site | Sequence | Seq ID No |
|---|---|---|---|---|---|
| 345752 | coding | 1 | 631 | GCATCTGCTGCTTCTCCGTC | 300 |
| 345753 | coding | 1 | 633 | CAGCATCTGCTGCTTCTCCG | 301 |
| 345754 | coding | 1 | 635 | TCCAGCATCTGCTGCTTCTC | 302 |
| 345755 | coding | 1 | 636 | CTCCAGCATCTGCTGCTTCT | 303 |
| 345756 | coding | 1 | 638 | TGCTCCAGCATCTGCTGCTT | 304 |
| 345757 | coding | 1 | 641 | TGCTGCTCCAGCATCTGCTG | 305 |
| 345758 | coding | 1 | 643 | GGTGCTGCTCCAGCATCTGC | 306 |
| 345759 | coding | 1 | 645 | AAGGTGCTGCTCCAGCATCT | 307 |
| 345760 | coding | 1 | 1663 | TGGGATTGTTGGTCAGCATG | 308 |

TABLE 14-continued

Chimeric phosphorothioate oligonucleotides targeted to human STAT3 having 2'-MOE wings and a deoxy gap

| Isis # | Region | Target Seq ID No | Target Site | Sequence | Seq ID No |
|---|---|---|---|---|---|
| 345761 | coding | 1 | 1668 | ATTCTTGGGATTGTTGGTCA | 309 |
| 345762 | coding | 1 | 1670 | ACATTCTTGGGATTGTTGGT | 310 |
| 345763 | coding | 1 | 1671 | CACATTCTTGGGATTGTTGG | 311 |
| 345764 | coding | 1 | 1673 | TTCACATTCTTGGGATTGTT | 312 |
| 345765 | coding | 1 | 1675 | AGTTCACATTCTTGGGATTG | 313 |
| 345766 | coding | 1 | 1677 | GAAGTTCACATTCTTGGGAT | 314 |
| 345767 | coding | 1 | 380 | AGATTATGAAACACCAAAGT | 315 |
| 345768 | coding | 1 | 382 | GGAGATTATGAAACACCAAA | 316 |
| 345769 | coding | 1 | 384 | CAGGAGATTATGAAACACCA | 317 |
| 345770 | coding | 1 | 387 | TCCCAGGAGATTATGAAACA | 318 |
| 345771 | coding | 1 | 388 | CTCCCAGGAGATTATGAAAC | 319 |
| 345772 | coding | 1 | 390 | CTCTCCCAGGAGATTATGAA | 320 |
| 345773 | coding | 1 | 392 | ATCTCTCCCAGGAGATTATG | 321 |
| 345774 | coding | 1 | 1872 | CTTGCCAGCCATGTTTTCTT | 322 |
| 345775 | coding | 1 | 1874 | CCCTTGCCAGCCATGTTTTC | 323 |
| 345776 | coding | 1 | 1876 | AGCCCTTGCCAGCCATGTTT | 324 |
| 345777 | coding | 1 | 1880 | GAGAAGCCCTTGCCAGCCAT | 325 |
| 345778 | coding | 1 | 1882 | AGGAGAAGCCCTTGCCAGCC | 326 |
| 345779 | coding | 154 | 1904 | GAAGGAGAAGCCCTTGCCAG | 327 |
| 345780 | coding | 1 | 1877 | AAGCCCTTGCCAGCCATGTT | 328 |
| 345781 | coding | 1 | 1879 | AGAAGCCCTTGCCAGCCATG | 329 |
| 345782 | coding | 154 | 1905 | AGAAGGAGAAGCCCTTGCCA | 330 |
| 345783 | coding | 154 | 1907 | CCAGAAGGAGAAGCCCTTGC | 331 |
| 345784 | coding | 154 | 1909 | ACCCAGAAGGAGAAGCCCTT | 332 |
| 345785 | coding | 1 | 2247 | TGCCTCCTCCTTGGGAATGT | 333 |
| 345786 | coding | 1 | 2249 | AATGCCTCCTCCTTGGGAAT | 334 |
| 345787 | coding | 1 | 2251 | CGAATGCCTCCTCCTTGGGA | 335 |
| 345788 | coding | 154 | 2274 | TTCCGAATGCCTCCTCCTTG | 336 |
| 345789 | coding | 154 | 2275 | TTTCCGAATGCCTCCTCCTT | 337 |
| 345790 | coding | 154 | 2277 | ACTTTCCGAATGCCTCCTCC | 338 |
| 345791 | coding | 1 | 420 | TTGCAGGAAGCGGCTATACT | 339 |
| 345792 | coding | 1 | 422 | TCTTGCAGGAAGCGGCTATA | 340 |
| 345793 | coding | 1 | 424 | ACTCTTGCAGGAAGCGGCTA | 341 |
| 345794 | coding | 1 | 425 | GACTCTTGCAGGAAGCGGCT | 342 |
| 345795 | coding | 1 | 427 | TCGACTCTTGCAGGAAGCGG | 343 |
| 345796 | coding | 1 | 428 | TTCGACTCTTGCAGGAAGCG | 344 |
| 345797 | coding | 1 | 430 | CATTCGACTCTTGCAGGAAG | 345 |
| 345798 | coding | 1 | 2176 | TCTTATAGCCCATGATGATT | 346 |
| 345799 | coding | 1 | 2178 | GATCTTATAGCCCATGATGA | 347 |
| 345800 | coding | 1 | 2180 | ATGATCTTATAGCCCATGAT | 348 |
| 345801 | coding | 1 | 2182 | CCATGATCTTATAGCCCATG | 349 |
| 345802 | coding | 1 | 2186 | GCATCCATGATCTTATAGCC | 350 |
| 345803 | coding | 1 | 2188 | TAGCATCCATGATCTTATAG | 351 |
| 345804 | coding | 1 | 2189 | GTAGCATCCATGATCTTATA | 352 |
| 345805 | 3'UTR | 154 | 3102 | AAAGGCTATGCTGATACAGT | 353 |
| 345806 | 3'UTR | 154 | 3104 | AGAAAGGCTATGCTGATACA | 354 |
| 345807 | 3'UTR | 154 | 3106 | ACAGAAAGGCTATGCTGATA | 355 |
| 345808 | 3'UTR | 154 | 3107 | TACAGAAAGGCTATGCTGAT | 356 |
| 345809 | 3'UTR | 154 | 3109 | AATACAGAAAGGCTATGCTG | 357 |
| 345810 | 3'UTR | 154 | 3110 | AAATACAGAAAGGCTATGCT | 358 |
| 345811 | 3'UTR | 154 | 3112 | TTAAATACAGAAAGGCTATG | 359 |
| 345812 | 3'UTR | 154 | 3114 | TCTTAAATACAGAAAGGCTA | 360 |
| 345813 | 3'UTR | 1 | 2753 | GGTCTCAGAGAACACATCCT | 361 |
| 345814 | 3'UTR | 1 | 2755 | TGGGTCTCAGAGAACACATC | 362 |
| 345815 | 3'UTR | 1 | 2757 | CATGGGTCTCAGAGAACACA | 363 |
| 345816 | 3'UTR | 1 | 2758 | TCATGGGTCTCAGAGAACAC | 364 |
| 345817 | 3'UTR | 1 | 2761 | TGATCATGGGTCTCAGAGAA | 365 |
| 345818 | 3'UTR | 1 | 2763 | CCTGATCATGGGTCTCAGAG | 366 |
| 345819 | 3'UTR | 1 | 2765 | CCCCTGATCATGGGTCTCAG | 367 |
| 345820 | coding | 154 | 1912 | CAGACCCAGAAGGAGAAGCC | 368 |
| 345822 | coding | 154 | 1916 | CAGCCAGACCCAGAAGGAGA | 369 |
| 345823 | coding | 154 | 1917 | CCAGCCAGACCCAGAAGGAG | 370 |
| 345824 | coding | 154 | 1919 | GTCCAGCCAGACCCAGAAGG | 371 |
| 345825 | coding | 154 | 1920 | TGTCCAGCCAGACCCAGAAG | 372 |
| 345826 | coding | 154 | 1922 | ATTGTCCAGCCAGACCCAGA | 373 |
| 345827 | coding | 154 | 1924 | ATATTGTCCAGCCAGACCCA | 374 |
| 345828 | coding | 1 | 2181 | CATGATCTTATAGCCCATGA | 375 |
| 345829 | coding | 1 | 2183 | TCCATGATCTTATAGCCCAT | 376 |
| 345830 | coding | 1 | 2185 | CATCCATGATCTTATAGCCC | 377 |
| 345831 | coding | 1 | 2187 | AGCATCCATGATCTTATAGC | 378 |
| 345832 | coding | 1 | 2191 | TGGTAGCATCCATGATCTTA | 379 |

TABLE 14-continued

Chimeric phosphorothioate oligonucleotides
targeted to human STAT3 having 2'-MOE
wings and a deoxy gap

| Isis # | Region | Target Seq ID No | Target Site | Sequence | Seq ID No |
|---|---|---|---|---|---|
| 345833 | coding | 1 | 2192 | TTGGTAGCATCCATGATCTT | 380 |
| 345834 | coding | 1 | 2196 | GATATTGGTAGCATCCATGA | 381 |

Example 20

Chimeric Phosphorothioate Oligonucleotides Targeted to Mouse STAT3, Having 2'-MOE Wings and a Deoxy Gap In accordance with the present invention, an additional series of oligonucleotides was designed to target different regions of the mouse STAT 3 RNA, using published sequences (GenBank accession number U06922.1, incorporated herein as SEQ ID NO: 82, GenBank accession number U30709.1, incorporated herein as SEQ ID NO: 382). The oligonucleotides are shown in Table 15. "Target site" indicates the first (5'-most) nucleotide number on the particular target sequence to which the oligonucleotide binds. All compounds in Table 15 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 15

Chimeric phosphorothioate oligonucleotides
targeted to mouse STAT3 having 2'-MOE
wings and a deoxy gap

| Isis # | Region | Target Seq ID No | Target Site | Sequence | Seq ID No |
|---|---|---|---|---|---|
| 29800 | coding | 82 | 2213 | TGGTATTGCTGCAGGTCGTT | 383 |
| 29801 | coding | 82 | 2224 | CGGCAGGTCAATGGTATTGC | 384 |

TABLE 15-continued

Chimeric phosphorothioate oligonucleotides
targeted to mouse STAT3 having 2'-MOE
wings and a deoxy gap

| Isis # | Region | Target Seq ID No | Target Site | Sequence | Seq ID No |
|---|---|---|---|---|---|
| 29802 | coding | 82 | 2230 | GGACATCGGCAGGTCAATGG | 385 |
| 29806 | 5'UTR | 382 | 11 | TTGTACCTCAGCGCGGACGC | 386 |
| 134027 | coding | 82 | 2309 | ACTCAAACTGCCCTCCTGCT | 95 |
| 337354 | coding | 82 | 2204 | TGCAGGTCGTTGGTGTCACA | 268 |
| 345821 | coding | 82 | 1742 | GCCAGACCCAGAAGGAGAAG | 90 |

In a further embodiment, an additional series of oligonucleotides was designed to target mouse STAT 3 RNA, using published sequences (GenBank accession number U06922.1, incorporated herein as SEQ ID NO: 82). The compounds are shown in Table 16. "Target site" indicates the first (5'-most) nucleotide number on the particular sequence to which the compound binds. All compounds in Table 16 are chimeric oligonucleotides, composed of a "gap" region consisting of twelve 2'-deoxynucleotides, which is flanked on both sides (5' and 3' directions) by "wings" consisting of 2'-methoxyethyl (2'-MOE)nucleotides. The number of 2'-MOE nucleotides in the gaps vary from a length of 2 to 5 nucleotides, with the 2'-deoxynucleotides in plain type and the 2'-MOE nucleotides in bold type. The exact structure of each oligonucleotide is designated in Table 16 as the "wing" structure. A designation of 5~10~5, for example, indicates that the first and last 5 nucleotides are 2'-MOE nucleotides and the central 10 nucleotides are 2'deoxynucleotides. The internucleoside (backbone) linkages are phosphorothioate (P=S) throughout the oligonucleotide. Unmodified cytidine residues which are underscored; all other cytidine residues are 5-methylcytidines.

TABLE 16

Chimeric phosphorothioate oligonucleotides
targeted to mouse STAT3, having 2'-MOE
wings and a deoxy gap

| ISIS # | Region | TARGET SEQ ID NO | TARGET SITE | SEQUENCE | WING STRUCTURE | SEQ ID NO |
|---|---|---|---|---|---|---|
| 133003 | 3' UTR | 82 | 2527 | AAAAAGTGCCCAGATTGCCC | 5~12~5 | 99 |
| 346030 | 3' UTR | 82 | 2527 | AAAAGTG<u>CCC</u>AGATTGCCC | 4~10~5 | 387 |
| 346031 | 3' UTR | 82 | 2528 | AAAAGTG<u>CCC</u>AGATTGCC | 4~10~4 | 388 |
| 346032 | 3' UTR | 82 | 2528 | AAAGTG<u>CCC</u>AGATTGCC | 3~10~4 | 389 |

In a further embodiment of the present invention, an additional series of oligonucleotides was designed to target different regions of the mouse STAT 3 RNA, using published sequence (GenBank accession number U06922.1, incorporated herein as SEQ ID NO: 82). The oligonucleotides are shown in Table 17. "Target site" indicates the first (5'-most) nucleotide number on the particular target sequence to which the oligonucleotide binds. All compounds in table 17 are uniformly composed of 2'-methoxyethyl (2'-MOE)nucleotides. The internucleoside (backbone) linkages are phosphorothioate (P=S) throughout the oligonucleotide, and all cytidine residues are 5-methylcytidines.

TABLE 17

Phosphorothioated uniform 2'MOE oligonucleotides targeted to mouse STAT3

| Isis # | Region | Target Seq ID No | Target Site | Sequence | Seq ID No |
|---|---|---|---|---|---|
| 29803 | coding | 82 | 2253 | ATCAATGAATCTAAAGTGCG | 93 |
| 29805 | coding | 82 | 2206 | GCTGCAGGTCGTTGGTGTCA | 390 |

Example 21

Antisense Inhibition of Human STAT 3 by Chimeric Oligonucleotides Having 2'-MOE Wings and a Deoxy Gap: Dose Response In accordance with the present invention, a subset of the antisense oligonucleotides targeted to human STAT3 was further investigated in dose-response studies. The compounds were analyzed for their effect on human STAT 3 mRNA levels in T-24 cells.

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

Control oligonucleotides used were ISIS 129695 (TTC-TACCTCGCGCGATTTAC, SEQ ID NO: 391), ISIS 129694 (GTACAGTTATGCGCGGTAGA SEQ ID NO: 392), ISIS 129690 (TTAGAATACGTCGCGTTATG SEQ ID NO: 393), ISIS 129686 (CGTTATTAACCTCCGTTGAA SEQ ID NO: 394), ISIS 116847 (CTGCTAGCCTCTGGATTTGA, SEQ ID NO: 395) and ISIS 113529 (CTCTTACTGTGCTGTG-GACA SEQ ID NO: 396). These are universal scrambled control oligonucleotides.

T-24 cells were treated with 18.75, 37.5, 75, or 150 nM of oligonucleotide mixed with 3 ug/mL LIPOFECTIN per 100 nM oligonucleotide as described by other examples herein. Untreated cells served as controls. Following 16 hours of treatment, RNA was prepared from cells for subsequent real-time PCR analysis.

Human STAT3 mRNA expression levels were quantitated by real-time PCR using primer probe set PPS 199 and gene target quantities were normalized using Ribogreen as described in other examples herein. Data are averages from two experiments are shown in Table 18. A "−" or "+" designation indicates a decrease or increase of STAT 3 mRNA expression, respectively, relative to untreated control cells.

TABLE 18

Inhibition of human STAT 3 mRNA levels by chimeric phosphorothioate oligonucleotides having 2'-MOE wings and a deoxy gap: dose response
Percent change of STAT3 expression using PPS 199

| Isis # | Seq ID No | Oligonucleotide Concentration | | | |
|---|---|---|---|---|---|
| | | 18.75 nM | 37.5 nM | 75 nM | 150 nM |
| 106747 | 58 | −37 | −48 | −71 | −84 |
| 337247 | 161 | −23 | −43 | −62 | −75 |
| 337270 | 184 | −29 | −41 | −67 | −87 |
| 337276 | 190 | −40 | −61 | −76 | −81 |
| 337284 | 198 | −49 | −64 | −69 | −72 |
| 337293 | 207 | −26 | −49 | −66 | −79 |
| 337303 | 217 | −44 | −61 | −69 | −72 |
| 337332 | 246 | −63 | −79 | −87 | −92 |
| 337333 | 247 | −48 | −73 | −82 | −88 |
| 337344 | 258 | −27 | −47 | −63 | −77 |
| 337348 | 262 | −61 | −77 | −82 | −86 |
| 337384 | 298 | −40 | −55 | −71 | −80 |
| 129695 | 391 | +5 | +2 | +8 | 0 |
| 129694 | 392 | +4 | −3 | −4 | −10 |
| 129690 | 393 | +2 | +7 | +6 | +8 |
| 129686 | 394 | +2 | +1 | −5 | +1 |
| 116847 | 395 | +7 | +4 | +8 | +5 |
| 113529 | 396 | +1 | −1 | −11 | −26 |

As shown in Table 18, the compounds tested inhibit human STAT3 mRNA expression in a dose-dependent manner.

The dose-response was repeated in T-24 cells and gene target quantities were measured using a different primer-probe set, called PPS 2033 herein. PPS 2033 comprises probes and primers to human STAT3 were designed to hybridize to a human STAT3 sequence, using published sequence information (incorporated herein as SEQ ID NO: 154). For PPS 2033 the PCR primers were:

forward primer: GAGGCCCGCCCAACA (SEQ ID NO: 397) reverse primer: TTCTGCTAATGACGTTATC-CAGTTTT (SEQ ID NO: 398) and the PCR probe was: FAM-CTGCCTAGATCGGC-TAMRA (SEQ ID NO: 399) where FAM is the fluorescent reporter dye and TAMRA is the quencher dye. Gene target quantities obtained by real time RT-PCR are normalized by quantifying total RNA using RiboGreen™ (Molecular Probes, Inc. Eugene, Oreg.). Control oligonucleotides used were ISIS 129695 (SEQ ID NO: 391), ISIS 129694 (SEQ ID NO: 392), ISIS 129690 (SEQ ID NO: 393), ISIS 129686 (SEQ ID NO: 394), ISIS 116847 (SEQ ID NO: 395) and ISIS 113529 (SEQ ID NO: 396).

T-24 cells were treated with 18.75, 37.5, 75, or 150 nM of oligonucleotide mixed with 3 ug/mL LIPOFECTIN per 100 nM oligonucleotide as described by other examples herein. Untreated cells served as controls. Following 16 hours of treatment, RNA was prepared from cells for subsequent real-time PCR analysis.

Human STAT3 mRNA expression levels were quantitated by real-time PCR using primer probe set PPS 2033 and gene target quantities were normalized using Ribogreen as described in other examples herein. Data are averages from two experiments are shown in Table 19. A "−" or "+" designation indicates a decrease or increase of STAT 3 mRNA expression, respectively, relative to untreated control cells.

TABLE 19

Inhibition of human STAT 3 mRNA levels by chimeric
phosphorothioate oligonucleotides having 2'-MOE
wings and a deoxy gap: dose response
Percent change of STAT3 expression using PPS 2033

| Isis # | Seq ID No | Oligonucleotide Concentration | | | |
|---|---|---|---|---|---|
| | | 18.75 nM | 37.5 nM | 75 nM | 150 nM |
| 106747 | 58 | −32 | −48 | −62 | −76 |
| 337247 | 161 | +17 | −21 | −53 | −69 |
| 337270 | 184 | −16 | −27 | −67 | −87 |
| 337276 | 190 | −34 | −58 | −75 | −81 |
| 337284 | 198 | −49 | −62 | −66 | −68 |
| 337293 | 207 | −26 | −49 | −67 | −79 |
| 337303 | 217 | −47 | −59 | −69 | −71 |
| 337332 | 246 | −66 | −79 | −85 | −91 |
| 337333 | 247 | −46 | −70 | −82 | −90 |
| 337344 | 258 | −17 | −37 | −60 | −76 |
| 337348 | 262 | −53 | −76 | −83 | −86 |
| 337384 | 298 | −41 | −59 | −69 | −80 |
| 129695 | 391 | −4 | +2 | +8 | +3 |
| 129694 | 392 | +19 | −1 | +7 | +2 |
| 129690 | 393 | +4 | +10 | +8 | +11 |
| 129686 | 394 | +20 | +16 | +25 | +9 |
| 116847 | 395 | +45 | +33 | +22 | −2 |
| 113529 | 396 | +1 | +12 | −11 | −24 |

As shown in Table 19, measurement of target gene quantities using PPS 2033 demonstrates that the compounds tested inhibit human STAT3 mRNA expression in a dose-dependent manner.

An additional dose-response experiment was preformed in A549 cells. A549 cells were treated with 18.75, 37.5, 75, or 150 nM of oligonucleotide mixed with 3 ug/mL LIPOFECTIN per 100 nM oligonucleotide as described by other examples herein. Control oligonucleotides used were ISIS 129686 (SEQ ID NO: 394) and ISIS 129690 (SEQ ID NO: 393). Untreated cells served as controls. Following 16 hours of treatment, RNA was prepared from cells for subsequent real-time PCR analysis.

Human STAT3 mRNA expression levels were quantitated by real-time PCR using primer probe set PPS 199 and gene target quantities were normalized using Ribogreen as described in other examples herein. Data are averages from two experiments are shown in Table 20. A "−" or "+" designation in the dose response results indicates a decrease or increase of STAT 3 mRNA expression, respectively, relative to untreated control cells.

TABLE 20

Inhibition of human STAT 3 mRNA levels by chimeric
phosphorothioate oligonucleotides having 2'-MOE
wings and a deoxy gap: dose response
Percent change of STAT3 expression in A549 cells using PPS 199

| Isis # | Seq ID No | Oligonucleotide Concentration | | | |
|---|---|---|---|---|---|
| | | 18.75 nM | 37.5 nM | 75 nM | 150 nM |
| 106734 | 45 | −2 | −16 | −56 | −73 |
| 337332 | 246 | −31 | −61 | −77 | −87 |
| 337333 | 247 | −8 | −39 | −59 | −75 |
| 337348 | 262 | −26 | −43 | −55 | −77 |
| 129686 | 394 | +27 | +23 | +22 | +19 |
| 129690 | 393 | +30 | +27 | +16 | +27 |

As shown in Table 20, the compounds tested inhibit human STAT3 mRNA expression in A549 cells in a dose-dependent manner.

Example 22

Design and Screening of Duplexed Antisense Compounds Targeting STAT3

In accordance with the present invention, a series of nucleic acid duplexes comprising the antisense compounds of the present invention and their complements can be designed to target STAT3. The nucleobase sequence of the antisense strand of the duplex comprises at least a portion of an oligonucleotide targeted to STAT3 as disclosed herein. The ends of the strands may be modified by the addition of one or more natural or modified nucleobases to form an overhang. The sense strand of the dsRNA is then designed and synthesized as the complement of the antisense strand and may also contain modifications or additions to either terminus For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

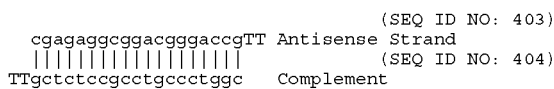

```
                                    (SEQ ID NO: 403)
cgagaggcggacgggaccgTT  Antisense Strand
|||||||||||||||||||                 (SEQ ID NO: 404)
TTgctctccgcctgccctggc  Complement
```

In another embodiment, a duplex comprising an antisense strand having the same sequence CGAGAGGCGGACGG-GACCG may be prepared with blunt ends (no single stranded overhang) as shown:

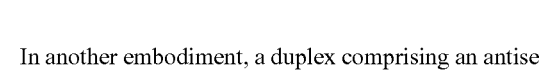

```
                                    (SEQ ID NO: 405)
cgagaggcggacgggaccg  Antisense Strand
|||||||||||||||||||                 (SEQ ID NO: 406)
gctctccgcctgccctggc  Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate STAT3.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM (a ratio of 6 μg/mL LIPOFECTIN per 100 nM duplex antisense compound). After 5 hours of treatment, the medium is replaced with fresh medium. Cells are harvested 16 hours after treatment, at which time RNA is isolated and target reduction measured by RT-PCR.

A series of nucleic acid duplexes comprising the antisense compounds of the present invention and their complements was designed to target STAT3 mRNA, using published sequence (GenBank Accession number L29277, incorporated herein as SEQ ID NO: 1). The nucleobase sequence of the antisense strand of the duplex is 20 nucleotides in length. The sequences of the antisense strand are listed in Table 21. The sense strand of the dsRNA is designed and synthesized as the complement of the antisense strand.

All compounds in Table 21 are oligodeoxynucleotides, 21 nucleotides in length with the two nucleotides on the 3' end being the TT overhang and with phosphodiester internucleoside linkages (backbones) throughout. These sequences are shown to contain thymine (T) but one of skill in the art will appreciate that thymine (T) is generally replaced by uracil (U) in RNA sequences.

TABLE 21 dsRNAs targeted to human STAT3

| ISIS # | REGION | TARGET SITE | TARGET SEQ ID | SEQUENCE | SEQ ID NO |
|---|---|---|---|---|---|
| 330249 | coding | 1669 | 1 | ATTCTTGGGATTGTTGGTCTT | 400 |
| 330247 | coding | 637 | 1 | CTCCAGCATCTGCTGCTTCTT | 401 |

The compounds in Table 21 were tested for their effects on human STAT3 expression in A549 cells. ISIS 330249 targets the same site as the antisense oligonucleotide ISIS 106734 (SEQ ID NO: 45) and ISIS 330247 targets the same site as the antisense oligonucleotide ISIS 113176 (SEQ ID NO: 115); thus, ISIS 106734 and ISIS 113176 were also tested. A549 cells were treated with oligonucleotide mixed with LIPO-FECTIN (Invitrogen Corporation, Carlsbad, Calif.) as described herein. Oligonucleotide concentrations used are indicated in Table 22. The control oligonucleotide used was ISIS 129698 (TTTGATCGAGGTTAGCCGTG, SEQ ID NO: 402). Cells were treated with oligonucleotide for 4 hours and harvested an additional 16 hours later. Untreated cells served as a control.

Human STAT3 mRNA expression levels were quantitated by real-time PCR using primer probe set PPS 199 and gene target quantities were normalized using Ribogreen as described in other examples herein. Data are averages from two experiments are shown in Table 22. A "−" or "+" designation indicates a decrease or increase of STAT 3 mRNA expression, respectively, relative to untreated control cells. Where present, "N.D." indicates not determined.

TABLE 22

Inhibition of STAT 3 mRNA levels by dsRNAs
Percent change in STAT3 mRNA expression in A549 cells by duplex antisense compounds

| Isis # | SEQ ID NO | Oligonucleotide Concentration | | | | | |
|---|---|---|---|---|---|---|---|
| | | 12.5 nM | 25 nM | 50 nM | 100 nM | 200 nM | 400 nM |
| 330249 | 400 | −64 | −70 | −80 | −83 | −87 | −81 |
| 106734 | 45 | −5 | −5 | −40 | −56 | −67 | −77 |
| 330247 | 401 | +11 | −19 | −15 | −16 | −20 | −48 |
| 113176 | 115 | +8 | +17 | +6 | 0 | −22 | −34 |
| 129698 | 402 | N.D. | N.D. | +41 | +42 | +1 | +22 |

Example 23

Inhibition of Tumor Growth in LNCaP Mouse Model Of Prostate Carcinoma

The LNCaP murine model of human prostate carcinoma is described in Kiyama et al., Cancer Res. 63:3575-3584, 2003, incorporated herein by reference. Briefly, LNCaP human prostatic carcinoma cells were cultured and maintained in RPMI medium (Life Technologies, Inc., Carlsbad, Calif.) supplemented with 5% heat inactivated fetal calf serum (FCS). About $1\times10^6$ LNCaP cells were inoculated subcutaneously with 0.1 ml of Matrigel (Becton Dickinson Labware, Franklin Lakes, N.J.) in the flank region of 6-8 week old male athymic nude mice (Harlan Sprague Dawley, Inc., Indianapolis, Ind.) via a 27 gauge needle under methoxyfluorane anesthesia. Mice bearing tumors between 300 and 500 $mm^3$ in volume were castrated via a scrotal approach and randomly assigned to treatment with 10 mg/kg of either ISIS 113176 human antisense or ISIS 129987 human mismatch control STAT 3 oligonucleotide intraperitoneally five times per week for the first week followed by three times per week thereafter. Treatment commenced beginning one day after castration. Tumor volumes and serum prostate specific antigen (PSA) measurements were performed once weekly. Tumor volumes were calculated by the formula L X W X H X 0.5236 (Gleave et al., Cancer Res. 51:1598-1605, 1992). Blood samples were obtained from tail vein incisions of mice, and serum PSA levels were determined by an enzymatic immunoassay kit with a lower limit of sensitivity of 0.2 µg/liter (Abbott IMX, Montreal, Quebec, Canada) according to the manufacturer's protocol.

ISIS 113176 suppressed the induction of serum PSA levels and tumor growth in the LNCaP xenograft model in castrated nude mice. Similar treatment of mice with the mismatch control oligonucleotide ISIS 129987 had no effect. The observed STAT3 antisense oligonucleotide-mediated effects on PSA and tumor volume were significantly different from mismatch oligonucleotide ISIS 129987 or saline treated controls (student's t-test, $p \geq 0.05$). Treatment effects were demonstrated out to the end of the observation period (10 weeks post-castration). To address the potential target-specific toxicit of this approach, normal mice were treated subcutaneously with an optimized murine STAT3 antisense oligonucleotide (up to 50 mg/kg three times per week for 2 weeks) and pharmacodynamic and toxological effects were evaluated in the blood, liver and bone marrow. STAT3 antisense oligonucleotide treatment resulted in 85% liver mRNA reduction and significant inhibition of STAT3 protein in the bone marrow pre-monocytic subpopulation. No overt changes were observed in complete blood counts, liver histology or bone marrow subpopulations in animals treated with STAT3 antisense oligonucleotide. Liver and bone marrow expression of STAT3 was significantly reduced by treatment with STAT3 antisense oligonucleotide. Thus, antisense oligonucleotides to STAT 3 represent a therapeutic opportunity for treatment of prostate cancer.

What is claimed is:

1. A compound comprising a modified oligonucleotide consisting of 15 to 30 linked nucleosides, wherein the modified oligonucleotide is complementary to an equal number of consecutive nucleobases selected from nucleobases 2941 to 3066 of SEQ ID NO:154.

2. The compound of claim 1, consisting of a single-stranded modified oligonucleotide.

3. The compound of claim 2, wherein the modified oligonucleotide is 100% complementary to an equal number of consecutive nucleobases selected from nucleobases 2941 to 3066 of SEQ ID NO:154.

4. The compound of claim 2, wherein at least one internucleoside linkage is a modified internucleoside linkage.

5. The compound of claim 4, wherein each internucleoside linkage is a phosphorothioate internucleoside linkage.

6. The compound of claim 2, wherein at least one nucleoside comprises a modified sugar.

7. The compound of claim 6, wherein the modified sugar is selected from the group consisting of a 2'-O-(2-methoxyethyl), and a bicyclic 2'-C,4'-C-oxymethylene linkage 4'-$(CH_2)_n$—O-2', wherein n is 1 or 2.

8. The compound of claim 2, wherein at least one nucleoside comprises a modified nucleobase.

9. The compound of claim 8, wherein the modified nucleobase is a 5-methylcytosine.

10. The compound of claim 1, wherein the modified oligonucleotide comprises:
a gap segment consisting of linked deoxyribonucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

11. The compound of claim 10, wherein the modified oligonucleotide comprises:
a gap segment consisting of ten linked deoxyribonucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage; and wherein each cytosine in said antisense oligonucleotide is a 5-methylcytosine.

12. The compound of claim 2, wherein the modified oligonucleotide consists of 20 linked nucleosides.

13. A composition comprising a modified oligonucleotide consisting of 15 to 30 linked nucleosides, wherein the modified oligonucleotide is complementary to an equal number of consecutive nucleobases selected from nucleobases 2941 to 3066 of SEQ ID NO:154.

14. The composition of claim 13, wherein the modified oligonucleotide consists of a single-stranded modified oligonucleotide.

15. The composition of claim 13, wherein the modified oligonucleotide consists of 20 linked nucleosides.

* * * * *